United States Patent
Turner et al.

(10) Patent No.: US 11,142,793 B2
(45) Date of Patent: *Oct. 12, 2021

(54) NUCLEIC ACID SEQUENCING WITH NANOSCALE ELECTRODE PAIRS

(71) Applicant: Pacific Biosciences of California, Inc., Menlo Park, CA (US)

(72) Inventors: Stephen Turner, Eugene, OR (US); Jeremiah Hanes, Woodside, CA (US); Keith Bjornson, Fremont, CA (US)

(73) Assignee: Pacific Biosciences of California, Inc., Menlo Park, CA (US)

(*) Notice: Subject to any disclaimer, the term of this patent is extended or adjusted under 35 U.S.C. 154(b) by 112 days.

This patent is subject to a terminal disclaimer.

(21) Appl. No.: 16/668,351

(22) Filed: Oct. 30, 2019

(65) Prior Publication Data

US 2020/0102613 A1 Apr. 2, 2020

Related U.S. Application Data

(63) Continuation of application No. 15/836,736, filed on Dec. 8, 2017, now Pat. No. 10,934,583, which is a (Continued)

(51) Int. Cl.
*C12Q 1/68* (2018.01)
*C12Q 1/6874* (2018.01)
(Continued)

(52) U.S. Cl.
CPC ......... *C12Q 1/6874* (2013.01); *C12Q 1/6823* (2013.01); *G01N 27/227* (2013.01)

(58) Field of Classification Search
CPC ............ C12Q 2521/101; C12Q 1/6874; C12Q 1/6823; C12Q 2521/543; C12Q 2563/113;
(Continued)

(56) References Cited

U.S. PATENT DOCUMENTS 5,143,854 A 9/1992 Pirrung et al.
5,723,584 A 3/1998 Schatz
(Continued)

FOREIGN PATENT DOCUMENTS

EP 2035584 B1 1/2011
EP 1963530 B1 7/2011
(Continued)

OTHER PUBLICATIONS

Aime, et al., "High Sensitivity Lanthanide (III) Based Probes for MR-Medical Imaging," Coordination Chemistry Reviews (2006) 250:1562-1579.
(Continued)

*Primary Examiner* — Betty J Forman
(74) *Attorney, Agent, or Firm* — Robert H. Reamey

(57) ABSTRACT

Sequencing methods, devices, and systems are described. Arrays of nanoscale electronic elements comprising two electrodes separated by an insulating layer are used to provide sequence information about a template nucleic acid in a polymerase-template complex bound proximate to the insulating region. A sequencing reaction mixture comprising nucleotide analogs having impedance labels is introduced to the array of nanoscale electronic elements under conditions of polymerase mediated nucleic acid synthesis. The time sequence of incorporation of nucleotide analogs is determined by identifying the types of labels of the nucleotide analogs that are incorporated into the growing strand using measured impedance.

18 Claims, 10 Drawing Sheets

Related U.S. Application Data continuation of application No. 14/918,957, filed on Oct. 21, 2015, now Pat. No. 9,868,987, which is a continuation of application No. 14/270,099, filed on May 5, 2014, now Pat. No. 9,708,656.

(60) Provisional application No. 61/880,293, filed on Sep. 20, 2013, provisional application No. 61/820,066, filed on May 6, 2013.

(51) Int. Cl.
    *C12Q 1/6823*     (2018.01)
    *G01N 27/22*     (2006.01)

(58) Field of Classification Search
    CPC ........ C12Q 2563/116; C12Q 2565/607; G01N 27/227; G01N 27/4145; G01N 27/00
    See application file for complete search history.

(56) References Cited

U.S. PATENT DOCUMENTS

| | | |
|---|---|---|
| 5,874,239 A | 2/1999 | Schatz |
| 5,932,433 A | 8/1999 | Schatz |
| 6,153,442 A | 11/2000 | Pirio et al. |
| 6,265,552 B1 | 7/2001 | Schatz |
| 6,828,800 B2 | 12/2004 | Reich et al. |
| 7,056,661 B2 | 6/2006 | Korlach et al. |
| 7,141,676 B1 | 11/2006 | Wilbur et al. |
| 7,315,019 B2 | 1/2008 | Turner et al. |
| 7,763,423 B2 | 7/2010 | Roitman et al. |
| 7,888,013 B2 | 2/2011 | Miyahara et al. |
| 7,948,015 B2 | 5/2011 | Rothberg et al. |
| 7,981,604 B2 | 7/2011 | Quake |
| 7,981,632 B2 | 7/2011 | Schmidt |
| 7,993,891 B2 | 8/2011 | Roitman et al. |
| 8,034,222 B2 | 10/2011 | Myung et al. |
| 8,133,672 B2 | 3/2012 | Bjornson et al. |
| 8,137,942 B2 | 3/2012 | Roitman et al. |
| 8,193,123 B2 | 6/2012 | Rank et al. |
| 8,232,584 B2 | 7/2012 | Lieber et al. |
| 8,252,910 B2 | 8/2012 | Korlach et al. |
| 8,389,676 B2 | 3/2013 | Christians |
| 8,652,779 B2 | 2/2014 | Turner et al. |
| 8,703,497 B2 | 4/2014 | Sun et al. |
| 8,864,969 B2 | 10/2014 | Liu et al. |
| 8,871,921 B2 | 10/2014 | O'Halloran |
| 8,961,757 B2 | 2/2015 | Nuckolls et al. |
| 9,017,937 B1 | 4/2015 | Turner et al. |
| 9,040,237 B2 | 5/2015 | Koo et al. |
| 9,063,081 B2 | 6/2015 | Sauer et al. |
| 9,228,967 B2 | 1/2016 | Sauer et al. |
| 9,238,835 B2 | 1/2016 | Sun et al. |
| 9,341,592 B2 | 5/2016 | Takulapalla et al. |
| 9,708,656 B2 | 7/2017 | Turner et al. |
| 9,868,987 B2 * | 1/2018 | Turner .............. G01N 27/227 |
| 10,125,391 B2 | 11/2018 | Turner et al. |
| 10,934,583 B2 * | 3/2021 | Turner .............. C12Q 1/6874 |
| 2001/0055766 A1 | 12/2001 | Aristarhov et al. |
| 2005/0106587 A1 | 5/2005 | Klapproth et al. |
| 2006/0199193 A1 | 9/2006 | Koo et al. |
| 2006/0246497 A1 | 11/2006 | Huang et al. |
| 2006/0269927 A1 | 11/2006 | Lieber et al. |
| 2009/0181381 A1 | 7/2009 | Oldman et al. |
| 2009/0208922 A1 | 8/2009 | Choi et al. |
| 2009/0233291 A1 | 9/2009 | Chen et al. |
| 2010/0035254 A1 | 2/2010 | Williams |
| 2010/0167299 A1 | 7/2010 | Korlach et al. |
| 2010/0331194 A1 | 12/2010 | Turner et al. |
| 2011/0014151 A1 | 1/2011 | Nilsson et al. |
| 2011/0171655 A1 | 7/2011 | Esfandyarpour et al. |
| 2011/0174620 A1 | 7/2011 | Choi et al. |
| 2011/0177496 A1 | 7/2011 | Williams et al. |
| 2011/0236984 A1 | 9/2011 | Sun et al. |
| 2011/0319276 A1 * | 12/2011 | Liu .............. C12Q 2521/525 506/7 |
| 2012/0021918 A1 | 1/2012 | Bashir et al. |
| 2012/0052490 A1 | 3/2012 | Eid et al. |
| 2012/0244537 A1 | 9/2012 | Sun et al. |
| 2013/0052130 A1 | 2/2013 | Davis et al. |
| 2013/0078622 A1 | 3/2013 | Collins et al. |
| 2013/0109577 A1 * | 5/2013 | Korlach .............. G01N 27/00 506/4 |
| 2013/0165328 A1 | 6/2013 | Previte et al. |
| 2013/0225416 A1 | 8/2013 | Altmann et al. |
| 2013/0285680 A1 | 10/2013 | Sorgenfrei et al. |
| 2013/0316912 A1 | 11/2013 | Bjornson |
| 2013/0337567 A1 | 12/2013 | Shin et al. |
| 2014/0178862 A1 | 6/2014 | Su et al. |
| 2014/0235462 A1 | 8/2014 | Kotseraglou et al. |
| 2014/0252460 A1 | 9/2014 | Lee et al. |
| 2015/0017655 A1 | 1/2015 | Huang et al. |
| 2015/0065353 A1 | 3/2015 | Turner et al. |
| 2015/0093849 A1 | 4/2015 | Shepard et al. |
| 2015/0171326 A1 | 6/2015 | Guo et al. |
| 2016/0011186 A1 | 1/2016 | Oldham et al. |
| 2016/0017416 A1 | 1/2016 | Boyanov et al. |

FOREIGN PATENT DOCUMENTS

| | | |
|---|---|---|
| WO | 1991007087 A1 | 5/1991 |
| WO | 1999060400 A1 | 11/1999 |
| WO | 2008051530 A2 | 5/2008 |
| WO | 2009006445 A2 | 1/2009 |
| WO | 2011082419 A2 | 7/2011 |
| WO | 2012065043 A2 | 5/2012 |
| WO | 2012097074 A2 | 7/2012 |
| WO | 2013056241 A1 | 4/2013 |
| WO | 2014024041 A1 | 2/2014 |
| WO | 2014149779 A1 | 9/2014 |
| WO | 2014182630 A1 | 11/2014 |
| WO | 2016010975 A2 | 1/2016 |

OTHER PUBLICATIONS

Akhterov, et al., "Observing Lysozyme's Closing and Opening Motions for High-Resolution Single-Molecule Enzymology," ACS Chemical Biology (2015) 10:1495-1501.

Alivisatos, et al., "Nanotools for Neuroscience and Brain Activity Mapping," ACS Nano (2013) 7(3):1850-1866.

Balasubramanian and Burghard, "Chemically Functionalized Carbon Nanotubes," Small (2005) 1(2):180-192.

Beckett, et al., "A Minimal Peptide Substrate in Biotin Holoenzyme Synthetase-Catalyzed Biotinylation," Protein Science (1999) 8:921-929.

Besteman, et al., "Enzyme-Coated Carbon Nanotubes as Single-Molecule Biosensors," Nano Letters (2003) 3(6):727-30.

Bouilly, et al., "Single-Molecule Reaction Chemistry in Patterned Nanowells," Nano Letters (2016) 16:4679-85.

Bunimovich, et al., "Quantitative Real-Time Measurements of DNA Hybridization with Alkylated Nonoxidized Silicon Nanowires in Electrolyte Solution," J. Am. Chem. Soc. (2006) 128:16323-16331.

Bushmaker, et al., "Single-Ion Adsorption and Switching in Carbon Nanotubes," Nature Communications (2016) 7:10475 DOI: 10.1038/ncomms10475.

Calvaresi, et al., "The Devil and Holy Water: Protein and Carbon Nanotube Hybrids," Accounts of Chemical Research (2012) A-J.

Chen, et al., "DNA Sequencing Using Electrical Conductance Measurements of a DNA Polymerase," Nature Nanotechnology (2013) DOI: 10.1038/NNAN0.2013.71.

Chen, et al., "Silicon Nanowire Field-Effect Transistor-Based Biosensors for Biomedical Diagnosis and Cellular Recording Investigation," Nano Today (2011) 6(2):131-154.

Chivers, et al.,"A Streptavidin Variant with Slower Biotin Dissocation and Increased Mechanostability," Nat. Methods (2010) 7(5):391-393.

Choi, et al., "Dissecting Single-Molecule Signal Transduction in Carbon Nanotube Circuits with Protein Engineering," Nano Lett (2013) 13(2):625-631.

(56) References Cited

OTHER PUBLICATIONS

Choi, et al., "Single Molecule Dynamics of Lysozyme Processing Distinguishes Linear and Cross-Linked Peptidoglycan Substrates," J. Am. Chem. Soc. (2012) 134(4):2032-2035.
Choi, et al., "Single-Molecule Lysozyme Dynamics Monitored by an Electronic Circuit," Science (2012) 335:319-324.
Derenskyi, et al., "Carbon Nanotube Network Ambipolar Field-Effect Transistors with 108 On/Off Ratio," Advanced Materials (2014) 26:5969-75.
Dietrich, et al., "Tethered Particle Motion Mediated by Scattering From Gold Nanoparticles and Darkfield Microscopy," Journal of Nanophotonics (2009) DOI: 10.1117/1.3174445.
Eid et al., "Real-Time DNA Sequencing From Single Polymerase Molecules," Science (2009) 323:133-138.
Elnathan, et al., "Biorecognition Layer Engineering: Overcoming Screening Limitaitons of Nanowire-Based FET Devices," NanoLetts (2012) 12:5245-54.
Farah, et al., "Point Mutagenesis and Cocrystallization of Wild-Type and Mutant Proteins: A Study of Solid-Phase Coexistence in Two-Dimensional Protein Arrays," Langmuir (2001) 17:5731-5735.
Fierer, et al., "SpyLigase Peptide-Peptide Ligation Polymerizes Affibodies to Enhance Magnetic Cancer Cell Capture," Proc. Natl. Acad. USA (2014) E1176-E1181.
Furukawa, et al., "Development of Novel Yeast Cell Surface Display System for Homo-Oligomeric Protein by Coexpression of Native and Anchored Subunits," Biotechnol. Prog. (2006) 22:994-997.
Gao, et al., "General Strategy for Biodetection in High Ionic Strength Solutions Using Transistor-Based Nanoelectronic Sensors," Nano Letters (2015) 15:2143-2148.
Green, "Avidin," Adv. Protein Res. (1975) 29:85-133.
Grigoryan, et al., "Computational Design of Virus-Like Protein Assemblies on Carbon Nanotube Surfaces," Science (2011) 332:1071-1076.
He, et al., "Direct Measurement of Single-Molecule DNA Hybridization Dynamics with Single-Base Resolution," Angew. Chem. Int. (2016) 55:9036-9040.
He, et al., "Single Nucleotide Plymorphism Genotyping in Single-Molecule Electronic Circuits," Adv. Sci. (2017) 4:1700158.
Holmberg, et al., "The Biotin-Streptavidin Interaction can be Reversibly Broken Using Water at Elevated Temperatures," Electrophoresis (2005) 26:501-510.
Horton, et al., "Engineering Hybrid Genes Without the Use of Restriction Enzymes: Gene Splicing by Overlap Extension," Gene (1989) 77(1):61-8.
Howarth et al., "Imaging Proteins in Live Mammalian Cells with Biotin Ligase and Monovalent Streptavidin," Nature Protocols (2008) 3(3):534-545.
Howarth, et al., "A Monovalent Streptavidin with Single Femtomolar Biotin Binding Site," Nature Methods (2006) 3(4):267-73.
Hughes and Walsh, "What Makes a Good Graphene-Binding Peptide? Adsorption of Amino Acids and Peptides at Aqueous Graphene Interfaces," J. Mater. Chem. B. (2015) 3:3211-3221 (author version).
Islam, et al., "A General Approach for High Yield Fabrication of CMOS-Compatible All-Semiconducting Carbon Nanotube Field Effect Transistors," NanoTech (2012) doi:10-1088/0957-4484/23/12/125201.
Jia, et al., "Covalently Bonded Single-Molecule Junctions with Stable and Reversible Photoswitched Conductivity," Science (2016) 352(6292):1443-5.
Kaniber, et al., "Covalently Binding the Photosystem I to Carbon Nanotubes," PACS: 81.07.Nb, 85.65.+h, 81.07.De.
Kim, et al., "Protein Conjugation with Genetically Encoded Unnatural Amino Acids," Curr Opin Chem Biol. (2013) 17(3):412-419.
Kormondy, et al., "High Yield Assembly and Electron Transport Investigation of Semiconducting-Rich Local-Gated Single-Walled Carbon Nanotube Field Effect Transistors," Nanotechnology (2011) doi:10.1088/0957-4484/22/41/415201.

Kumar, et al., "PEG-labeled Nucleotides and Nanopore Detection for Single Molecule DNA Sequencing by Synthesis," Scientific Reports (2012) 2(684):1-8.
Kuzmany, et al., "Functionalization of Carbon Nanotubes," Synthetic Metals (2004) 141: 113-122.
Lawrence, et al., "Supercharging Proteins Can Impact Unusual Resilience," J. Am. Chem. Soc. (2007) 129(33): 10110. doi:10.1021/ja071641y.
Lerner et al., "Toward Quantifying the Electrostatic Transduction Mechanism in Carbon Nanotube Molecular Sensors," JACS (2012) 134:14318-21.
Levene et al., "Zero-mode Waveguides for Single-molecule Analysis at High Concentration" Science (2003) 299:682-686.
Li, et al., "Advanced Fabrication of Si Nanowire FET Structures by Means of a Parallel Approach," NanoTech (2014) doi:10.1088/0957-4484/25/27/275302.
Li, et al., "Direct Real-Time Detection of Single Proteins Using Silicon Nanowire-Based Electrical Circuits," Nanoscale (2016) 8:16172-6.
Liu, et al., "Single-Molecule Detection of Proteins Using Aptamer-Functionalized Molecular Electronic Devices," Angew. Chem. Int. (2011) 50:2496-2502.
Lu, et al., "Label-Free and Rapid Electrical Detection of hTSH with CMOS-Compatible Silicon Nanowire Transistor Arrays," Applied Materials & Interfaces (2014) 6:20378-20384.
Luong, et al., "Purification, Functionalization, and Bioconjugation of Carbon Nanotubes," Bioconjugation Protocols: Strategies and Methods, Methods in Molecular Biology, vol. 751, DOI 10.1007/978-1-61779-151-2_32.
Olsen, et al., "Electronic Measurements of Single-Molecule Processing by DNA Plymerase I (Klenow Fragment)," J Am Chem Soc (2013) 135(21):7855-60.
Park, et al., "Array-Based Electrical Detection of DNA with Nanoparticle Probes," Science (2002) 295:1503-1506.
EP Search Report dated Nov. 5, 2019 for related case EP 19184152.7.
Patolsky, et al., "Detection, Stimulation and Inhibition of Neuronal Signals with High-Density Nanowire Transistor Arrays," Science (2006) 313:1100-4.
Patolsky, et al., "Electrical Detection of Single Viruses," PNAS (2004) 101(39):14017-14022.
Phillip, et al., "Common Crowding Agents Have Only a Small Effect on Protein-Protein Interactions," Biophysical Journal (2009) 97:875-85.
Pugliese, et al., "Processive Incorporation of Deoxynucleoside Triphosphate Analogs by Single-Molecule DNA Polymerase I (Klenow Fragment) Nanocircuits," JACS (2015) 137:9587-94.
Qi, et al., "The Effect of Macromolecular Crowding on the Electrostatic Component of Barnase-Barstar Binding: A Computational, Implicit Solven-Based Study," PLOS One (2014) 9(6):e98618.
Ringler and Schulz, "Self-Assembly of Proteins into Designed Networks," Science (2003) 302:106-109.
Russell and Claridge, "Peptide Interfaces with Graphene: An Merging Intersection of Analytical Chemistry, Theory and Materials," Anal. Bioanal. Chem (2016) 408:2649-2658.
Sattely, et al., "Total Biosynthesis: In Vitro Reconstitution of Polyketide and Nonribosomal Peptide Pathways," Natural Product Reports (2008) 25:757-793.
Schechter, et al., "Renal Accumulation of Streptavidin: Potential Use for Targeted Therapy to the Kidney," Kidney International (1995) 47:1327-1335.
Schoene, et al., "SpyTag/SpyCatcher Cyclization Confers Resilience to Boiling on a Mesophilic Enzyme," Agnew. Chem. Int. Ed. (2014) 53: 1-5.
Setiadi, et al., "Room-Temperature Discrete-Charge-Fluctuation Dynmaics of a Single Molecule Adsorbed on a Carbon Nanotube," Nanoscale (2017) 9:10674-83.
Shimoboji, et al., "Mechanistic Investigation of Smart Polymer-Protein Conjugates," Bioconjugate Chemistry (2001) 12:314-319.
Shoorideh, et al., "On the Origin of Enhanced Sensitivity in Nanoscale FET-Based Biosensors," PNAS (2014) 111(14):5111-6.
Sorgenfrei, et al., "Debye Screening in Single-Molecule Carbon Nanotube Field-Effect Sensors," Nano Letters (2011) 11:3739-43.

(56) References Cited

OTHER PUBLICATIONS

Sorgenfrei, et al., "Label-Free Single-Molecule Detection of DNA-Hybridization Kinetics with a Carbon Nanotube Field-Effect Transistor," Nature Nanotechnology (2011) 6:126-132.
Stern, et al., "Importance of the Debye Screening Length on Nanowire Filed Effect Transistor Sensors," Nano Letters (2007) 7(11):3405-3409.
Tahiri-Alaoui, et al., "High Affinity Nucleic Acid Aptamers for Streptavidin Incorporated into Bi-Specific Capture Ligands," Nuc. Ac. Res (2002) 30(10):e45.
Takakura, et al., "Tamavidins—Novel Avidin-Like Biotin-Binding Proteins from the Tamogitake Mushroom," FEBS Journal (2009) 276(5):1383-97.
Thompson, et al., "Engineering and Identifying Supercharged Proteins for Macromolecule Delivery into Mammalian Cells," Methods in Enzymology (2012) 503:293-318.
Tian, et al., "Three-Dimensional, Flexible Nanoscale Field Effect Transistors as Localized Bioprobes," Science (2010) 329(5993):830-834.
Timko, et al., "Response to Comment on 'Detection, Stimulation, and Inhibition of Neuronal Signals with High-Density Nanowire Transistor Arrays'," Science (2009) 323:1429c.
University of Illinois, Grant Report dated Dec. 1, 2006 for Grant No. FA9550-04-1-0214, titled, "Single Molecule Detection Using a Silicon Nanopore-Nanotransistor Integrated Circuit."
Vernicks, et al., "Electostatic Melting in a Single-Molecule Field-Effect Transistor with Applications in Genomic Identification," Nature Commun (2017) 8:15450.
Wang, et al., "Point Decoration of Silicon Nanowires: An Approach Toward Silicon-Molecule Electrical Detection," Angew Chem. Int. (2014) 53:5038-43.
Wang, et al., "Selective Fabrication of Quasi-Parallel Single-Walled Carbon Nanotubes on Silicon Substrates," NanoTechnology (2010) doi:10.1088/0957-4484/21/39/395602.
Wei, et al., "Bacterial Virulence Proteins as Tools to Rewire Kinase Pathways in Yeast and Immune Cells," Nature (2012) 488:384-388.
Wilbur et al., "Design and Synthesis of Bis-Biotin-Containing Reagents for Applications Utilizing Monoclonal Antibody-Based Pretargeting Systems and Streptavidin Mutants," Bioconjugate Chem. 21(7):1225-1238.
Wilbur, et al., "Biotin Reagents for Antibody Pretargeting. 2. Synthesis and in Vitro Evaluation of Biotin Dimers and Trimers for Cross-Linking of Streptavidin," Bioconjugate Chemistry (1997) 8(6):819-32.
Wilbur, et al., "Biotin Reagents for Antibody Pretargeting. 3. Synthesis, Radioiodination, and Evaluation of Biotinylated Starburst Dendrimers," Bioconjugate Chemistry (1998) 9:813-825.
Wilson, et al., "The Use of mRNA Display to Select High-Affinity Protein-Binding Peptides," Proc. Natl. Acad. Sci. USA (2001) 98:3750-3755.
Xia, et al., "Quantifying the Kinetic Stability of Hyperstable Proteins via Time Dependent SDS Trapping," Biochemistry (2012) 51:100-107.
York, et al., "Particle Detection Using an Integrated Capacitance Sensor," Sensors and Actuators (2001) 92:74-79.
You, et al., "Real-Time Monitoring of Conformational Transitions of Single-Molecule Histone Deacetylase 8 with Nanocircuits," Chem Commun. (2017) 53:3307-10.
Zakeri, et al., "Peptide Tag Forming a Rapid Covalent Bond to a Protein, Through Engineering a Bacterial Adhesin," PNAS (2012) 109(12):E690-7.
Zareh, et al., "Single-Molecule Imaging of Protein Adsorption Mechanisms to Surfaces," Microscopy Research and Technique (2011) 74:682-687.
Zhang and Lieber, "Nano-Bioelectronics," Chemical Reviews (2015) DOI: 10.1021/acs.chemrev.5b00608.
Zhang, et al., "Controlling Macromolecular Topology with Genetically Encoded SpyTag-SpyCatcher Chemistry," J. Am. Chem. Soc. (2013) 135: 13988-13997.
Zhang, et al., "Effect of Chemical Oxidation on the Structure of Single-Walled Carbon Nanotubes," J. Phys. Chem. B (2003) 107:3712-3718.
Zhu, et al., "Electrical-Impedance-Spectroscopy Characterization of Individually Immobilized Single Particles and Yeast Cells," 16th International Conference on Miniaturized Systems for Chemistry and Life Sciences (Oct. 28-Nov. 1, 2012) Okinawa, Japan, p. 995-997.
International Search Report and Written Opinion dated Sep. 2, 2014 for related case PCT/US2014/036843.
International Preliminary Report on Patentability dated Nov. 19, 2015 for related case PCT/US2014/036843.
International Search Report and Written Opinion dated Nov. 10, 2016 for related case PCT/US2016/045381.
Supplementary Search Report dated Jan. 4, 2017 for related case EP 14794438.3.
International Preliminary Report on Patentability dated Feb. 15, 2018 for related case PCT/US2016/045381.
Noor et al., "Silicon Nanowires as Filed-Effect Transducers for Biosensor Development: A Review," Analytica Chimica Acta (2014) 825:1-25.
Padeste et al., "Molecular Assembly of Redox-Conductive Ferrocene-Streptavidin Conugates—Towards Bio-Electrochemical Devices," Biosensors and Bioelectronics (2004) 20:545-552.
First Exam Report dated May 2, 2018 for related case EP 14794438.3.
First Exam Report dated Sep. 12, 2018 for related case CN 201480038761.4.
EP Search Report dated Feb. 4, 2019 for related case EP 16833817.6.
Second Exam Report dated May 30, 2019 for related case CN 201480038761.4.

\* cited by examiner

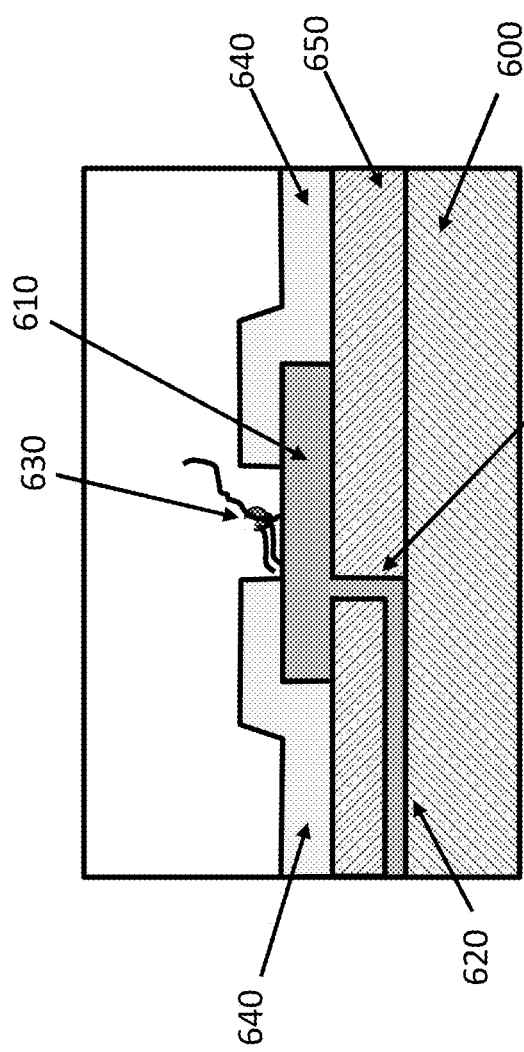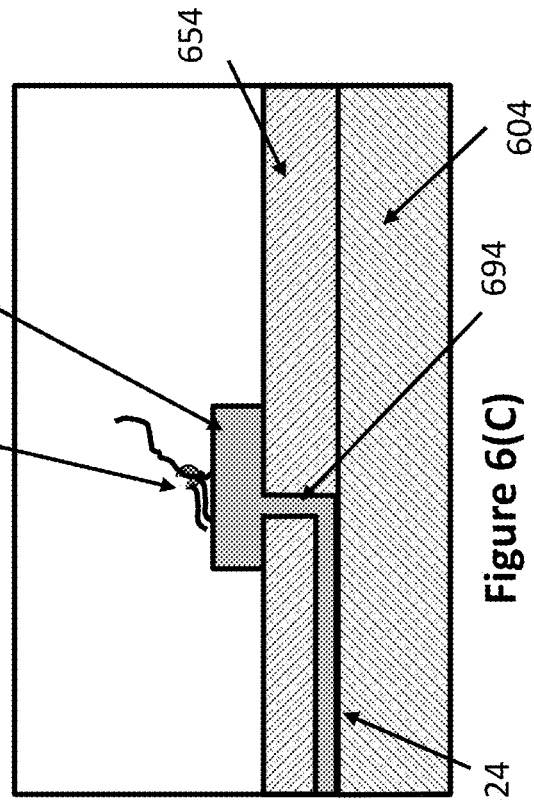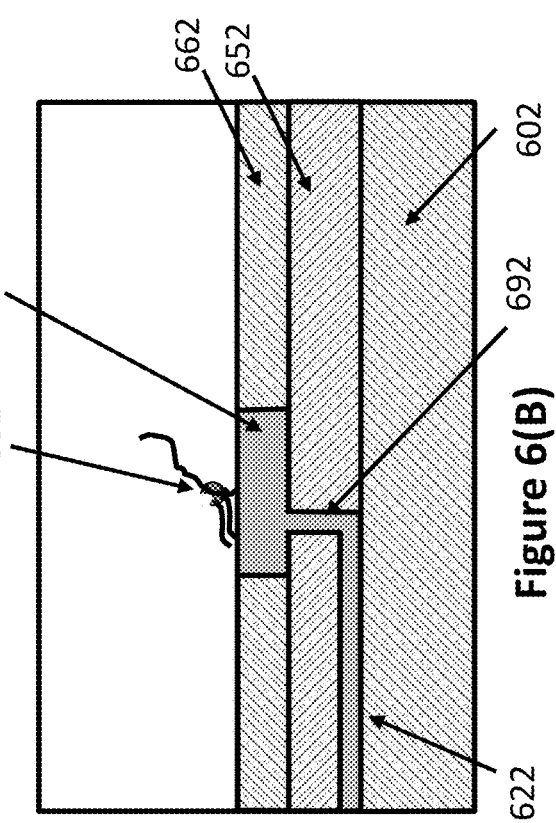

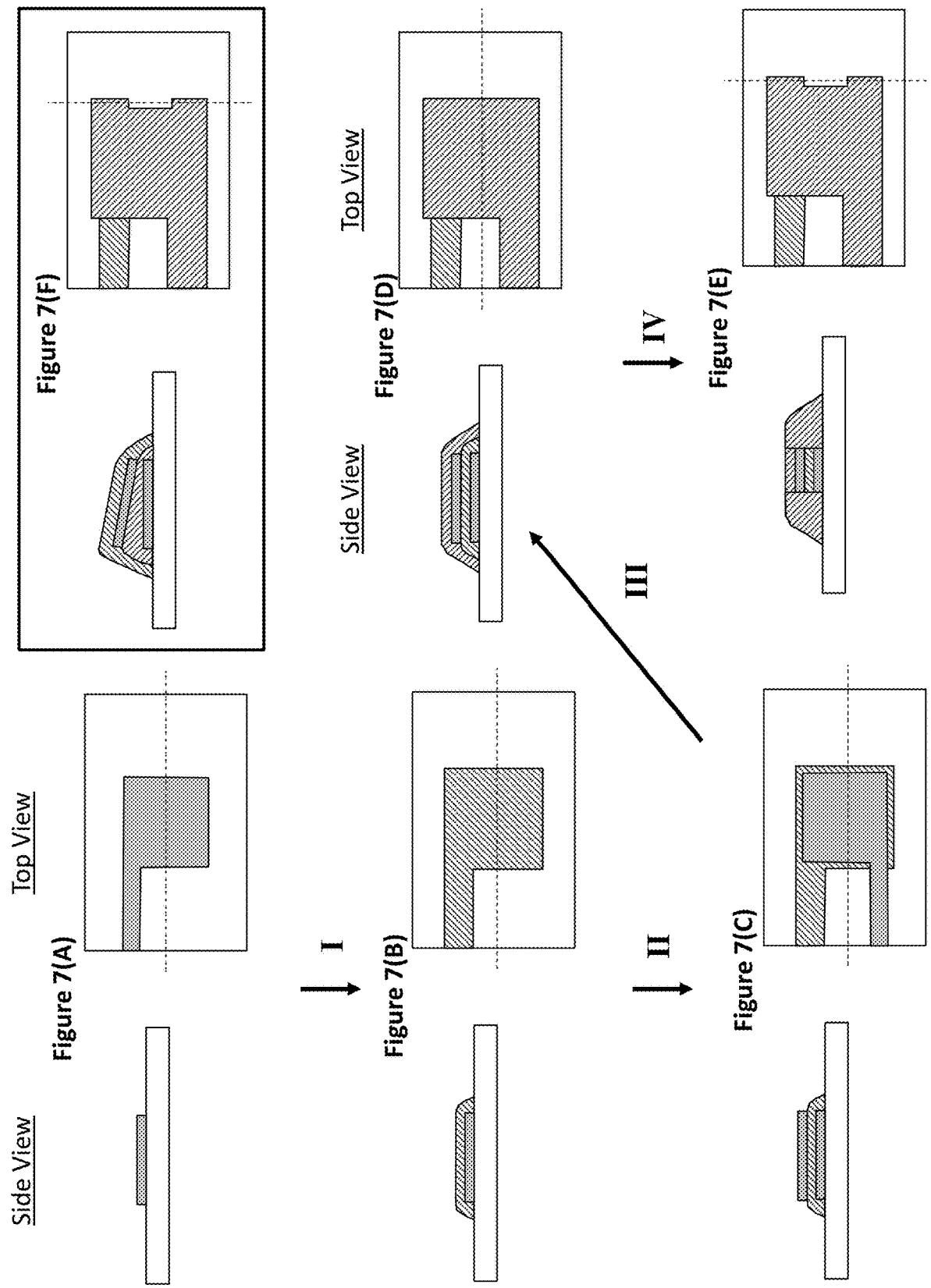

NUCLEIC ACID SEQUENCING WITH NANOSCALE ELECTRODE PAIRS

CROSS-REFERENCE TO RELATED APPLICATIONS

This application is a continuation application of Ser. No. 15/836,736 filed Dec. 8, 2017, which is a continuation application of Ser. No. 14/918,957 filed Oct. 21, 2015, now U.S. Pat. No. 9,868,987, which is a continuation application of Ser. No. 14/270,099 filed May 5, 2014, now U.S. Pat. No. 9,708,656, which claims the benefit of Provisional Patent Application No. 61/880,293 filed Sep. 20, 2013 and Provisional Patent Application No. 61/820,066, filed May 6, 2013, which are incorporated herein by reference for all purposes.

STATEMENT REGARDING FEDERALLY SPONSORED RESEARCH

Not Applicable.

BACKGROUND OF THE INVENTION

Nucleic acid sequence data is valuable in myriad applications in biological research and molecular medicine, including determining the hereditary factors in disease, in developing new methods to detect disease and guide therapy (van de Vijver et al. (2002) "A gene-expression signature as a predictor of survival in breast cancer," New England Journal of Medicine 347: 1999-2009), and in providing a rational basis for personalized medicine. Obtaining and verifying sequence data for use in such analyses has made it necessary for sequencing technologies to undergo advancements to expand throughput, lower reagent and labor costs, and improve accuracy (See, e.g., Chan, et al. (2005) "Advances in Sequencing Technology" (Review) Mutation Research 573: 13-40 which is incorporated herein in its entireties for all purposes.

Various methods of sequencing are used and each has its strengths and weaknesses. Single molecule real time sequencing has advantages over other sequencing methodologies including the ability to provide longer read lengths. Many current methods of sequencing use optical labels. There is a need for improved sequencing instruments and methods that use non-optical readouts, and in particular real time single molecule sequencing methods with these characteristics.

Electronic detection of single molecules and single particles, including by capacitive, impedance, and conductive methods has been demonstrated. The current invention provides instruments, devices and methods for non-optical real-time single molecule sequencing.

BRIEF SUMMARY OF THE INVENTION

In some aspects, the invention provides a method for nucleic acid sequencing comprising: providing a substrate comprising an array of nanoscale electronic elements capable of measuring impedance, wherein a plurality of the nanoscale elements comprise a single polymerase enzyme complex, comprising a polymerase enzyme and a template nucleic acid, attached to or proximate to the nanoscale electronic element; exposing the substrate to a plurality of types of nucleotide analogs, each type comprising a different impedance label attached to the phosphate portion of the nucleotide analog under conditions whereby polymerase mediated nucleic acid synthesis occurs, resulting in incorporations of nucleotide analogs and cleavage of the corresponding impedance label, and resulting in the growth of a nascent nucleic acid strand; measuring the impedance at each of the plurality of nanoscale electronic elements, whereby when a nucleotide analog resides in the active site of the enzyme, the impedance label on the nucleotide analog produces a measurable impedance change at the nanoscale electronic element; monitoring the impedance at the plurality of nanoscale elements over time, whereby changes in impedance indicate an incorporation event for a type of nucleotide analog; and using the measured impedance over time to identify the type of nucleotide analog incorporated to determine a sequence of the template nucleic acid.

In some cases the nanoscale electronic elements measure capacitance, conductivity, or a combination of capacitance and conductivity. In some cases the nanoscale electronic elements comprise nanoFET devices. In some cases the gate of the nanoFETs comprises a nanowire. In some cases the gate of the nanoFETs comprises doped silicon.

In some cases the substrate is exposed to four types of nucleotide analogs corresponding to A, G, C, T, or A, G, C, U, each of the four types of nucleotide analogs having a different impedance label. In some cases the impedance label is attached to the polyphosphate portion through a linker. In some cases the impedance label comprises either a capacitance label or a conductivity label.

In some aspects, the invention provides a chip for sequencing a plurality of single nucleic acid template molecules comprising: a substrate comprising; a plurality of nanoscale electronic elements, each nanoscale electronic element comprising a single polymerase enzyme complex bound to the nanoscale electronic element or to the substrate proximate nanoscale electronic element, wherein the polymerase enzyme complex comprises a polymerase enzyme and a template nucleic acid; wherein the substrate is configured such that the nanoscale electronic element comes into contact with a sequencing reaction mixture comprising a plurality of types of nucleotide analogs, each having different impedance labels; and a plurality of electrical connection sites for bringing current and voltage to the nanoscale electronic elements, and for receiving electrical signals from nanoscale electronic elements.

In some cases the nanoscale electronic elements comprises nanoscale capacitive devices or nanoFET devices. In some cases the nanoscale electronic elements comprise nanoFETs and the gates of each of the nanoFETs comprise a nanowire. In some cases the nanoscale electronic elements comprise nanoFETs and the gates of the nanoFETs comprise doped silicon. In some cases the substrate comprises greater than 1,000 nanoscale electronic elements.

In some cases the substrate comprises greater than 10,000 nanoscale electronic elements. In some cases the substrate comprises about 1,000 nanoscale electronic elements to about 10 million nanoscale electronic elements. In some cases the substrate comprises about 10,000 nanoscale electronic elements to about 1 million nanoscale electronic elements.

In some cases the substrate comprises electronics for one or more of: providing electrical signals to the nanoscale electronic elements, measuring the electrical signals at the nanoscale electronic elements, analog to digital conversion, signal processing, and data storage. In some cases the electronics comprise CMOS elements.

In some aspects the invention provides a system for sequencing template nucleic acids comprising: a housing having housing electrical connection sites; a chip that reversibly mates with the housing comprising a substrate comprising; chip electrical connection sites that reversibly connect to the housing electrical connection sites; a plurality of nanoscale electronic elements, each nanoscale electronic element comprising a single polymerase enzyme complex bound to the nanoscale electronic element or to the substrate proximate to the nanoscale electronic elements, wherein the polymerase enzyme complex comprises a polymerase enzyme and a template nucleic acid; a fluid reservoir for contacting a sequencing reaction mixture with the nanoscale electronic elements, the sequencing reaction mixture comprising a plurality of types of nucleotide analogs, each type having a different impedance label, wherein the impedance labels are sensed by the nanoscale electronic elements while an analog is associated with the polymerase enzyme complex; an electronic control system electrically connected to the nanoscale electronic elements through the electrical connections to apply desired electrical signals to the nanoscale electronic elements and for receiving electrical signals from the nanoscale electronic elements; and a computer that receives information on the electrical signals at the nanoscale electronic elements over time and uses such information to identify a sequence of the template nucleic acid.

In some aspects, the invention provides a method for nucleic acid sequencing comprising: providing a substrate comprising a nanoscale electrode, the substrate comprising a polymerase enzyme complex comprising a polymerase enzyme and a template nucleic acid, the complex attached to the nanoscale electrode or to the substrate proximate to the nanoscale electrode; exposing the polymerase to a plurality of types of nucleotide analogs, each comprising a different capacitive label attached to the phosphate portion of the nucleotide analog under conditions whereby polymerase mediated nucleic acid synthesis occurs, resulting in cleavage of the capacitive label and the growth of a nascent nucleic acid strand; applying electrical signals comprising alternating current over time to the nanoscale electrode, whereby when a nucleotide analog resides in the active site of the enzyme, the capacitive label on the nucleotide analog produces a measurable change in the capacitance at the nanoscale electrodes; monitoring the electrical signal at the nanoscale electrode over time, whereby the electrical signal indicates an incorporation event for a type of nucleotide analog having a specific capacitive label; and using the monitored electrical signal at the electrode over time to determine a sequence of the template nucleic acid.

In some embodiments the nanoscale electrode is repeatedly addressed at different frequencies, whereby the capacitance measured at each frequency is used to identify a specific capacitive label. In some embodiments the polymerase is exposed to four types of nucleotide analogs corresponding to A, G, C, T, or A, G, C, U, wherein the frequency of the nanoscale electrode is repeatedly addressed at least 8 different frequencies. In some embodiments the electrical signals applied to the electrode comprise sine waves, triangular waves, or saw tooth waves.

In some embodiments an amount of change in capacitance over time is used to identify which type of nucleotide is incorporated. In some embodiments the characteristics of capacitance versus frequency is used to identify which type of nucleotide is incorporated. In some embodiments the characteristics of in capacitance over time is used to identify which type of nucleotide is incorporated.

In some embodiments the enzyme is attached to the nanoscale capacitive electrode. In some embodiments the capacitive label is attached to the polyphosphate portion through a linker.

In some aspects, the invention provides a method for nucleic acid sequencing comprising: providing a substrate comprising at least two nanoscale electrodes, the substrate comprising a polymerase enzyme complex comprising a polymerase enzyme and a template nucleic acid, the complex attached to the substrate proximate to the electrodes; exposing the polymerase to a plurality of types of nucleotide analogs each comprising a different capacitive label attached to the phosphate portion of the nucleotide analog under conditions whereby polymerase mediated nucleic acid synthesis occurs, resulting in cleavage of the capacitive label and the growth of a nascent nucleic acid strand; applying electrical signals comprising alternating currents over time at the nanoscale electrodes, whereby when a nucleotide analog resides in the active site of the enzyme, the capacitive label on the nucleotide analog produces a measurable change in the capacitance at the nanoscale electrodes; monitoring the electrical signal at the nanoscale electrodes over time, whereby the electrical signal indicates an incorporation event for a type of nucleotide analog having a specific capacitive label; and using the monitored electrical signal at the electrodes over time to determine a sequence of the template nucleic acid.

In some embodiments the frequency of the alternating current at the nanoscale electrodes is repeatedly brought to different frequency levels, whereby a characteristic capacitance versus frequency profile is used to identify a specific capacitive label. In some embodiments the alternating current applied to the electrodes comprises sine waves, triangular waves or a saw tooth waves. In some embodiments the polymerase is exposed to four types of nucleotide analogs, corresponding to A, G, C, T, or A, G, C, U, wherein the alternating current at the nanoscale electrodes are repeatedly brought to at least 4 different frequency levels.

In some embodiments the level of capacitance over time is used to identify which type of nucleotide is incorporated. In some embodiments the characteristics of the capacitance over time is used to identify which type of nucleotide is incorporated. In some embodiments the characteristic of the capacitance over time includes the capacitance oscillation color. In some embodiments the enzyme is attached to the substrate between the electrodes.

In some embodiments the plurality of types of nucleotide analogs comprises four differently labeled nucleotide analogs 1, 2, 3, and 4, wherein nucleotide analogs 1 and 2 each comprise a capacitive label with a first type of capacitive moiety, and nucleotide analogs 3 and 4 each comprise capacitive label with a second type of capacitive moiety, wherein nucleotide 1 has a different number of capacitive moieties than nucleotide analog 2, and nucleotide 3 has a different number of capacitive moieties than nucleotide analog 4. In some embodiments the capacitive label is attached to the polyphosphate portion through a linker.

In some aspects, the invention provides a chip for sequencing a plurality of single nucleic acid template molecules comprising: a substrate comprising; a plurality of capacitive devices, each capacitive device comprising at least one nanoscale electrode and a single polymerase enzyme complex bound to the substrate proximate to the nanoscale electrode, wherein the polymerase enzyme complex comprises a polymerase enzyme and a template nucleic acid; wherein the substrate is configured such that the capacitive device comes into contact with a sequencing reaction mixture comprising a plurality of types of nucleotide analogs each having different capacitive labels; and a plurality of electrical connection sites for bringing current and voltage to the capacitive devices, and for receiving electrical signals from the devices.

In some embodiments the substrate comprises greater than 1,000 capacitive devices. In some embodiments the substrate comprises greater than 10,000 capacitive devices. In some embodiments the substrate comprises about 1,000 capacitive devices to about 10 million capacitive devices. In some embodiments the substrate comprises about 10,000 capacitive devices to about 1 million capacitive devices.

In some embodiments each nanoscale electrode is electrically connected to an electrical interconnection through which the electrode is brought to the frequencies and through which the capacitance is measured. In some embodiments the substrate comprises electronic elements for one or more of: providing alternating current to the nanoscale electrodes, measuring the capacitance at the nanoscale electrodes, analog to digital conversion, signal processing, and data storage. In some embodiments the electrical elements are CMOS elements. In some embodiments the substrate comprises a plurality of counter-electrodes. In some embodiments there is one counter-electrode for each nanoscale capacitive device.

In some aspects, the invention provides a system for sequencing a template nucleic acid comprising: a housing having housing electrical connection sites; a chip that reversibly mates with the housing comprising a substrate comprising; chip electrical connection sites that reversibly connect to the housing electrical connection sites; a plurality of capacitive devices, each capacitive device comprising at least one nanoscale electrode and a single polymerase enzyme complex bound to the at least one nanoscale electrode or to the substrate proximate to the at least one nanoscale electrode, wherein the polymerase enzyme complex comprises a polymerase enzyme and a template nucleic acid; a fluid reservoir for contacting a sequencing reaction mixture with the capacitive devices, the sequencing reaction mixture comprising a plurality of types of nucleotide analogs, each having a different capacitive label, wherein the capacitive labels are sensed while an analog is associated with the polymerase enzyme complex; an electronic control system electrically connected to the nanoscale electrodes through the electrical connections to apply desired alternating currents to the nanoscale electrodes and for determining the current to and from the nanoscale electrodes; and a computer that receives information on the capacitance at the nanoscale electrodes over time and uses such information to identify a sequence of the template nucleic acid.

In some embodiments the substrate comprises greater than 1,000 capacitive devices. In some embodiments the substrate comprises greater than 10,000 capacitive devices. In some embodiments the substrate comprises about 1,000 capacitive devices to about 10 million capacitive devices. In some embodiments the substrate comprises about 10,000 capacitive devices to about 1 million capacitive devices.

In some embodiments each nanoscale electrode is electrically connected to an electrical interconnection through which the electrode is brought to the appropriate frequencies and through which the capacitance is measured. In some embodiments the substrate comprises electronic elements for one or more of: providing alternating current to the nanoscale electrodes, measuring the capacitance at the nanoscale electrodes, analog to digital conversion, signal processing, and data storage. In some embodiments the electrical elements are CMOS elements. In some embodiments the substrate comprises a plurality of counter-electrodes. In some embodiments there is one counter-electrode for each nanoscale capacitive device.

In some aspects, the invention provides a method for nucleic acid sequencing comprising: providing a substrate comprising an array of nanoFETs, each comprising a source, a drain, and a gate, wherein a plurality of the nanoFETs comprise a single polymerase enzyme complex comprising a polymerase enzyme and a template nucleic acid, the complex attached to gate of the nanoFET or to the substrate proximate to the gate of the nanoFET; exposing the substrate to a plurality of types of nucleotide analogs, each comprising a different conductivity label attached to the phosphate portion of the nucleotide analog under conditions whereby polymerase mediated nucleic acid synthesis occurs, resulting in cleavage of the conductivity label and the growth of a nascent nucleic acid strand; applying a voltage between the source and drain, whereby when a nucleotide analog resides in the active site of the enzyme, the conductivity label on the nucleotide analog produces a measurable change in the conductivity of the gate; monitoring an electrical signal comprising the current and voltage at the nanoFET over time, whereby the electrical signal indicates an incorporation event for a type of nucleotide analog having a specific conductivity label; and using the electrical signal to determine a sequence of the template nucleic acid.

In some embodiments the electrical signal used to determine the sequence of the template nucleic acids includes the duration of the signal indicating the residence time of a nucleotide analog in the active site of a polymerase. In some embodiments the gate of the nanoFET comprises a nanowire. In some embodiments the gate of the nanoFET comprises doped silicon.

In some embodiments the voltage across the source and drain is DC. In some embodiments the voltage across the source and drain is AC, and the frequency of the AC voltage is changed with time. In some embodiments the substrate is exposed to four types of nucleotide analogs corresponding to A, G, C, T, or A, G, C, U, each of the four types of nucleotide analogs having a different conductivity label.

In some embodiments the capacitive label is attached to the polyphosphate portion through a linker.

In some aspects, the invention provides a chip for sequencing a plurality of single nucleic acid template molecules comprising: a substrate comprising; a plurality of nanoFET devices, each nanoFET device comprising a source, a drain and a gate and a single polymerase enzyme complex bound to the gate or to the substrate proximate to the gate of the nanoFET, wherein the polymerase enzyme complex comprises a polymerase enzyme and a template nucleic acid; wherein the substrate is configured such that the nanoFET device comes into contact with a sequencing reaction mixture comprising a plurality of types of nucleotide analogs each having different conductivity labels; and a plurality of electrical connection sites for bringing current and voltage to the nanoFETs, and for receiving electrical signals from the nanoFETs.

In some embodiments the gate of the nanoFET comprises a nanowire. In some embodiments the gate of then nanoFET comprises a doped silicon.

In some embodiments the substrate comprises greater than 1,000 nanoFET devices. In some embodiments the substrate comprises greater than 10,000 nanoFET devices. In some embodiments the substrate comprises about 1,000 nanoFET devices to about 10 million nanoFET devices. In some embodiments the substrate comprises about 10,000 nanoFET devices to about 1 million nanoFET devices.

In some embodiments the substrate comprises electronic elements for one or more of: providing electrical signals to the nanoFETs, measuring the electrical signals at the nanoFETs, analog to digital conversion, signal processing, and data storage. In some embodiments the electrical elements are CMOS elements.

In some aspects, the invention provides a system for sequencing template nucleic acids comprising: a housing having housing electrical connection sites; a chip that reversibly mates with the housing comprising a substrate comprising; chip electrical connection sites that reversibly connect to the housing electrical connection sites; a plurality of nanoFET devices, each nanoFET device comprising a source, a drain, and a gate, and a single polymerase enzyme complex bound the gate or bound to the substrate proximate to the gate, wherein the polymerase enzyme complex comprises a polymerase enzyme and a template nucleic acid; a fluid reservoir for contacting a sequencing reaction mixture with the nanoFET devices, the sequencing reaction mixture comprising a plurality of types of nucleotide analogs, each having a different conductivity label, wherein the conductivity labels are sensed by the nanoFET while an analog is associated with the polymerase enzyme complex; an electronic control system electrically connected to the nanoFET devices through the electrical connections to apply desired electrical signals to the nanoscale electrodes and for receiving electrical signals from the nanoFET devices; and a computer that receives information on the electrical signals at the nanoscale electrodes over time and uses such information to identify a sequence of the template nucleic acid.

In some embodiments the gate of the nanoFET comprises a nanowire. In some embodiments the gate of the nanoFET comprises doped silicon.

In some embodiments the substrate comprises greater than 1,000 nanoFET devices. In some embodiments the substrate comprises greater than 10,000 nanoFET devices. In some embodiments the substrate comprises about 1,000 nanoFET devices to about 10 million nanoFET devices. In some embodiments the substrate comprises about 10,000 nanoFET devices to about 1 million nanoFET devices.

In some embodiments the substrate comprises electronic elements for one or more of: providing electrical signals to the nanoFET devices, measuring the electrical signals at the nanoFET devices, analog to digital conversion, signal processing, and data storage. In some embodiments the electrical elements are CMOS elements.

BRIEF DESCRIPTION OF THE DRAWINGS

FIG. 1(A) shows the polymerase-template complex attached to an electrode and a labeled nucleotide analog in a sequencing reaction mixture. FIG. 1(B) shows the nucleotide analog held in the active site of the polymerase enzyme. FIG. 1(C) shows that when nucleotide analog is incorporated into the growing strand, the enzyme cleaves the labeled polyphosphate portion of the nucleotide analog.

FIG. 2(A) shows the polymerase-template complex bound proximate to two nanoscale electrodes and a labeled nucleotide analog in a sequencing reaction mixture. FIG. 2(B) shows the nucleotide analog held in the active site of the polymerase enzyme. FIG. 2(C) shows that when nucleotide analog is incorporated into the growing strand, the enzyme cleaves the labeled polyphosphate portion of the nucleotide analog.

FIG. 4(A) shows a two electrode configuration with linear electrodes. FIG. 4(B) shows a two electrode configuration where the enzyme is attached to an insulating layer between walls of electrode. FIG. 4(C) shows a split circular electrode with an insulating strip in the middle to which the enzyme is attached. FIG. 4(D) shows a circularly symmetric single electrode configuration where the enzyme complex is attached to the electrode. FIG. 4(E) shows a circularly symmetric single electrode configuration in which the enzyme complex is attached to a middle insulating region. FIG. 4(F) shows a single electrode linear electrode configuration on a flat insulating surface.

FIG. 5(A) illustrates an array of a linear two electrode configuration capacitive devices.

FIGS. 6(A)-(C) show three possible structures for forming a single electrode capacitive device of the invention. In FIG. 6(A) a substrate has electrical trace that connects with an electrode. An insulating layer is deposited on top of the electrode to create a well. In FIG. 6(B) A planarization layer is deposited to produce an electrode configuration flush with the surface to which the enzyme complex is attached. In FIG. 6(C) an electrode is on top of the substrate and connected by a via.

FIGS. 7(A)-(E) show an exemplary process for producing a two electrode capacitive device of the invention and FIG. 7(F) shows an alternate embodiment. FIG. 7(A) shows a patterned metal electrode on a substrate such as a silicon substrate. FIG. 7(B) shows the result of step I in which an insulating layer is deposited, patterned, and etched such that the bottom electrode is covered. FIG. 7(C) shows the result of step II in which a top electrode layer is deposited on top of the insulating layer, with the electrode extending off to produce an electrical interconnect. FIG. 7(D) shows the result of step III in which a second insulating layer is deposited over the top electrode layer. FIG. 7(E) shows the result of step IV in which a notch is etched into the electrode insulator stack to expose a portion of the top and bottom electrode and insulating layer. FIG. 7(F) shows an alternative to the final device in which the electrode layers are angled with respect to one another.

FIG. 8(A) shows the polymerase-template complex attached to nanowire of a nanoFET and a nucleotide analog having a conductivity label in a sequencing reaction mixture. FIG. 8(B) shows the nucleotide analog held in the active site of the polymerase enzyme. FIG. 8(C) shows that when nucleotide analog is incorporated into the growing strand, the enzyme cleaves the polyphosphate portion of the nucleotide analog.

DETAILED DESCRIPTION OF THE INVENTION

Figure 1:
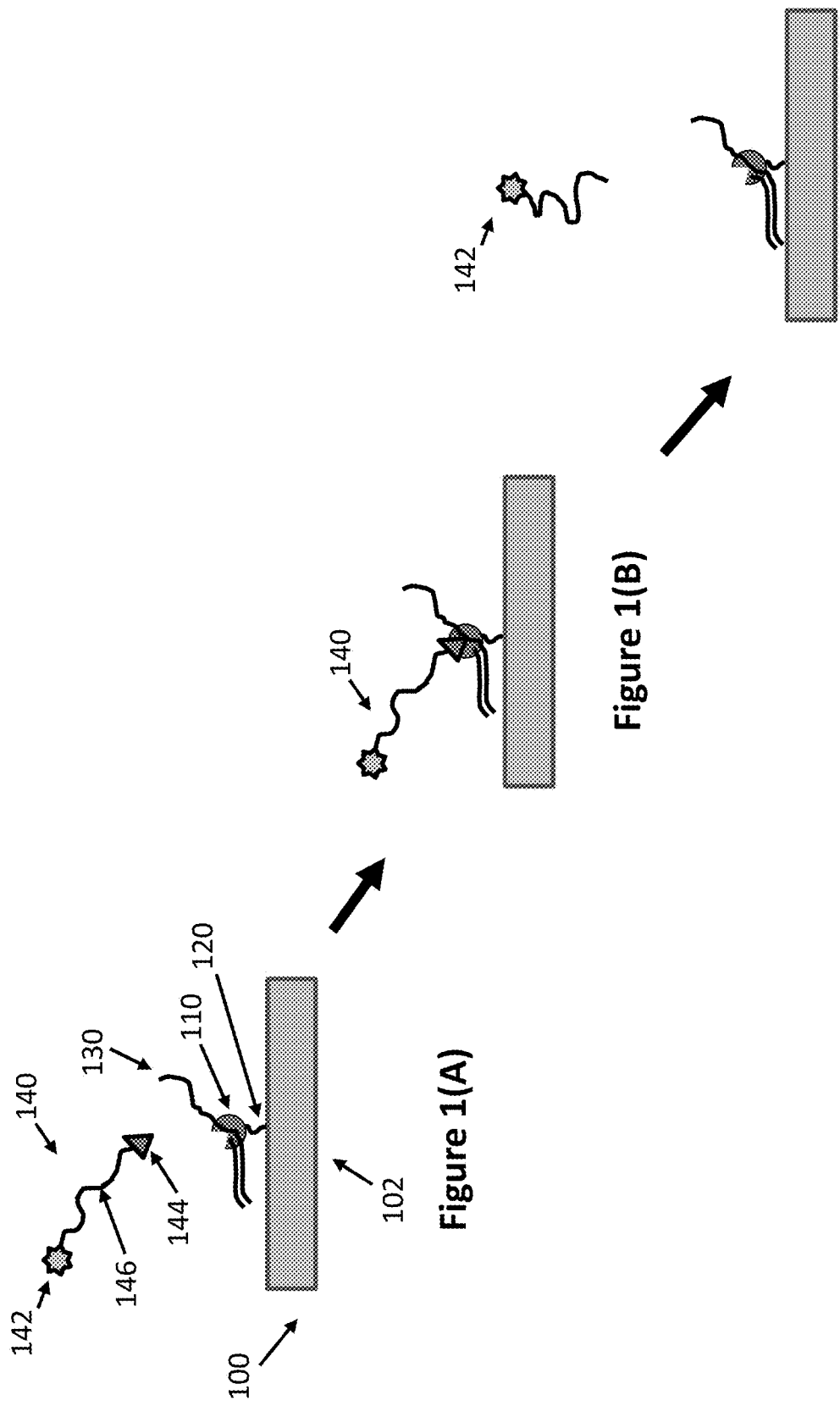
FIGS. 1(A)-(C) show an embodiment of the invention in which single molecule sequencing is carried out using a nanoscale capacitive device with a single nanoscale electrode.

In some aspects, the invention provides methods, devices, systems, and compositions of matter directed to single molecule real time electronic sequencing. The electronic detection can performed using with impedance, capacitance, or conductivity. In some aspects, single polymerase-template complex is immobilized proximate to one or two nanoscale electrodes, and the incorporation of nucleotides by the polymerase enzyme is monitored by measuring the change in impedance, capacitance, or conductivity at the nanoscale electrode or electrodes due to a label on a nucleotide analog while it is held in the active site of the enzyme during incorporation. The invention utilizes arrays of nanoscale electronic elements capable of detecting signals at the single molecule level. In some aspects a single polymerase-template complex is immobilized proximate to a the gate of a nanoFET device, and the electrical signal from the nanoFET is used for determining a nucleic acid sequence. In some aspects, nanoscale electrodes are used for measuring changes of capacitance at the single-molecule level. Having electrodes on the nanometer scale allows for obtaining adequate signal to noise at the single molecule level.

Typically four nucleotide analogs, each having a different distinguishable capacitive or conductivity label, are present. The capacitive or conductivity label is connected to the analog through the phosphate portion of the nucleotide analog such that when the nucleotide analog is incorporated by the polymerase enzyme into the growing strand, the label is released. The capacitive or conductivity label is typically connected to the nucleotide portion of the analog through a linker. When the nucleotide analog is held in the polymerase enzyme active site the capacitive label produces a change in capacitance at the nanoscale electrode, or the conductivity label produces a change in conductivity of the gate of a nanoFET. The change in capacitance or conductivity can be used to determine the presence and the identity of the nucleotide analog that is in the active site. The characteristics of the capacitance while the nucleotide is in the active site will be different than the characteristics of a nucleotide that freely diffuses near the electrode. Because the nucleotide is held close to the electrodes or gate during the incorporation process by the enzyme, it is held in place long enough for its characteristic capacitance change to be determined in order to identify which type of nucleotide is incorporated.

The instant invention relates to single molecule sequencing that does not require reduction or oxidation (redox) of labels on the nucleotides or nucleotide analogs. The use of capacitance, impedance, or conductivity changes has a number of advantages over using redox labels. One advantage is that the labels in the instant invention can be less reactive than the labels in a redox based method. In order for a redox based method to sense a label, one or more electrons must be exchanged between the label and the electrode, resulting in reduction or oxidation of the label. These types of reactions can produce products or intermediates such as radicals, radical anions, or radical cations that are can be reactive and unstable. In the instant application, the capacitive, impedance, or conductivity labels can influence the electrical properties of components on a chip without the exchange of electrons. In addition, it can be more straightforward to provide multiple (e.g. four) different labels using capacitance, impedance, or conductivity than it is to do so using redox chemistry, e.g. distinguishing four labels with different oxidation or reduction potentials.

Where a capacitive device is used as the nanoscale electronic element, capacitance can be determined by measuring the impedance at the electrode while AC current is applied to the electrode. The frequency of the current applied to the single nanoelectrode or pair of nano-electrodes is typically varied over time in a manner that allows for the identification of the nucleotide analog in the active site using capacitive labels, for example having different impedance versus frequency characteristics. Base calling software is then employed to call bases by correlating the impedance or capacitance over time at the relevant voltage with the expected characteristics of the capacitive labels. The called bases can be used to identify the sequence of the template nucleic acid whose sequence is complementary to that of the added bases. The methods of the invention utilize the characteristic that a nucleotide analog which is incorporated into a growing nucleic acid chain spends more time in the active site of the enzyme and therefore spends more time proximate to the electrode than do non-cognate nucleotides that are not incorporated or freely diffusing nucleotides passing near the electrode. Thus, the residence time can be used as a characteristic to distinguish incorporated nucleotides from freely diffusing nucleotides in solution.

Chips having arrays of nanoscale electronic elements comprising nanoscale electrode capacitance devices and nanoFET devices are described. Each device performs a sequencing reaction in real time, allowing for hundreds, thousands, millions, or more sequencing reactions to be monitored simultaneously. The nanoscale electrodes used in the capacitive devices are typically constructed to have a small size, and therefore to give low levels of capacitance noise. This allows for rapid transfer of current for capacitance measurements of events which typically occur on the microsecond to millisecond timescale. The chips can be prepared using known semiconductor processing techniques, for example on a silicon substrate. The nanoscale electrodes in the array have a polymerase enzyme-template complex attached to the electrodes or attached proximate to the electrodes. The polymerase-template complex is close enough to the nanoscale electrode that a capacitive label on a nucleotide analog can be detected when the nucleotide analog is associated with the polymerase enzyme in the complex.

Systems for carrying out sequencing are described. The capacitive or nanoFET sequencing chips of the invention mate with a socket that holds the chip in place and provides electrical connections to interconnects on the chips for transferring electrical signals to and from the nanoscale electrodes. A current/voltage source provides the current and voltage to bring the nanoscale electrodes to the potential and in some cases the desired AC frequencies as a function of time. An impedance measurement device or a nanoFET is used to determine the electrical signal changes associated with the presence of the capacitive or conductivity labels.

The system includes a fluid reservoir for holding the sequencing reagents in contact with the nanoscale electrodes on the chip. The fluid reservoir can be, for example, a microfluidic chamber or a well. The system will also have either a counter electrode, a reference electrode or both in contact with the fluid. The counter electrode and or the reference electrode can be incorporated into the chip or can be separate from the chip, and in contact with the liquid sample. In the fluid reservoir is a sequencing reaction mixture that allows a single polymerase enzyme proximate to the nanoscale electrodes to perform nucleic acid synthesis. The sequencing reaction mixture has nucleotide analogs with capacitive labels or conductivity labels that are cleaved when the nucleotide is incorporated into the growing nucleic acid strand. The enzyme is proximate to the nanoscale electrode or electrodes or gates such that when a nucleotide analog is associated with the polymerase enzyme on its way to incorporation into the growing chain, the capacitive or conductivity label on the nucleotide analog changes the capacitance or conductivity in the region of the nanoscale electrode or gate. A voltage/current source can be used to vary an AC signal at the nanoscale electrodes over time. A current meter can be used to measure the level of current flow and the impedance. The measurement of a change in capacitance, impedance or conductivity indicates the presence of a capacitive label on the nucleotide analog held within the enzyme. A computer monitors the measured current over time at the current meter, and uses this information to determine the sequence of nucleotide incorporation. The capacitance signal or conductivity signal indicates that the nucleotide corresponding to that label is being incorporated into the growing strand. By measuring a time sequence of incorporation, the sequence of the growing strand, and thereby the sequence of the corresponding template nucleic acid, is ascertained.

In some cases the nanoscale electronic element comprises a single nanoscale electrode which is used to perform nucleic acid sequencing by measuring the presence of a capacitive labeled nucleotide analog within the enzyme complex. FIG. 1 provides a schematic representation of a method for real time nucleic acid sequencing with one nanoscale electrode and a polymerase-template complex bound to or proximate to the nanoscale electrode. A substrate 100 has a region on its surface with nanoscale electrode 102. Onto the electrode 102 is attached a polymerase enzyme complex comprising a polymerase enzyme 110 and a nucleic acid template 130. The complex is typically primed, for example with an oligonucleotide primer. The complex is attached to the electrode 102 by an attachment moiety 120. In some cases the polymerase is not attached to the electrode 102, but is attached to the substrate proximate to the electrode or to an insulating region on top of the electrode. The attachment must be close enough to the electrode that when a nucleotide analog is associated with the enzyme, the capacitive label can be detected. As shown in FIG. 1, the polymerase enzyme is attached to the surface of the electrode. In some cases, the template nucleic acid is attached to the surface, either directly, or through hybridization with a primer attached to the surface.

The substrate comprising the nanoscale electrode is contacted with a fluid comprising a sequencing reaction mixture. The sequencing reaction mixture has the reagents required for carrying out polymerase mediated nucleic acid synthesis. The sequencing reaction mixture will generally include Mn++ or Mg++ salts for activating the enzyme, as well as other salts such as Na+ or K+ for providing the appropriate ionic strength. These salts also can also be used to adjust the background impedance at the electrode. In some cases the type and amount of ions in solutions is adjusted for optimum solution impedance. The sequencing reaction mixture also contains capacitive labeled nucleotide analogs such as labeled nucleotide analog 140. In FIG. 1, nucleotide analog 140 is a cognate nucleotide having a base that is complementary to the next position in the template nucleic acid 130. The nucleotide analog 140 has a nucleotide portion 144 comprising a nucleobase, a sugar, and a polyphosphate portion. The nucleotide analog 140 has a capacitive label 142 that is attached to the polyphosphate portion of the nucleotide portion 144 through linker 146.

In FIG. 1(B) the nucleotide analog 140 is held in the active site of the polymerase enzyme 110. Because it is a cognate nucleotide, it is recognized by the enzyme as such, and will be held in the enzyme longer than will a non-cognate nucleotide. At the time that the nucleotide analog 140 is associated, the electrode 102 is being addressed with alternating current. In some cases, the electrode is being cycled through a series of frequencies, either continuously or in steps. The label 142 causes the capacitance in as measured at the electrode to change, allowing its presence and its identity to be determined.

As shown in FIG. 1(C) when the nucleotide analog 140 is incorporated into the growing strand, the enzyme cleaves the polyphosphate portion of the nucleotide analog. This cleavage occurs between the alpha and beta phosphates, releasing the portion of the nucleotide analog comprising the label 142, which diffuses away from the substrate. The cleavage and diffusion away of the label ends the period in which the capacitance at the electrode is affected by the presence of the label. The change in capacitance, then, provides a measure of the residence time of the nucleotide analog in the active site prior to incorporation, which can be used to determine that nucleotide incorporation has occurred.

Figure 2:
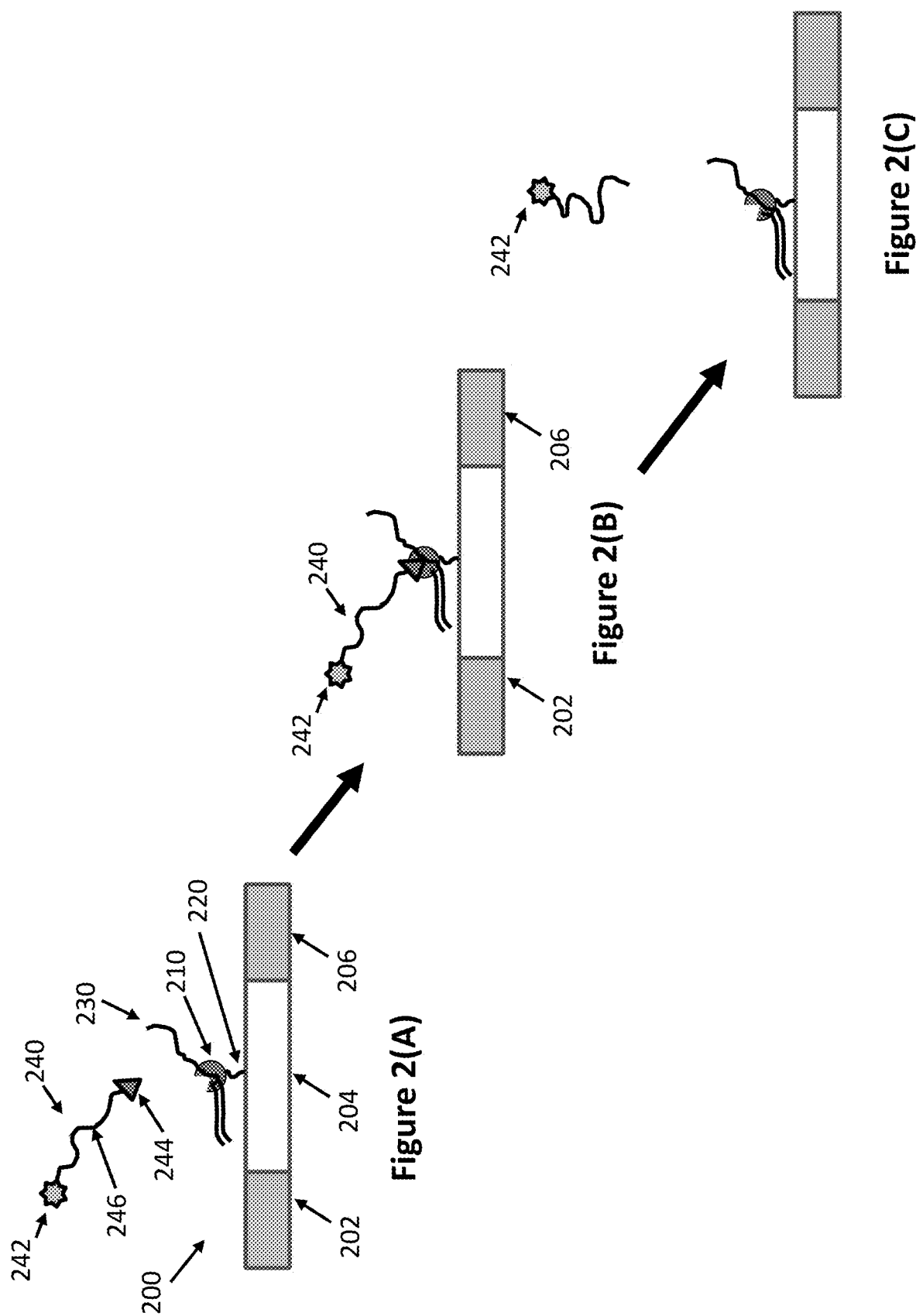
FIGS. 2(A)-(C) show an embodiment of the invention in which single molecule sequencing is carried out using a nanoscale capacitive device with two nanoscale electrodes.

In some cases two nanoscale electrodes are used to perform nucleic acid sequencing by measuring the presence of the labeled nucleotide analog within the enzyme complex. FIG. 2 provides a schematic representation of a method for real time nucleic acid sequencing with two nanoscale electrodes and a polymerase-template complex bound proximate to the nanoscale electrodes. A substrate 200 has a region on its surface with two nanoscale electrodes 202 and 206 separated on the order of nanometers. The separation can be from 1 nm to 100 nm, or from 2 nm to 20 nm. Here, an insulating region 204 between the electrodes provides separation. Onto the insulating region 204 between the electrodes is attached a polymerase enzyme complex comprising a polymerase enzyme 210 and a nucleic acid template 230. The complex is attached to the insulation region 204 by an attachment moiety 220. As shown in FIG. 2, the polymerase enzyme is attached to the surface. In some cases, the template nucleic acid can be attached to the surface, either directly, or through hybridization with a primer attached to the surface. In the figure, the nanoscale electrodes are shown as disposed on a horizontal surface. In some cases, the electrodes are disposed vertically, e.g. as a stack of layers. A vertical construction can be useful for producing the required nanoscale insulating region 204 between the electrodes.

The substrate comprising the nanoscale electrodes is contacted with a fluid comprising a sequencing reaction mixture. The sequencing reaction mixture has the reagents required for carrying out polymerase mediated nucleic acid synthesis. The sequencing reaction mixture will generally include Mn++ or Mg++ salts for activating the enzyme, as well as other salts such as Na+ or K+ for providing the appropriate ionic strength. These salts can also be used to adjust the background capacitance at the electrodes. The sequencing reaction mixture also contains capacitive labeled nucleotide analogs such as labeled nucleotide analog 240. In FIG. 2, nucleotide analog 240 is a cognate nucleotide having a base that is complementary to the next position in the template nucleic acid 230. The nucleotide analog 240 has a nucleotide portion comprising a nucleobase, a sugar, and a polyphosphate portion 244. The nucleotide analog 240 has a capacitive label 242 that is attached to the polyphosphate portion of the nucleotide portion 244 through linker 246.

In FIG. 2(B) the nucleotide analog 240 is held in the active site of the polymerase enzyme 210. Because it is a cognate nucleotide, it is recognized by the enzyme as such, and will be held in the enzyme longer than will a non-cognate nucleotide. At the time that the nucleotide analog 240 is associated, its presence will be detected at electrodes 202 and 206. Electrodes 202 and 206 are addressed with alternating current. In some cases, the electrodes are cycled through a series of frequencies, either continuously or in steps. The label 242 causes the capacitance in as measured at the electrodes to change, allowing its presence and its identity to be determined.

When the nucleotide analog 240 is incorporated into the growing strand as shown in FIG. 2(C), the polymerase enzyme cleaves the polyphosphate portion of the nucleotide analog. This cleavage occurs between the alpha and beta phosphates in the polyphosphate portion which releases the portion of the nucleotide analog comprising the label 242, which diffuses away from the substrate. This cleavage and diffusion away of the label ends the period in which the capacitance at the electrode is affected by the presence of the label. The change in capacitance, then, provides a measure of the residence time of the nucleotide analog in the active site prior to incorporation, which can be used to determine that nucleotide incorporation has occurred.

The paragraphs above describe the detection of one type of nucleotide analog. This approach is also used for the measurement of the incorporation of more than one type of analog, for example 2, 3, 4, 5 or more types of analogs. For example, typically four different types nucleotide analogs corresponding to either A, G, C, T, for DNA or A, G, C, U for RNA are used. Each of the four types of nucleotide analog has different and distinguishable capacitance characteristics, e.g. four different capacitive labels. The different types of nucleotide analogs can have different capacitance, different capacitance versus frequency characteristics, or can have other distinguishable electrical characteristics such as different current oscillation color or can have combinations of the above.

Figure 3:
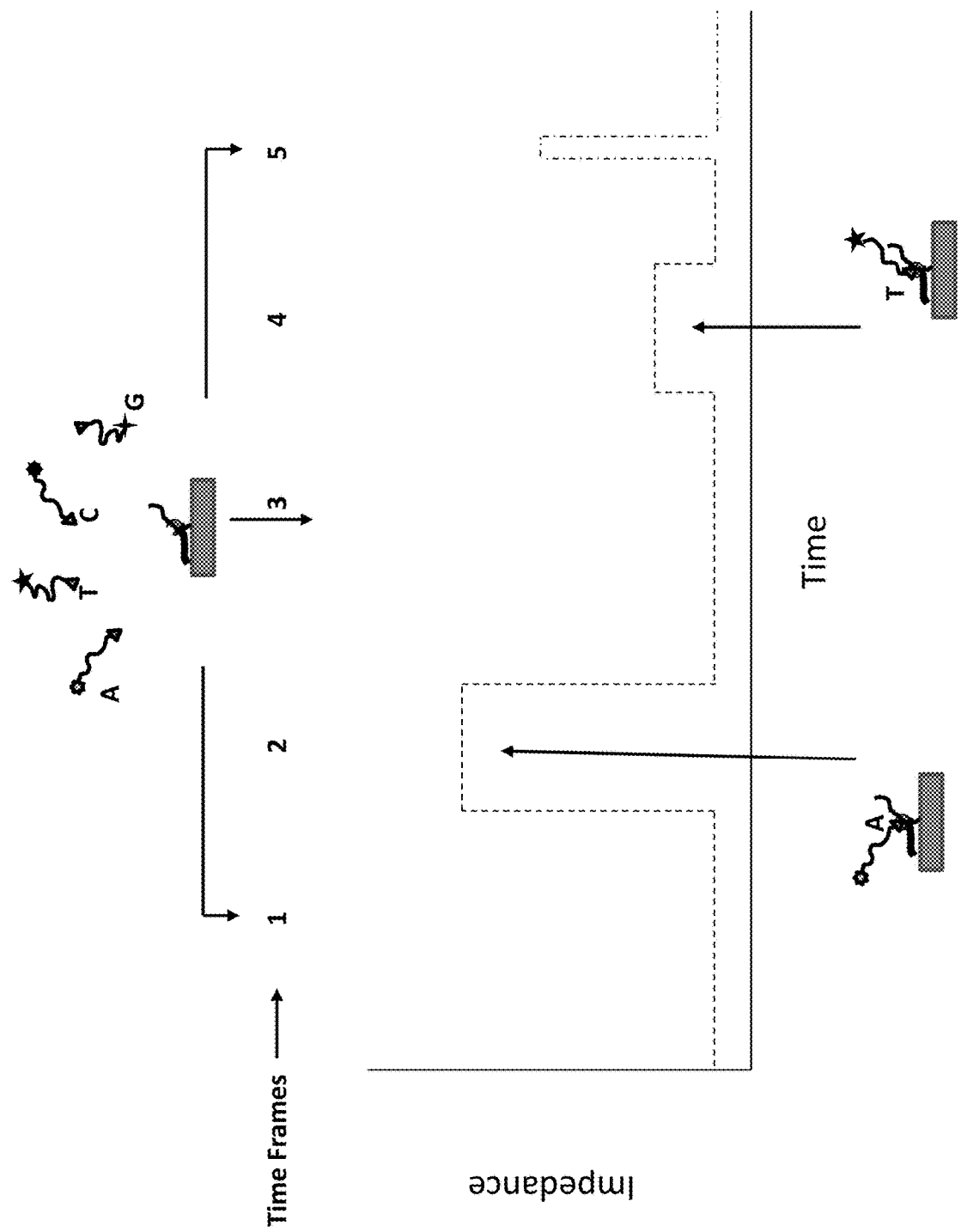
FIG. 3 illustrates the sequencing method, showing how changes in capacitance versus time can be used to identify incorporated nucleotide analogs.
Figure 4A:
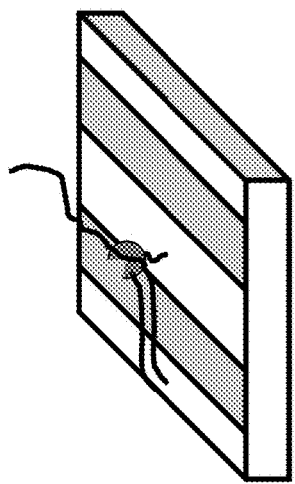
FIGS. 4(A)-(F) show some potential embodiments for two electrode and one electrode configurations of capacitive devices.
Figure 4B:
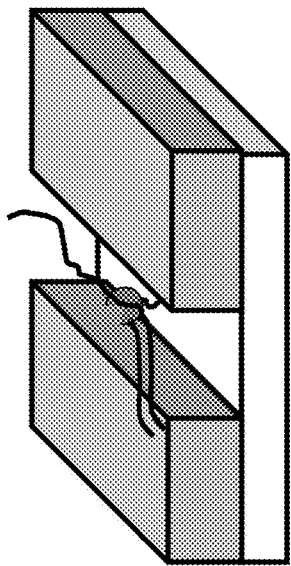
Figure 4C:
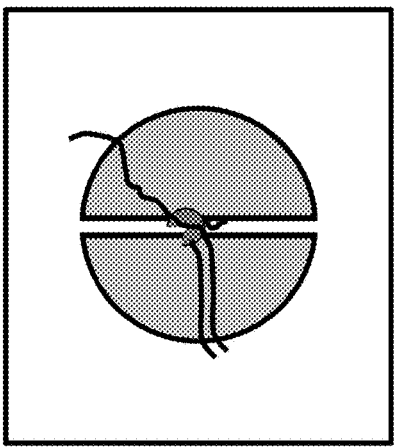
Figure 4D:
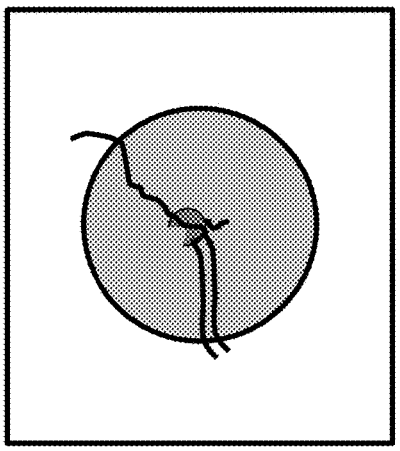
Figure 4E:
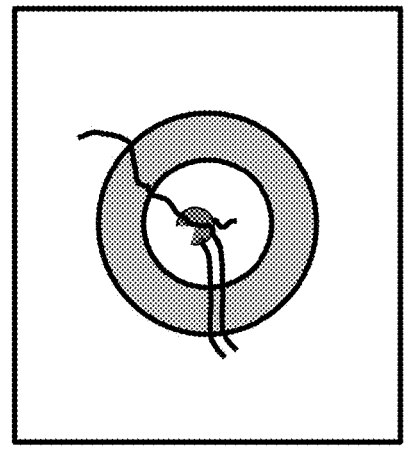
Figure 4F:
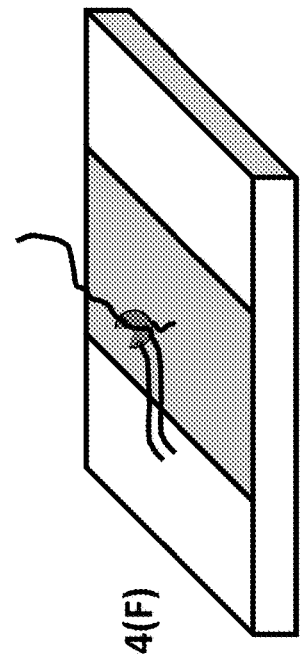

FIG. 3 shows how the invention can be used to call a series of bases for sequencing using changes in impedance. A graph is shown indicating the impedance signal that is detected. A one electrode system as described above is used. The same approach described here can be used to sequence using a two electrode configuration for capacitance or with a other nanoscale electronic elements such as nanoFET devices. While the method is described with respect to capacitance, the method can similarly be used with conductivity or more generally using impedance. In FIG. 3 there are four types of nucleotide analogs, each having a different capacitive label, for example, each with a different magnitude of capacitance change when in the vicinity of the electrode. For the approach illustrated here, the frequency of the current at the electrode is kept the same throughout the experiment, and the impedance at that frequency is monitored over time.

The method is described in FIG. 3 by referring to 5 different time frames. During time frame 1, none of the four nucleotide analogs is associated with the polymerase enzyme, and therefore none of the four voltage states detects an appreciable amount of change in impedance from the baseline. In time frame 2, a nucleotide analog corresponding to nucleobase A is in the active site for a time that is characteristic of incorporation (e.g. about 10 msec to about 500 msec). During the time the nucleotide analog is in the active site, the measured impedance rises to a level characteristic of the label on that nucleotide analog. This level of impedance for a residence time corresponding to incorporation indicates the incorporation of A. When the nucleotide is incorporated, the capacitive label is cleaved and the impedance signal returns to baseline. In time frame 3, again none of the four channels detects an appreciable change in impedance indicating that no nucleotide analog is in the active site of the polymerase. During time frame 4, a nucleotide analog corresponding to T is incorporated and is held within the active site for a time period characteristic of incorporation. During the time it is held within the enzyme, an impedance characteristic of the label on the nucleotide analog corresponding to T is seen.

When the analog is incorporated, the label is cleaved, and diffuses away and the impedance again returns to baseline. In time frame 5 for a short time, an increase in impedance (to a level consistent with the label corresponding G) is detected. The time of the increased impedance is too short to be likely to correspond to an incorporation event. This type of feature can be seen, for example, where a non-cognate nucleotide is sampling the active site, after which it diffuses from the enzyme. During the time of the portion of the experiment shown in FIG. 3, the data indicate that an A and a T were incorporated, which thus indicates that there is a T and an A in the complementary sequence of the template. While this description relates to the incorporation of two nucleotides, this method can be used to sequence long stretches of nucleic acids from hundreds to tens of thousands of bases or more.

The example of FIG. 3 is carried out with four nucleotides, each having a capacitive label that exhibits a different magnitude in impedance. It will be understood that the same approach described in FIG. 3 can be applied to cases in which impedance versus time (dielectric spectrum) or current oscillation color or any combination of the three is used to identify the incorporated bases.

In some aspects, the invention provides a method of sequencing a template nucleic acid comprising: disposing a polymerase enzyme complex comprising a polymerase enzyme, a template, and a primer proximate to a nanoscale electrode; exposing the polymerase to a solution comprising the components required for carrying out polymerase mediated nucleic acid synthesis, the solution including a plurality of nucleotide analogs, each nucleotide analog having a different capacitive label, each capacitive label attached to the phosphate portion of the nucleotide analog so as to be cleaved and released upon incorporation of the nucleotide analog into a growing nucleic acid strand; measuring an electrical signal from an impedance measuring system comprising the nanoscale electrode, optionally a counter electrode, and optionally a reference electrode to determine the presence and identity of a nucleotide analog in the active site of an enzyme by its capacitive label; and monitoring the electrical signal over time to determine a sequence of the template nucleic acid.

Arrays of Nanoscale Electrode Capacitive Devices

Some aspects of the invention provide arrays of devices for carrying out real time capacitive sequencing. The arrays of devices comprise chips having multiple nanoscale electrode capacitive regions, each in either the one electrode or the two electrode configuration described herein. In referring to a one electrode or a two electrode configuration, we refer to a chip having one or two nanoscale electrodes, which are the electrodes at which impedance and/or capacitance is measured. In some cases the chips comprising arrays of devices will also comprise either a counter electrode or array of counter electrodes, an array of reference electrodes or a reference electrode. In some cases, the chips will have both counter and reference electrodes or will have arrays of both reference and counter electrodes.

The chips of the invention can be produced using known semiconductor processing techniques. These techniques allow for inexpensively producing arrays having large numbers of capacitive devices. The chips have, for example, from 2 to one million or more capacitive devices. In some cases the chips have 9 to 100, 100 to 10,000, or from 10,000 to one million or from 100,000 to 10 million capacitive devices. The number of devices on a chip will depend on the type of application that for which the chip is used. In some cases, having less than 100 capacitive devices is useful, for example in diagnostic applications where a specific answer for a selected set of nucleic acids may be desired in a short time frame. For applications in which high throughput is desired, for example whole human genome sequencing, having a million to 10 million devices is used. It is understood by those of skill in the art that as the number of capacitive devices grows, there are more demands on the system in which the chip is used such as more complex drive and sensing electronics and higher throughput data analysis. Current high throughput sequencing techniques have shown that these issues can be addressed with the appropriate level of engineering.

In some cases, the chips have nanoscale capacitive devices comprising one or two nanoscale electrodes, and electric interconnects connecting the capacitive devices to electrical outputs on the chip. In addition, in some cases there is a counter electrode on the chip for each capacitive device. In some cases there is one counter electrode on the chip for multiple capacitive devices on the chip. For example there can be one counter electrode on the chip for each 1 to each 1,000 devices, one counter electrode for each 10 to 100 devices, or one counter electrode on the chip for all of the devices on the chip.

Typically, where a reference electrode is used, the reference electrode will be separate from the chip, but in some cases, the reference electrode can be on the chip. As with the counter electrodes, in some cases there is a reference electrode on the chip for each capacitive device. In some cases there is one reference electrode on the chip for multiple capacitive devices on the chip. For example there can be one reference electrode on the chip for each 1 to each 1,000 devices, one reference electrode for each 10 to 100 devices, or one reference electrode on the chip for all of the devices on the chip.

The chips can also have corresponding arrays of control electrodes. A control electrode is used to improve signal to noise by having similar characteristics to the nanoscale electrode, but not having a polymerase enzyme bound proximate to it. Subtracting the signal at the control electrode from the signal at the nanoscale electrode can remove noise that is common to both electrodes, and thus improve the signal to noise ratio of at the nanoscale electrode. In some cases there is a control electrode on the chip for each capacitive device. In some cases there is one control electrode on the chip for multiple capacitive devices on the chip. For example there can be one control electrode on the chip for each 1 to each 1,000 devices, one control electrode for each 10 to 100 devices, or one control electrode on the chip for all of the devices on the chip. In some cases, the control electrode can constitute a control capacitive device, for example a control two-electrode capacitive device that intentionally does not have a polymerase enzyme bound proximate to the electrodes.

The chips can also have other incorporated components. Since the devices are made by semiconductor processing techniques, it is straightforward to include other components such as resistors, capacitors, amplifiers, memory circuits, A/D converters, logic circuits, and the like. The circuits can provide the functions of amplification, analog to digital conversion, signal processing, memory, and data output. By having components such as CMOS processors included in the device addresses the issue of monitoring multiple events simultaneously. Rather than having at least one pair of wires bringing signals out from the chip, the inclusion of these components allows for a multiplexed output or an addressable output such as used in a DRAM chip. Where the number of devices is large, there tends to be more of a demand for building in extra circuitry onto the chip. This allows for carrying out partial analysis on the chip in a way that can significantly reduce the need for the amount of electrical signals that have to go to and from the chip.

The electrodes can be made of any suitable conducting material. They are typically made of a conductive metal that is amenable to semiconductor processing. Metals include aluminum, silver, gold, and platinum. The electrodes are fabricated to be on the order of nanometers in at least one dimension, at least two dimensions, or three dimensions. The size of the electrode is dependent on various design parameters. When discussing the size of the electrodes in this application, we are generally referring to the portion of the electrode which is exposed to the fluid sequencing mixture. In many cases, the size of the conductive portions not in contact with the solution are made larger in size to increase conductivity. The electrode should be large enough that when a nucleotide analog having a capacitive label is in the active site, the presence of the capacitive label will effectively detected by the electrode, in some cases, the capacitive label comes into physical contact with the electrode.

FIG. 4 shows some approaches to the geometry of the electrodes of the invention. FIG. 4(A) shows a two electrode configuration with linear electrodes on an insulating substrate. FIG. 4(B) shows a two electrode configuration where the enzyme is attached to an insulating layer between walls of electrode. Note that for (B), the electrode can be made such that only the inside walls of the electrode are effective for measuring capacitance reactions. FIG. 4(C) shows a split circular electrode with an insulating strip in the middle to which the enzyme is attached. FIG. 4(D) shows a circularly symmetric single electrode configuration where the enzyme complex is attached to the electrode. FIG. 4(E) shows a circularly symmetric single electrode configuration in which the enzyme complex is attached to a middle insulating region. This configuration can be useful for providing a chemically distinct region to facilitate selective binding of the polymerase complex. FIG. 4(F) shows a single electrode linear electrode configuration on a flat insulating surface. The electrodes can have any suitable geometry.

Figure 5B:
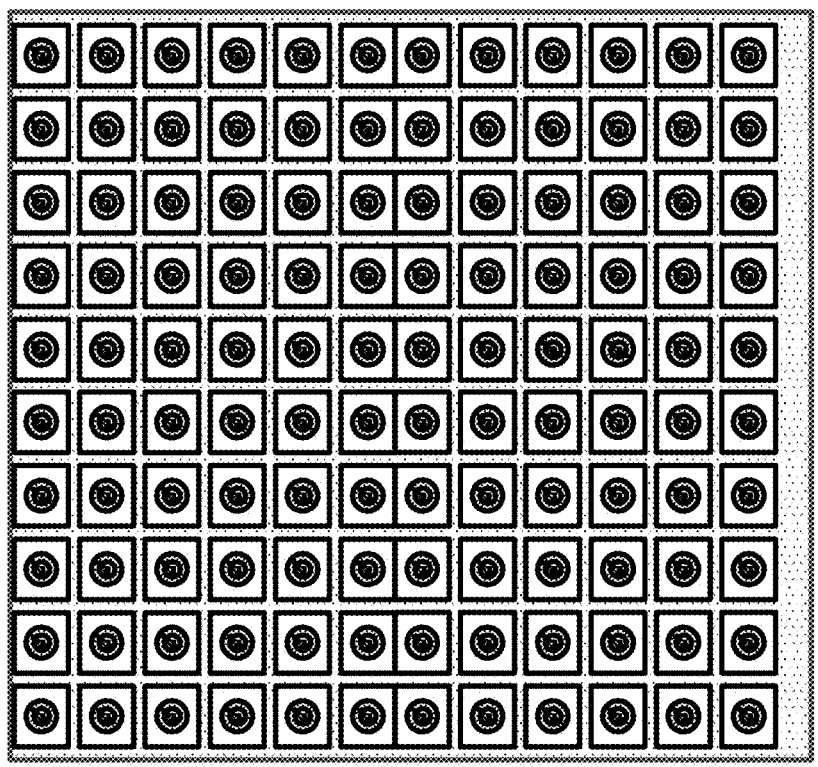
FIG. 5(B) illustrates an array of circularly symmetric one electrode configuration capacitive devices.
Figure 5A:
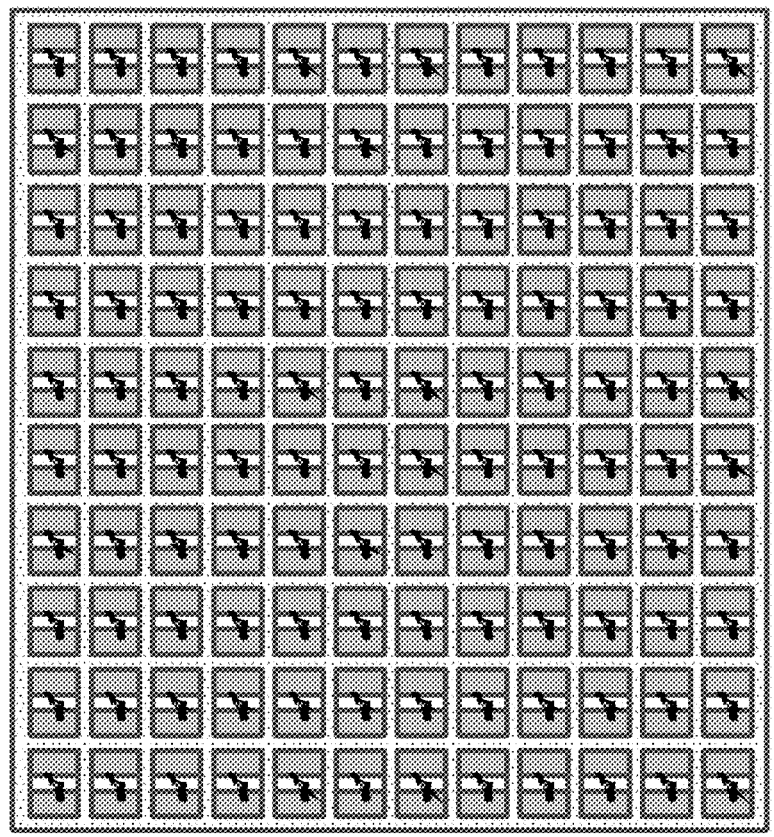
FIG. 5(A) and FIG. (B) illustrate how arrays of nanoscale devices on a chip can be fabricated to allow for simultaneously sequencing multiple templates.

FIG. 5(A) illustrates an array of a linear two electrode configuration capacitive devices. A semiconductor surface can be patterned to produce an array of capacitive devices. The interconnects to connect the nanoscale electrodes to the electrical inputs and outputs can be provided by dropping through vias to lower layers. The electrical connections to the chip are typically made to the sides or to the bottom of the chip. FIG. 5(B) illustrates an array of circularly symmetric one electrode configuration capacitive devices.

FIG. 6 shows cross sections of devices which illustrate some exemplary approaches to single electrode configuration capacitive devices using standard semiconductor processes. These constitute relatively straightforward semiconductor device structures which are made as arrays on chips by standard semiconductor manufacturing techniques. In FIG. 6(A) a substrate 600, typically silicon, has electrical trace 620 extending across the substrate 600. Electrical Trace 620 connects with the electrode 610 through via 690 which extends through layer 650. Insulating layer 640 is deposited on top of the electrode 610 to create a well of insulating material with the electrode 610 as its base. The enzyme complex 630 is bound to the top of the electrode within the insulating well. In FIG. 6(B) electrical interconnect 622 extends across substrate 602, and via 692 extends through layer 652 to electrode 612. A planarization layer 662 is deposited and optionally polished to produce the electrode configuration flush with the surface to which the enzyme complex 632 is attached. In FIG. 6(C) electrical interconnect 624 extends across the substrate 604. Via 694 extends through layer 654 and connects the electrical interconnect 624 to the electrode 614. The polymerase-template complex 634 is attached to electrode 614.

For a two electrode configuration, the two electrodes can be disposed, for example, horizontally or vertically with respect to the top of a substrate. A vertical configuration can be useful for producing thin layers, e.g. from 1 nm to about 100 nm, 2 nm and 50 nm, or 10 nm and 100 nm for the insulating layer between the two nanoscale electrodes. FIG. 7 shows an exemplary approach for producing an array of two electrode capacitive devices on semiconductor substrates. In each of FIGS. 7(A) thorough (F) both a top view and a side view of the device is shown. FIG. 7(A) shows a patterned metal electrode on a substrate such as a silicon substrate. The pattern creates the lower electrode pad and a interconnect that can run out for creating a electrical connection to the chip. In step I, an insulating layer, e.g. $SiO_2$, is deposited, patterned, and etched such that the bottom electrode is covered (FIG. 7(B)). This layer will become the insulating layer between the two nanoscale electrodes in the capacitive device. The insulating layer is typically deposited at a thickness of between 2 nm and 20 nm. While the insulating layer in FIG. 7 is shown as being flat, in some cases, the insulating layer is deposited with decreasing thickness toward the edge that is eventually exposed to form the electrode device. The variation in thickness can allow for having a thin, e.g. 1-10 nm layer where the $SiO_2$ layer is exposed, but having a thicker layer in other portions of the device in order to keep the overall capacitance of the device low. In step II, the top electrode layer is deposited on top of the insulating layer, with the electrode extending off to produce an electrical interconnect (FIG. 7(C)). In step III, a second insulating layer is deposited over the top electrode layer. The second insulating layer is typically different from the first insulating layer, and can be for example silicon nitride or aluminum oxide. Having the first insulating layer (e.g. $SiO_2$) made of a different material can be useful for selectively binding enzyme to the layer between the electrodes (FIG. 7(D)). In step IV, a notch is etched into the electrode insulator stack to expose a portion of the top and bottom electrode and insulating layer (FIG. 7(E)). FIG. 7(F) shows an alternative to the final device in which the electrode layers are angled with respect to one another. This angling allows for the portions of the electrodes that are exposed to be close together (i.e. the $SiO_2$ layer between the electrodes is thin), and it also allows for the bulk of the electrodes to be farther apart from one another, which lowers the capacitance of the capacitive device, allowing for faster charge up and charge down. This method allows for a small and well-controlled two-electrode capacitive device.

Real-Time Conductance Sequencing—Nanowire-nanoFET

One aspect of the invention provides for real time sequencing in which the incorporation of nucleotides into the growing strand is detected using a nanoscale field effect transistor (nanoFET). The incorporation can be detected, for example, by changes in the conductivity of the gate of the nanoFET. In some cases, the FET comprises a nanowire, and incorporation is detected by detecting changes in conductance of a nanowire. A polymerase enzyme complex including a polymerase enzyme and a template nucleic acid is immobilized onto the nanowire or proximal to the nanowire. The polymerase enzyme complex is exposed to a reaction mixture that supports nucleic acid synthesis. The reaction mixture includes nucleotides or nucleotide analogs in which at least one of the types of nucleotide analog has a label that will be referred to herein as a conductance label, a conductivity label. The label is connected to the polyphosphate portion of the nucleotide analog such that when the nucleotide analog is incorporated, the label is released as the polyphosphate chain is cleaved.

The conductance label is selected such that when the nucleotide analog to which it is attached is within the active site of the enzyme, the label produces a change in conductivity of the nanowire to which the polymerase is attached or to which the polymerase enzyme is proximal. The incorporation of the nucleotide analog results in the release of the conductance label, restoring the conductivity of the nanowire to a baseline value. While each of the four types of nucleotides may sample the active site, the nucleotide or nucleotide analog that is incorporated (a cognate nucleotide) will spend a longer time in the active site than a nucleotide or nucleotide analog that is not incorporated. Thus, the conductivity of the nanowire detects when a labeled nucleotide analog is present in the active site of the polymerase enzyme.

The characteristics of the conductance change in the nanowire can be different for different conductance labels. Thus, in addition to detecting the presence of an incorporated nucleotide, the methods of the invention allow for discriminating between two or more nucleotide analogs in the reaction mixture. Typically four types of nucleotide analogs are used, corresponding to A, G, T, and C for DNA and to A, G, U, and C for RNA, each having a different conductance label. By observing the incorporation of nucleotides over time, the sequence of the template nucleic acid in the polymerase enzyme complex can be determined. The polymerase specifically adds a nucleotide to the growing strand that is complementary to the nucleotide in the template strand, e.g. A<->T, and G<->C. By determining which nucleotides have been added to the growing strand, the sequence of the template strand can be determined.

The nanowire can be used as a gate in a nano-field effect transistor or nanoFET, with the electrodes attached to either side of the nanowire acting as the source and the drain. The nanowire can be, for example, a carbon nanotube or a semiconductor such as doped silicon. There are many materials that can make up the nanowire or gate, examples of which are described in more detail below.

In some cases the nanowire or nanoFET are used to perform nucleic acid sequencing by measuring the presence of the labeled nucleotide analog within the enzyme complex as the enzyme adds nucleotides to a growing strand in real time. FIG. 8 provides a schematic representation of a method for real time nucleic acid sequencing with two nanoscale electrodes acting as source and drain with a nanowire or gate connecting them. A polymerase-template complex bound proximate to the nanowire or gate. In FIG. 8 the polymerase enzyme is attached directly to the nanowire. In some cases, rather than being directly attached, the polymerase enzyme is attached to the substrate proximate to the nanowire at a distance such that the presence of a conductivity label attached to a nucleotide analog that is associated with the enzyme is detected by a change in conductance of the nanowire. A substrate 800 has a region on its surface with two electrodes 802 and 806 separated on the order of nanometers. For example, the separation can be from 1 nm to 400 nm, or from 2 nm to 100 nm. A nanowire 804 extends across the gap, connecting electrodes 802 and 806 (the source and drain of the FET). In some cases, the source and drain are covered with an insulating material such that the source and drain are not in direct contact with the solution. Onto the nanowire or gate 804 is attached a polymerase enzyme complex comprising a polymerase enzyme 810 and a nucleic acid template 830. The complex is attached to the nanowire or gate 804 by an attachment moiety 820. As shown in FIG. 8, the polymerase enzyme is attached to the nanowire. In some cases, the template nucleic acid can be attached to the nanowire, either directly, or, for example, through hybridization with a primer attached to the nanowire. In the figure, the nanoscale electrodes and nanowire are shown as disposed on a horizontal surface. In some cases, the electrodes and nanowire are disposed vertically, e.g. as a stack of layers.

The substrate comprising the nanoFETs is contacted with a fluid comprising a sequencing reaction mixture. The sequencing reaction mixture has the reagents required for carrying out polymerase mediated nucleic acid synthesis. The sequencing reaction mixture will generally include divalent catalytic cations such as Mn++ or Mg++ salts for activating the enzyme, as well as other salts such as Na+ or K+ for providing the appropriate ionic strength. These salts can also be used to adjust the background capacitance at the electrodes. The sequencing reaction mixture also contains conductivity labeled nucleotide analogs such as labeled nucleotide analog 840. In FIG. 8, nucleotide analog 840 is a cognate nucleotide having a base that is complementary to the next position in the template nucleic acid 830. The nucleotide analog 840 has a nucleotide portion 844 comprising a nucleobase, a sugar, and a polyphosphate portion. The nucleotide analog 840 has a conductivity label 842 that is attached to the polyphosphate portion of the nucleotide portion 844 through linker 846.

Figures 8A, 8B, 8C:
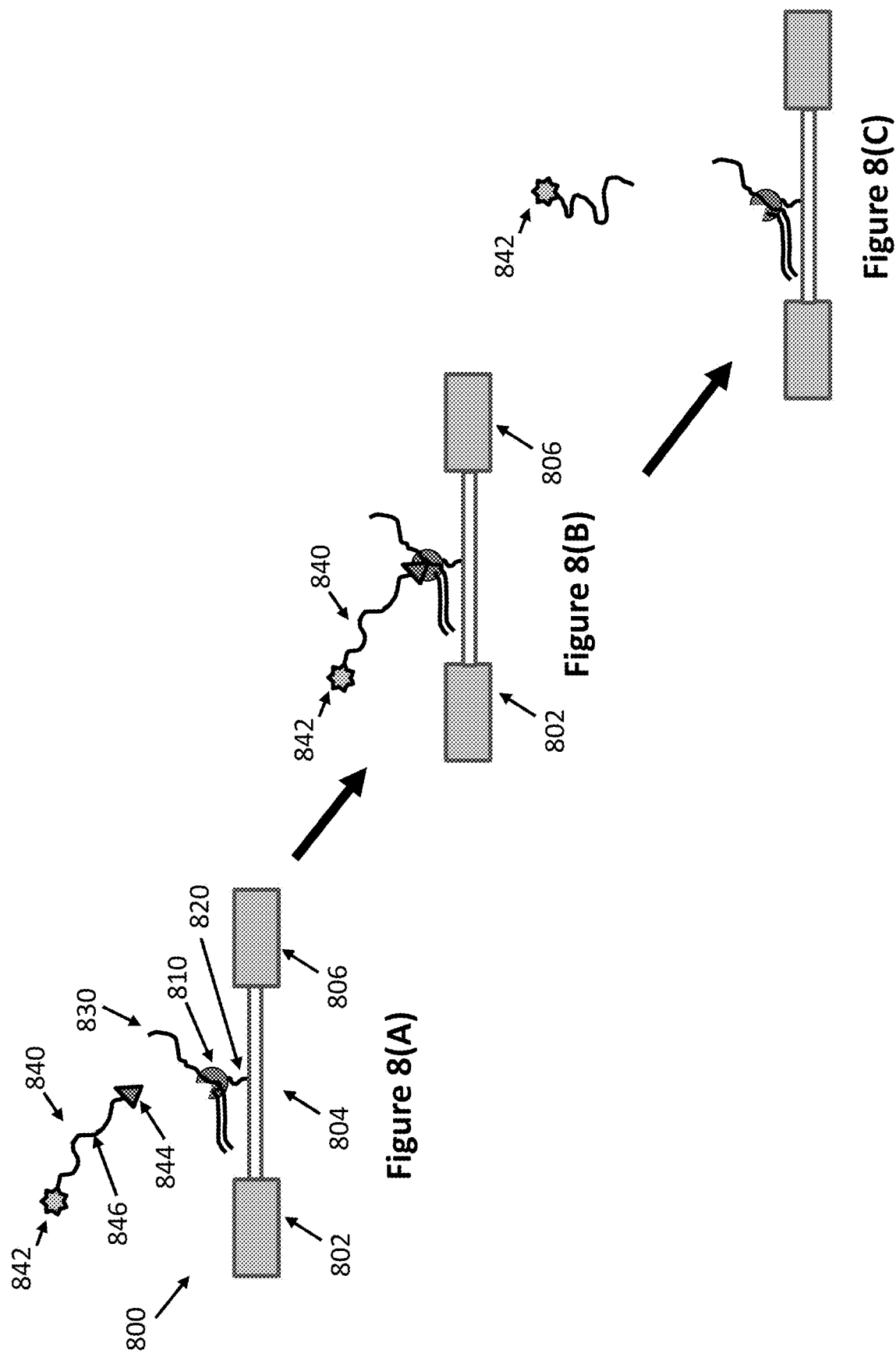
FIGS. 8(A)-(C) illustrates a method of the invention for sequencing using a nanoFET.

In FIG. 8(B) the nucleotide analog 840 is held in the active site of the polymerase enzyme 810. Because it is a cognate nucleotide, nucleotide analog 840 is recognized by the enzyme as such, and will be held in the enzyme longer than will a non-cognate nucleotide. At the time that the nucleotide analog 840 is associated, its presence will be detected by a change in conductivity of the nanowire or gate, resulting in a change in current and/or voltage at the gate and drain (e.g. electrodes) 802 and 806. Electrodes 802 and 806 are addressed with either direct or alternating current. In some cases, the electrodes are cycled through a series of frequencies, either continuously or in steps. The label 842 causes the characteristics of conductivity or impedance as measured at the electrodes to change, allowing both its presence and its identity to be determined.

When the nucleotide portion of analog 840 is incorporated into the growing strand as shown in FIG. 8(C), the polymerase enzyme cleaves the polyphosphate portion of the nucleotide analog. This cleavage occurs between the alpha and beta phosphates in the polyphosphate portion which releases the portion of the nucleotide analog comprising the label 842, which diffuses away from the substrate. This cleavage and diffusion away of the label ends the period in which the conductance of the nanowire or gate is affected by the presence of the label. The change in conductance, then, provides a measure of the residence time of the nucleotide analog in the active site prior to incorporation, which can be used to determine that nucleotide incorporation has occurred.

The paragraphs above describe the detection of one type of nucleotide analog. The same approach is applied to the measurement of the incorporation of more than one type of analog, for example 2, 3, 4, 5 or more types of analogs. For example, typically four different types nucleotide analogs corresponding to either A, G, C, T, for DNA or A, G, C, U for RNA are used. Each of the four types of nucleotide analog has different and distinguishable conductivity characteristics at the nanowire, e.g. four different conductivity labels. The different types of nucleic acid analogs can have different conductivity, different conductivity versus frequency characteristics, or can have other distinguishable electrical characteristics such as different current oscillation color or can have combinations of the above.

The paragraphs above and FIG. 8 describe the detection of a nucleotide analog. The approach described can also be applied to the measurement of the incorporation of more than one type of analog, for example 2, 3, 4, 5 or more types of analogs. For example, typically four different types nucleotide analogs corresponding to either A, G, C, T, for DNA or A, G, C, U for RNA are used for sequencing. Each of the four types of nucleotide analogs has different and distinguishable conductance characteristics, e.g. four different conductivity labels. The different types of nucleotide analogs can have different magnitudes of conductance change, different current versus time attributes, or can have other distinguishable electrical characteristics such as different current oscillation color or can have any combination of the above characteristics.

Figure 9:
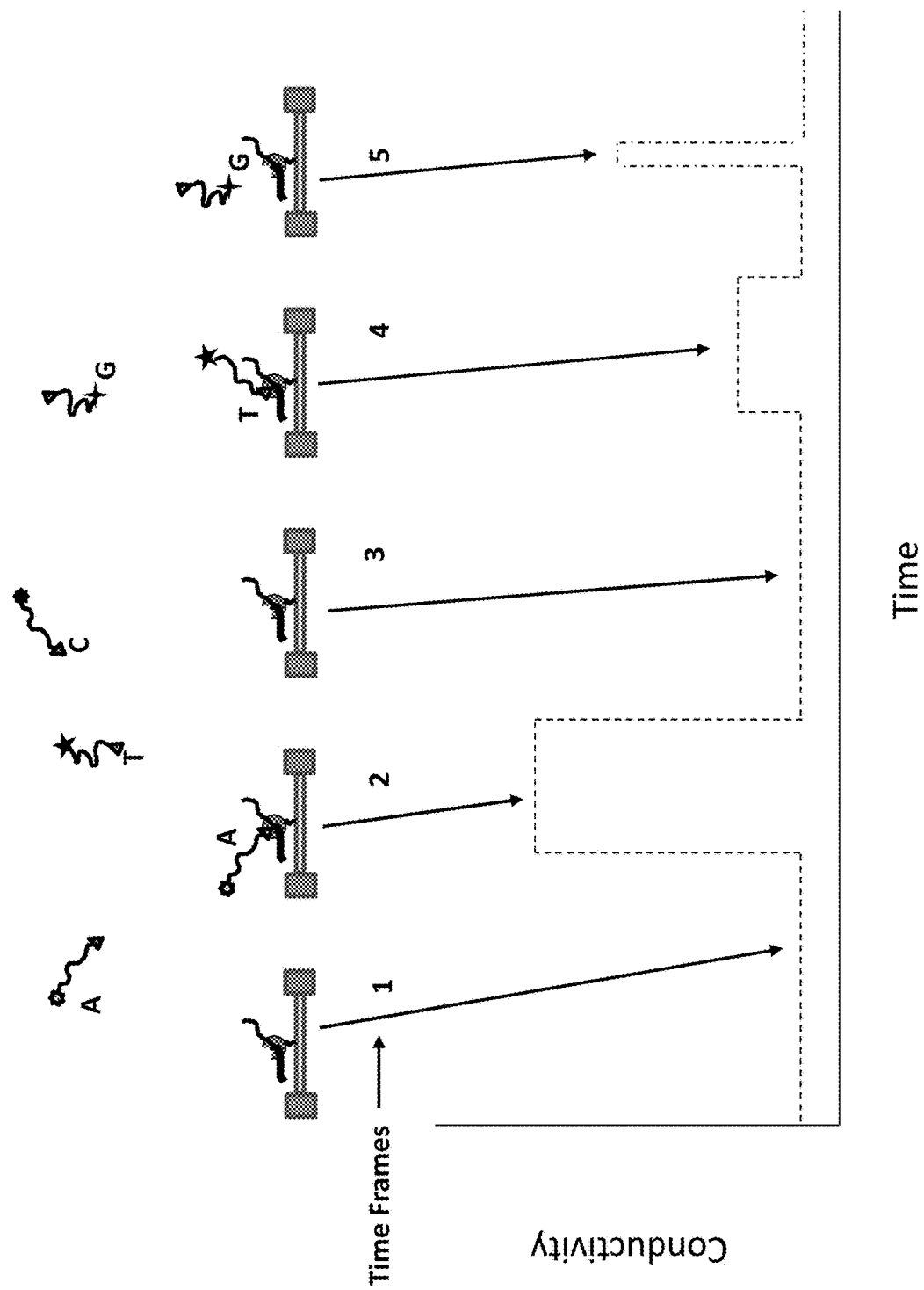
FIG. 9 shows how conductivity over time from the nanoFET can be used to sequence a template nucleic acid.

FIG. 9 shows how the nanowire or gates of the invention can be used to call a series of bases for sequencing. A graph is shown indicating the conductivity signal through the nanowire or gate that is detected. There are four types of nucleotide analogs, each having a different conductivity label, for example, each with a different magnitude of current change in the nanowire or gate when in the vicinity of the nanowire or gate. For example, the voltage across the two electrodes, the source and the drain can be kept constant throughout the experiment, and the current that passes through the nanowire or gate is monitored over time.

The method is described in FIG. 9 by referring to 5 different time frames. During time frame 1, none of the four nucleotide analogs is associated with the polymerase enzyme. In time frame 2, a nucleotide analog corresponding to nucleobase A is in the active site for a time that is characteristic of incorporation (e.g. about 10 msec to about 500 msec). During the time it is in the active site, the measured conductivity rises to a level characteristic of the label on that nucleotide analog. This level of conductivity for a residence time corresponding to incorporation indicates the incorporation of A. When the nucleotide is incorporated, the conductivity label is cleaved and the conductivity signal returns to baseline. In time frame 3, as in time frame 1, no nucleotide analog is in the active site of the polymerase and the conductivity is at a baseline level. During time frame 4, a nucleotide analog corresponding to T is incorporated into the growing strand. The nucleotide analog corresponding to T is held within the active site for a period of time characteristic of incorporation. During the time it is held within the enzyme, a conductivity characteristic of the label on the T nucleotide analog is seen. When the analog is incorporated, the label is cleaved, and diffuses away and the conductivity again returns to baseline. In time frame 5 for a short time, an increase in conductivity (to a level consistent with the label corresponding G) is detected. The time of the increased conductivity is too short to be associated with an incorporation event. This type of feature can be seen, for example, where a non-cognate nucleotide such as G is sampling the active site, after which it diffuses from the enzyme, where the non-cognate nucleotide diffuses near enough to the nanowire to change its conductance, or where the G nucleotide binds non-specifically for a short period of time. During the time of the portion of the experiment shown in FIG. 3, the data indicate that an A and a T were incorporated, which thus indicates that there is a T followed by an A in the template nucleic acid. While this description relates to the incorporation of two nucleotides, this method can be used to sequence long stretches of nucleic acids from hundreds to tens of thousands of bases or more.

The example of FIG. 9 is carried out with four nucleotides, each having a conductivity label that exhibits a different magnitude in conductivity of the nanowire or gate. It will be understood that the same approach described in FIG. 9 can be applied to cases in which conductivity versus time (dielectric spectrum) or current oscillation color or any combination of the three is used to identify the incorporated bases.

Thus, the invention, in some aspects provides a method for nucleic acid sequencing that includes providing a substrate comprising an array of nanoFETs. Each nanoFET has a source, a drain, and a gate. The source and drain are typically nanoelectrode, and the gate is typically a nanowire or other nanostructure connecting the source and drain. The gate can be a doped semiconductor such as doped silicon. The gate can be a carbon nanotube, either single walled or multi-walled. The carbon nanotube gate can be modified or doped. A subset of the nanoFETs will have a single polymerase enzyme complex attached to gate of the nanoFET or attached to the substrate proximate to the gate of the nanoFET. One way of having a single complex attached to the gate or to a region of the substrate proximate to the gate is to attach to the gate or to the region a binding reagent that binds with the polymerase enzyme complex, and to expose the substrate to a solution of polymerase enzyme complex at a concentration whereby a fraction of the nanoFETs have a polymerase enzyme complex becomes bound to gates or to nearby regions at a single molecule level. By selecting the right dilution level, Poisson statistics allows for up to 36% of the gates with a single complex attached, the rest having either no complex or multiple complex. Other methods including using steric interactions and providing highly specific bonding regions on the gate can provide greater levels of single complex than predicted by Poisson statistics.

The substrate is then exposed to a reaction mixture comprising a plurality of types of nucleotide analogs, each comprising a different conductivity label attached to the phosphate portion of the nucleotide analog. The attachment of the label to a phosphate portion allows for cleavage of the label by the polymerase as it breaks the polyphosphate strand when incorporating the nucleotide portion of the nucleotide analog into the growing strand. The label can be connected to the polyphosphate strand through a linker.

A voltage is applied between the source and drain of the nanoFET, such that, when a nucleotide analog resides in the active site of the enzyme, the conductivity label on the nucleotide analog produces a measurable change in the conductivity of the gate. The voltage can be DC, pseudo DC (where the measurement is essentially performed with a DC measurement, but the polarity is alternated to prevent corrosion), or AC. In some cases the frequency across the source and drain can be varied over time to assist in distinguishing the identities of different labels. The conductivity label is typically a charged species whose interaction with the gate results in a change in the conductivity at the gate. In some cases, the conductivity label comes into direct contact, e.g. repeated direct contact, with the gate, and in other cases the conductivity label may affect the conductivity of the gate by its proximity. Both the gate and the conductivity label can be made in a manner to improve the change in conductivity at the gate by the label. For example, as described in detail below the gate can be doped at different levels, either p doped or n doped, in order to tune its response. Conductivity labels are typically charged species that are water soluble. The conductivity labels can have multiple charges, e.g. from about 2 to about 2,000 charges. The labels can comprise dendrimers or nanoparticles. Multiple labels can be employed, each having a different level of charge, in some cases, with some labels positively charged and some labels negatively charged.

During the polymerase enzyme reaction, and while the voltage is applied, an electrical signal comprising the current and voltage at the nanoFET over time is monitored. The electrical signal can indicate that an incorporation event for a specific type of nucleotide analog has occurred. One indication of an incorporation event is the length of the signal, since, depending on the kinetics of the polymerase enzyme used, an incorporation event will occur in a range of times that is different than a diffusion event, a non-cognate sampling event, or sticking of labels to the substrate. Various characteristics of the electrical signal can be used to determine that a particular nucleotide analog is in the active site and being incorporated. One characteristic is the amplitude of the conductivity. For example, four charged labels, each with different levels of the same type of charge can give four different levels of conductivity. The conductivity level can be designed to increase or to decrease in the presence of a given conductivity label, e.g. using positively charged and negatively charged labels. In addition to the numbers of charges, the density of the charges on the label can also affect the signal and the density of charge of the conductivity label can be controlled in order to control the signal at the nanoFET. The electric signal characteristics can also be controlled by controlling the structure of the nucleotide analog to change its current oscillation color characteristics.

The electrical signal can thereby provide the information required for determining the sequence of the template nucleic acid in the polymerase enzyme complex. Algorithms such as those described in U.S. Patent Application No. 2011/0256631 filed Oct. 20, 2011, and in U.S. Pat. No. 8,370,079 which are incorporated by reference herein in their entirety for all purposes.

Typically, the methods of the invention are carried out with four types of nucleotide analogs corresponding the natural nucleotides A, G, C, T, or A, G, C, U, each of the four types of nucleotide analogs having a different conductivity label. The nucleobase on the nucleotide analog will typically be the natural nucleobase, but modified nucleobases can be utilized as long at the polymerase enzyme that is used can effectively incorporate them into the growing strand.

In some aspects the invention provides a chip for sequencing a plurality of single nucleic acid template molecules. The chip has a substrate having a plurality of nanoFET devices, typically on its top surface. Each of the nanoFET devices has a source, a drain and a gate. Onto the gate of some of the nanoFETs on the substrate is a single polymerase enzyme complex bound to the gate or bound to the substrate proximate to the gate of the nanoFET. The polymerase enzyme complex includes a polymerase enzyme and a template nucleic acid. The template nucleic acid is typically primed, and ready to act as a template for nucleic acid synthesis. The substrate is configured such that the nanoFET device comes into contact with a sequencing reaction mixture. The substrate will typically have a well into which the reaction mixture is dispensed, or will have fluidic conduits or fluidic chambers providing the reaction mixture into contact with the nanoFET devices on the surface. The reaction mixture has the reagents required for carrying out nucleic acid synthesis including a plurality of types of nucleotide analogs. Two or more of the nucleotide analogs have different conductivity labels. The conductivity labels interact with the gate to modify its conductivity as described herein. The chip also has electrical connection sites for bringing current and voltage to the nanoFETs, and for receiving electrical signals from the nanoFETs.

The nanoFET on the chip can be any types of nanoFET, including the types of nanoFETs described herein, for example comprising a nanowire and/or comprising doped silicon.

The chip will typically have multiple nanoFET devices, for example, greater than 1,000 nanoFET devices, or greater than 10,000 nanoFET devices. The chip can have, for example, about 1,000 nanoFET devices to about 10 million nanoFET devices or about 10,000 nanoFET devices to about 1 million nanoFET devices.

The chip is typically made using semiconductor processing techniques, allowing for the inclusion of other functionality on the chip including electronic elements for one or more of: providing electrical signals to the nanoFETs, measuring the electrical signals at the nanoFETs, analog to digital conversion, signal processing, and data storage. The electrical elements can be, for example, CMOS elements.

In some aspects, the invention provides a system for sequencing template nucleic acids that has a housing with housing electrical connection sites. The housing electrical connection sites are made to connect with electrical connections on the chip for providing electrical signals to the chip and for receiving electrical signals from the chip. There is a chip that reversibly mates with the housing. The chip is a nanoFET chip as described herein. The system includes an electronic control system electrically connected to the nanoFET devices through the electrical connections to apply desired electrical signals to the nanoscale electrodes and for receiving electrical signals from the nanoFET devices. The system typically has a computer that receives information on the electrical signals at the nanoscale electrodes over time and uses such information to identify a sequence of the template nucleic acid. The computer can also control the performance of the chip, for example, by providing a sequence of electrical signals to the nanoFETs on the chip.

Nucleotide analogs comprising conductivity labels will typically be larger, i.e. have a larger molecular weight than natural nucleotides. These analogs can include, for example, nucleotide analogs describe in U.S. patent application Ser. No. 13/767,619 entitled Polymerase Enzyme Substrates with Protein Shield, filed Feb. 14, 2013, and in U.S. Patent Application 61/862,502, entitled Protected Fluorescent Reagent Compounds, which are incorporated herein by reference for all purposes.

In some cases the conductivity labels comprise beads, for example beads comprising multiple nucleotides attached via their polyphosphate portion. Such analogs are described, for example in U.S. Pat. No. 8,367,813 which is incorporated by reference herein in its entirety for all purposes. The beads can be coated with charged functional groups, anionic, cationic, or a combination of anionic and cationic groups. The amount of charge on the bead can be controlled in order to control the electrical signal at the gate of the nanoFET. The beads can have any usable size range, for example, between about 2 nm and about 50 nm in size. The shapes of the beads can be spherical, elongated, or other effective shape for controlling the current at the gate of the nanoFET.

Methods for making and addressing nanoFETs including nanoFETs comprising nanowires are known in the art. See, for example, Choi et al. "Single-Molecule Lysozyme Dynamics Monitored by an Electronic Circuit" Science 335, 319 (2012), and Patolsky et al., "Electrical Detection of Viruses", PNAS, 101(39), 14017, 2004 which are incorporated herein by reference in their entirety for all purposes.

The measured signal can be from a change in any suitable electrical property of the nanoscale wire, such as voltage, current, conductivity, resistivity, inductance, impedance, electrical change, an electromagnetic change, etc.

Thus, the polymerase complex may be positioned relative to the nanoscale wire to cause a detectable change in the nanoscale wire. In some cases, the polymerase complex may be positioned within about 100 nm of the nanoscale wire, within about 75 nm of the nanoscale wire, within about 50 nm of the nanoscale wire, within about 20 nm of the nanoscale wire, within about 15 nm of the nanoscale wire, or within about 10 nm of the nanoscale wire. The actual proximity can be determined by those of ordinary skill in the art. In some cases, the polymerase complex is positioned less than about 5 nm from the nanoscale wire. In other cases, the polymerase complex is positioned within about 4 nm, within about 3 nm, within about 2 nm, or within about 1 nm of the nanoscale wire.

In some embodiments, the polymerase complex is fastened to or directly bonded (e.g., covalently) to the nanowire (nanoscale wire) or gate, e.g., as further described herein. However, in other embodiments, the polymerase complex is not directly bonded to the nanoscale wire, but is otherwise immobilized relative to the nanowire, i.e., the polymerase complex is indirectly immobilized relative to the nanowire. For instance, the polymerase complex may be attached to the nanowire through a linker, i.e., a species (or plurality of species) to which the polymerase complex and the nanoscale wire are each immobilized relative thereto, e.g., covalently or non-covalently bound to. As an example, a linker may be directly bonded to the nanoscale wire, and the polymerase complex may be directly bonded to the linker, or the polymerase complex may not be directly bonded to the linker, but immobilized relative to the linker, e.g., through the use of non-covalent bonds such as hydrogen bonding (e.g., as in complementary nucleic acid-nucleic acid interactions), hydrophobic interactions (e.g., between hydrocarbon chains), entropic interactions, or the like. The linker may or may not be directly bonded (e.g., covalently) to the nanoscale wire.

Many nanowires as used in accordance with the present invention are individual nanowires. As used herein, "individual nanowire" means a nanowire free of contact with another nanowire (but not excluding contact of a type that may be desired between individual nanowires, e.g., as in a crossbar array). For example, an "individual" or a "free-standing" article may, at some point in its life, not be attached to another article, for example, with another nanowire, or the to free-standing article may be in solution. An "individual" or a "free-standing" article is one that can be (but need not be) removed from the location where it is made, as an individual article, and transported to a different location and combined with different components to make a functional device such as those described herein and those that would be contemplated by those of ordinary skill in the art upon reading this disclosure.

In another set of embodiments, the nanowire (or other nanostructured material) may include additional materials, such as semiconductor materials, dopants, organic compounds, inorganic compounds, etc. The following are non-limiting examples of materials that may be used as dopants within the nanowire. The dopant may be an elemental semiconductor, for example, silicon, germanium, tin, selenium, tellurium, boron, diamond, or phosphorous. The dopant may also be a solid solution of various elemental semiconductors. Examples include a mixture of boron and carbon, a mixture of boron and P(BP6), a mixture of boron and silicon, a mixture of silicon and carbon, a mixture of silicon and germanium, a mixture of silicon and tin, a mixture of germanium and tin, etc. In some embodiments, the dopant may include mixtures of Group IV elements, for example, a mixture of silicon and carbon, or a mixture of silicon and germanium. In other embodiments, the dopant may include mixtures of Group III and Group V elements, for example, BN, BP, BAs, AlN, AlP, AlAs, AlSb, GaN, GaP, GaAs, GaSb, InN, InP, InAs, or InSb. Mixtures of these combinations may also be used, for example, a mixture of BN/BP/BAs, or BN/AlP. In other embodiments, the dopants may include mixtures of Group III and Group V elements. For example, the mixtures may include AlGaN, GaPAs, InPAs, GaInN, AlGaInN, GaInAsP, or the like. In other embodiments, the dopants may also include mixtures of Group II and Group VI elements. For example, the dopant may include mixtures of ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, to for example, ZnCd Se, or ZnSSe or the like. Additionally, mixtures of different groups of semiconductors may also be possible, for example, combinations of Group II-Group VI and Group III-Group V elements, such as $(GaAs)_x(ZnS)_{1-x}$. Other non-limiting examples of dopants may include mixtures of Group IV and Group VI elements, for example GeS, GeSe, GeTe, SnS, SnSe, SnTe, PbO, PbS, PbSe, PbTe, etc. Other dopant mixtures may include mixtures of Group I elements and Group VII elements, such as CuF, CuCl, CuBr, CuI, AgF, AgCl, AgBr, AgI, or the like. Other dopant mixtures may include different mixtures of these elements, such as $BeSiN_2$, $CaCN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$, $(Al, Ga, In)_2(S, Se, Te)_3$, $Al_2CO$, $(Cu, Ag)(Al, Ga, In, Tl, Fe)(S, Se, Te)_2$ or the like.

As a non-limiting example, a p-type dopant may be selected from Group III, and an n-type dopant may be selected from Group V. For instance, a p-type dopant may include at least one of B, Al and In, and an n-type dopant may include at least one of P, As and Sb. For Group III-Group V mixtures, a p-type dopant may be selected from Group II, including one or more of Mg, Zn, Cd and Hg, or Group IV, including one or more of C and Si. An n-type dopant may be selected from at least one of Si, Ge, Sn, S, Se and Te. It will be understood that the invention is not limited to these dopants, but may include other elements, alloys, or mixtures as well.

As used herein, the term "Group," with reference to the Periodic Table, is given its usual definition as understood by one of ordinary skill in the art. For instance, the Group II elements include Mg and Ca, as well as the Group II transition elements, such as Zn, Cd, and Hg. Similarly, the Group III elements include B, Al, Ga, In and Tl; the Group IV elements include C, Si, Ge, Sn, and Pb; the Group V elements include N, P, As, Sb and Bi; and the Group VI elements include O, S, Se, Te and Po. Combinations involving more than one element from each Group are also possible. For example, a Group II-VI material may include at least one element from Group II and at least one element from Group VI, e.g., ZnS, ZnSe, ZnSSe, ZnCdS, CdS, or CdSe. Similarly, a Group III-V material may include at least one element from Group III and at least one element from Group V, for example GaAs, GaP, GaAsP, InAs, InP, AlGaAs, or InAsP. Other dopants may also be included with these materials and combinations thereof, for example, transition metals such as Fe, Co, Te, Au, and the like. The nanoscale wire of the present invention may further include, in some cases, any organic or inorganic to molecules. In some cases, the organic or inorganic molecules are polarizable and/or have multiple charge states.

In some embodiments, at least a portion of a nanowire may be a bulk-doped semiconductor. As used herein, a "bulk-doped" article (e.g. an article, or a section or region of an article) is an article for which a dopant is incorporated substantially throughout the crystalline lattice of the article. For example, some articles such as carbon nanotubes are typically doped after the base material is grown, and thus the dopant only extends a finite distance from the surface or exterior into the interior of the crystalline lattice. In some embodiments, a bulk-doped semiconductor may comprise two or more bulk-doped regions. Thus, as used herein to describe nanowires, "doped" refers to bulk-doped nanowires, and, accordingly, a "doped nanoscopic (or nanoscale) wire" is a bulk-doped nanowire. "Heavily doped" and "lightly doped" are terms the meanings of which are understood by those of ordinary skill in the art.

In one set of embodiments, the invention includes a nanoscale wire (or other nanostructured material) that is a single crystal. As used herein, a "single crystal" item (e.g., a semiconductor) is an item that has covalent bonding, ionic bonding, or a combination thereof throughout the item. Such a single-crystal item may include defects in the crystal.

In yet another set of embodiments, the nanoscale wire (or other nanostructured material) may comprise two or more regions having different compositions. Each region of the nanoscale wire may have any shape or dimension, and these can be the same or different between regions. For example, a region may have a smallest dimension of less than 1 micron, less than 100 nm, less than 10 nm, or less than 1 nm. In some cases, one or more regions may be a single monolayer of atoms (i.e., "delta-doping"). In certain cases, the region may be less than a single monolayer thick (for example, if some of the atoms within the monolayer are absent).

In still another set of embodiments, a nanoscale wire may be positioned proximate the surface of a substrate, i.e., the nanoscale wire may be positioned within about 50 nm, about 25 nm, about 10 nm, or about 5 nm of the substrate. In some cases, the proximate nanoscale wire may contact at least a portion of the substrate. In one embodiment, the substrate comprises a semiconductor and/or a metal. Non-limiting examples include Si, Ge, GaAs, etc. Other suitable semiconductors and/or metals are to described above with reference to nanoscale wires. In certain embodiments, the substrate may comprise a nonmetal/nonsemiconductor material, for example, a glass, a plastic or a polymer, a gel, a thin film, etc. Non-limiting examples of suitable polymers that may form or be included in the substrate include polyethylene, polypropylene, poly(ethylene terephthalate), polydimethylsiloxane, or the like.

A nanowire, nanoscopic wire on nanoscale wire is generally a wire, that at any point along its length, has at least one cross-sectional dimension and, in some embodiments, two orthogonal cross-sectional dimensions less than about 200 nm, less than about 150 nm, less than about 100 nm, less than about 70, less than about 50 nm, less than about 20 nm, less than about 10 nm, or less than about 5 nm. In other embodiments, the cross-sectional dimension can be less than 2 nm or 1 nm. In one set of embodiments, the nanoscale wire has at least one cross-sectional dimension ranging from 0.5 nm to 100 nm or 200 nm. In some cases, the nanoscale wire is electrically conductive. Where nanoscale wires are described having, for example, a core and an outer region, the above dimensions generally relate to those of the core. The cross-section of a nanoscopic wire may be of any arbitrary shape, including, but not limited to, circular, square, rectangular, annular, polygonal, or elliptical, and may be a regular or an irregular shape. The nanoscale wire may be solid or hollow. A non-limiting list of examples of materials to from which nanoscale wires of the invention can be made appears below. Any nanoscale wire can be used in any of the embodiments described herein, including carbon nanotubes, molecular wires (i.e., wires formed of a single molecule), nanorods, nanowires, nanowhiskers, organic or inorganic conductive or semiconducting polymers, and the like, unless otherwise specified. Other conductive or semiconducting elements that may not be molecular wires, but are of various small nanoscopic-scale dimensions, can also be used in some instances, e.g. inorganic structures such as main group and metal atom-based wire-like silicon, transition metal-containing wires, gallium arsenide, gallium nitride, indium phosphide, germanium, cadmium selenide, etc.

A wide variety of these and other nanoscale wires can be grown on and/or applied to surfaces in patterns useful for electronic devices in a manner similar to techniques described herein involving the specific nanoscale wires used as examples, without undue experimentation. The nanoscale wires, in some cases, may be formed having dimensions of at least about 1 micron, at least about 3 microns, at least about 5 microns, or at least about 10 microns or about 20 microns in length, and can be less than about 100 nm, less than about 80 nm, less than about 60 nm, less than about 40 nm, less than about 20 nm, less than about 10 nm, or less than about 5 nm in thickness (height and width). The nanoscale wires may have an aspect ratio (length to thickness) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases. The nanowires of the invention include wires that are solid, and may be elongated in some cases. In some cases, a nanowire is an elongated semiconductor, i.e., a nanoscale semiconductor.

A "nanotube" (e.g. a carbon nanotube) is typically a nanoscopic wire that is hollow, or that has a hollowed-out core, including those nanotubes known to those of ordinary skill in the art. Nanotubes are used as one example of small wires for use in the invention and, in certain embodiments, devices of the invention include wires of scale commensurate with nanotubes. Examples of nanotubes that may be used in the present invention include, but are not limited to, single-walled nanotubes (SWNTs). Structurally, SWNTs are formed of a single graphene sheet rolled into a seamless tube. Depending on the diameter and helicity, SWNTs can behave as one-dimensional metals and/or semiconductors. SWNTs. Methods of manufacture of nanotubes, including SWNTs, and characterization are known. Methods of selective functionalization on the ends and/or sides of nanotubes also are known, and the present invention makes use of these capabilities for molecular electronics in certain embodiments. Multi-walled nanotubes are well known, and can be used as well.

Distinguishing Labels—Calling Bases

In the sequencing methods of the invention, there are usually two or more different types of labeled nucleotide analogs, and typically there are four different types of nucleotide analog. There are various approaches to distinguish the various types of bases. The discussion will generally involve distinguishing four bases but it is understood that the same approaches can be used to distinguish, two, three, five or more types of nucleotide analogs.

Distinguishing nucleotide types is done, for example, using the characteristics of magnitude of impedance, impedance versus frequency, and impedance current versus time characteristics (current oscillation color). Combinations of the above can also be useful; for example by using two labels and two amplitudes; two types of impedance versus frequency, and two types of current oscillation color, etc. While the capacitance devices and nanoFET devices work by different principles, there are similarities in the types of labels that can be used in each of them. For example, controlling the number, density, and type of charge, and the use of macromolecular charged labels can be useful for either type of electrical detection.

Labels that can provide differences in capacitance or conductivity are known in the art. In some cases, small molecules can be used. Typically a particle, such as a nanoparticle is used as the capacitive or conductivity label. Thus, where a label is described for use in capacitance detection, the label should also be considered for conductivity detection for the nanoFET devices. The characteristics of the nanoparticle can be varied in order to produce different capacitance values. The size of the nanoparticle can influence the capacitance of the particle, as well as the chemical structure. Nanoparticles of metals, semiconductors, glasses, oxides, carbon, silicon, protein, polymers, ionic materials, can be used and can be produced to have widely different impedance magnitude and impedance versus frequency characteristics. The size of the particles can be varied over a wide range, for example from about 2 nanometers to about 50 nanometers in diameter. One large contributor to the impedance change near an electrode is the capacitance characteristics of the material itself. However, it is to be understood that the impedance that is being measured is that of the region around the electrode, and not just that of the label. For example, a nanoparticle label will displace the solution near the electrode, such that the measured impedance will include that change. Thus, a capacitive label near the electrode can result in the impedance either going up or going down as compared to the impedance when the label is not present.

Differentiating nucleotide analogs based on the magnitude of impedance or conductivity change can be carried out, for example, by providing a capacitive or conductivity label having multiple capacitive or conductive moieties on a nucleotide analog. Nucleotide analog structures including those having multivalent scaffolds and nucleotides having multiple moities can be prepared as described, for example, in US Patent Application 20120058473 Molecular Adaptors for Dye Conjugates, and US Patent Application 20120077189 Scaffold-Based Polymerase Enzyme Substrates, which are incorporated herein by reference for all purposes. While these references generally describe a fluorescent label, it is to be understood in conjunction with the teachings of this application that a suitable capacitive label or conductivity label connected by a suitable linker as described herein can be substituted for the fluorescent label.

The terms impedance, conductivity, and capacitance are both used herein. It is to be understood that impedance is the more general term, and that impedance typically has both capacitive and resistive (conductivity) components. For example, for a given system, current flow at low frequencies is dominated by the level of conductivity or resistivity, while the current flow at high frequencies is dominated by the level of capacitance. For the capacitive devices described herein, the frequencies are typically on the order of tens of kilohertz or greater. At these frequencies, for the geometries and materials described, the impedance is predominated by capacitive rather than resistive components. For the nanoFET devices of the invention, low frequencies e.g. DC can be used in which resistivity (conductivity) is the dominant component. While the impedance in each case may be dominated by one component, either capacitance or resistivity, it is will be understood by those of skill in the art that in some cases a combination of these components is present and those of skill in the art will understand the meanings of the terms by their context herein.

Nucleotide analogs can also be differentiated by their impedance versus frequency characteristics. The measured impedance of a label will also be highly dependent on the frequency. It is well known that the components that contribute to impedance in a given system can vary significantly with frequency, for example ionic motion can predominate at some frequencies and dipolar contributions can predominate at other frequencies. Measurements of this type are sometimes referred to as impedance spectroscopy or dielectric spectroscopy measurements. See e.g. Barsoukov, et al. "Impedance Spectroscopy: Theory, Experiment, and Applications", Wiley, 2005, and Kremer et al. "Broadband dielectric spectroscopy", Springer, 2003, the contents of which are incorporated herein by reference for all purposes. Different labels exhibit different impedance versus frequency characteristics, and these characteristics can be used to provide distinct labels and to increase the confidence in base calling.

The impedance of a label can also vary with the amplitude of the voltage applied to the nanoscale electrode at a given frequency. The voltage applied can be adjusted to obtain the best distinction between the various labels. In some cases, the voltage can be varied instead of or in addition to varying the frequency as described above, allowing labels to be distinguished, at least in part, by their impedance versus electrode voltage characteristics.

The current versus time characteristics can be referred to as current oscillation color. For example, two nucleotide analogs, each having the same capacitive label or conductivity label but having different length linkers can exhibit different capacitive current versus time characteristics. Current oscillation color can be used for both capacitive devices and for nanoFET devices. The nucleotide with the longer linker, may, for example, diffuse differently and thus exhibit a different impedance over time characteristics than the nucleotide analog with the shorter linker. This difference in frequency of current oscillation can be used to determine which of the nucleotide analogs is associated with the enzyme. In addition to linker length, the current oscillation color can be influenced by other characteristics of the linker such as its spring constant. The current oscillation color will depend on the characteristics of the measurement system such as electrode geometry and polymerase complex attachment. These factors can be chosen to control differences in current oscillation color to enhance the determination of which nucleotide is incorporated.

Nucleotides or analogs that can thus be identified by the spectrum of the electrical oscillation they produce. In some cases, oscillations looks like noise, but with reproducible and identifiable characteristics including the frequency and the magnitude of the signal. These different types of oscillations can be used like different colored dyes are used to differentiate between different nucleotide analogs in optical systems, thus, we refer herein to a distinguishable type of current oscillation as a current oscillation color.

While the measurement of capacitance is described as a measurement of impedance of current, it is understood by those in the art that this current can in some cases be measured by measuring a voltage. Where we refer to measuring current or voltage, it is to be understood that one can be used to measure or represent the other with respect to measuring impedance or capacitance. In addition to current and voltage, resistance or impedance measurements can also be employed.

One aspect of the invention is the utilization of additional parameters beyond just the impedance change and the impedance spectrum of a label to classify the species associated with the enzyme. Such parameters are measurable over the duration of a pulse. Two general categories of measurement scenarios are: quasi-equilibrium measurement and non-equilibrium measurement.

In quasi-equilibrium measurement, there is some static constraints that remains in place over the duration of the event, and that the removal of that constraint effectively determines the end of the event (except for a negligibly short interval at the end while the detectable object clears the electrode). Though the constraint is fixed, the rest of the components of the system are free to move, and this leads to fluctuations in the signal. For example, diffusion (or equivalently Brownian motion) will cause movement of the label. Under most circumstances, that motion will be correlated with changes in the current across the nanopore, and thus the voltages that might be measured elsewhere in the system. Because of this, aspects of the detectable moiety such as the submolecular diffusion constant (the diffusibility of just that part of the molecule, even when another part of the molecule is constrained) will change the speed of those motions and thus the characteristic frequencies with which the observed voltages or currents will change. For example, a fast diffuser will generally have a whiter noise spectrum, while a slower diffuser will tend to produce a pinker current oscillation spectrum.

The current oscillation color can be used as the basis for a discriminator, for example, by 1) taking the current oscillation signature over a region of interest (e.g. over the duration of the event), 2) performing a Fourier transform analysis or an autocorrelation analysis, and examine the spectrum of the current oscillation over the range of frequencies available (e.g. from $f=1/T$ where T is the duration of the pulse, up to the cutoff frequency of the amplifier system, or somewhat beyond the cutoff). This process will result in a digitally sampled current oscillation amplitude as a function of frequency. This could be represented by as few as two samples (a low frequency region and a high frequency region), 3, 4, 5, 6, 7, 8, 9, 10, 11, 12, 16, 32, 64, 128, 256, 512, 1024 or more bins. The values in these bins could be discrete samples of a function or they represent integrals over a region of interest of the idealized continuous function.

This set of discrete values can be represented as a vector that can be classified by one of many machine learning systems such as k-means clustering, SVM, CART or boosted CART, PCA and many others. Thus, as described herein, current oscillation color can be used to discriminate detectable moieties. Detection systems that are based on current oscillation color can be referred to as "current oscillation color identification systems", and when moieties engineered for producing different current oscillation color are used, they are referred to as "current oscillation color tags". In a sequencing system, when nucleotide base sequence is identified on this basis it can be referred to as a current oscillation color sequencing system (whether the current oscillation color is intrinsic to the bases or the result of current oscillation color tags).

Other aspects besides the diffusion constant can affect the current oscillation color of the signal. For example, in the embodiments that use linkers with different elastic constants, this will affect the magnitude of these diffusive fluctuations, which will then affect the current oscillation signal (not to be confused with the amplitude of the DC current during the event—this is referring to the RMS noise of the signal over the duration of the event). In analogy with color systems that have RGB, or HSV, color can be generalized to include the "brightness" of the color. In the above-mentioned spectrum analysis model, this would result in the values in the vector being larger for moieties capable of larger excursions, and lower values for moieties that are more constrained in position. Some or all of these signals can be exploited in the machine learning paradigm indicated above. There are many aspects that can affect the size of the excursions.

The nanoscale electrodes of the invention are typically prepared such that the electrodes have low capacitance in order to allow for rapidly changing the voltage on the electrodes to carry out the sequencing methods described herein. The resistance and capacitance are kept low by the selection of materials and by the geometry of the electrodes and the spacing of the electrodes. One of the considerations is keeping the RC time constant of each capacitive device low enough to allow for changing the voltage on the electrodes to carry out the methods described herein. In some cases, the RC time constant for the electrode is less than 100 microseconds, less than 10 microseconds, less than 1 microsecond, less than 0.1 microseconds, or less than 0.01 microseconds. In some cases, the RC time constant is between 0.01 microseconds and 100 microseconds. In order to keep the RC time constant low, the electrodes and the interconnects that carry current to and from the electrodes are formed from a material having an electrical conductivity of greater than 106 S/m. Suitable materials include copper, silver, gold, platinum, and aluminum. In order to keep the capacitance low, the dimensions of the electrodes are also generally small—on the nanometer scale. In addition, where there are two electrodes near each other as in the two electrode configuration, while the electrode portions exposed to the surface are close together, the electrodes are configured not to have large portions where the two electrodes are within a few nanometers. For example, for the two electrode configuration illustrated in FIG. 7(F), the electrode structures are close together near the region where they are exposed and where the capacitance will be measured in order for the capacitance to be sensitive to changes at small volumes, but the electrodes taper away from each other within the structure in order to minimize capacitance in the bulk. It is also an aspect of the invention to minimize the area of electrodes that is in contact with conductive liquid so as to control the capacitance of the system. Similarly it is an aspect of the invention to use insulating layers to increase the distance to ground planes, other electrodes, or any other conductor which could produce stray capacitance.

The ability to electrically address the small capacitive devices of the instant invention quickly due to the low RC time constant of the structures is useful for carrying out the invention as it allows for sampling multiple frequency regimes to identify the identity of the different capacitive components that are present.

The methods described herein provide for identifying the nucleotide analogs that are incorporated in to a growing nucleic acid strand as they are incorporated in the bound polymerase-template complex. The presence and identity of the bases is measured by measuring impedance or capacitance in electrodes proximate to the bound polymerase-template complex. As described above, the presence of a capacitive label corresponding to a particular base proximate to a capacitive electrode for a period of time corresponding to the time for base incorporation indicates that that base has been incorporated. The incorporation of that base into the growing strand indicates the presence of the complementary base in the template strand, providing sequence information about the template. The calling of bases is done using software that takes the current versus time information, and in some cases other information in order to call the base that has been incorporated.

An exemplary process for pulse recognition is as follows. Once the current traces have been generated for a given capacitive device for a certain time period, the current traces are subjected to a pulse recognition process. In the initial step, a baseline is established for the trace. Typically, the baseline may comprise signal contributions from a number of background sources (depending on the details of the spectral and trace extraction steps). For example, such noise can include, e.g., global background (e.g. large scale spatial cross-talk) and diffusion background. These backgrounds are generally stable on the timescales of pulses, but still may vary slowly over longer timescales. Baseline removal comprises any number of techniques, ranging from, e.g.: a median of the trace, running lowest-percentile with bias correction, polynomial and/or exponential fits, or low-pass filtering with an FFT. Generally these methods will attempt to be robust to the presence of pulses in the trace and may actually be derived at through iterative methods that make multiple passes at identifying pulses and removing them from consideration of baseline estimation. In certain preferred embodiments, a baseline or background model is computed for each trace channel, e.g., to set the scale for threshold-based event detection.

Other baselining functions include correction for drift or decay of overall signal levels. For example, global background decay is sometimes observed. This global background decay is present on portions of the substrate at which there is no enzyme bound proximate to nanoscale electrodes (control electrodes), thus allowing the traces derived from these locations to be used in combination with the two dimensional global background image to estimate the contribution of this signal to every trace/channel across the chip. This component of variability can then be subtracted from each trace and is usually very effective at removing this decay. Typically, this is carried out prior to the baselining processes.

Following establishment of the baseline the traces are subjected to noise suppression filtering to maximize pulse detection. In particularly preferred aspects, the noise filter is a 'matched filter' that has the width and shape of the pulse of interest. While current pulse timescales (and thus, pulse widths) are expected to vary among different capacitive labeled nucleotides, the preferred filters will typically look for pulses that have a characteristic shape with varying overall duration. For example, a boxcar filter that looks for a current pulse of prolonged duration, e.g., from about 10 ms to 100 or more ms, provides a suitable filter. This filtering is generally performed in the time-domain through convolution or low-pass frequency domain filtering. Other filtering techniques include: median filtering (which has the additional effect of removing short timescale pulses completely from the trace depending on the timescale used), and Savitsky-Golay filtering which tends to preserve the shape of the pulse—again depending on the parameters used in the filter).

Although described in terms of a generic filtering process across the various traces, it will be appreciated that different pulses may have different characteristics, and thus may be subjected to trace specific filtering protocols. For example, in some cases, a given capacitive labeled analog (e.g., A) may have a different pulse duration for an incorporation event than another different capacitive labeled analog (e.g., T). As such, the filtering process for the spectral trace corresponding to the A analog will have different filtering metrics on the longer duration pulses, than for the trace corresponding to the T analog incorporation. In general, such filters (e.g., multi-scale filters) enhance the signal-to-noise ratio for enhanced detection sensitivity. Even within the same channel there may be a range of pulse widths. Therefore typically a bank of these filters is used in order to maximize sensitivity to pulses at a range of timescales within the same channel.

In identifying pulses on a filtered trace, a number of different criteria can be used. For example, one can use absolute current amplitude, either with or without normalization. Alternatively, one can identify pulses from the pulse to diffusion background ratio as a metric for identifying the pulse. In still other methods, one may use statistical significance tests to identify likely pulses over the background noise levels that exist in a given analysis. The latter method is particularly preferred as it allows for variation in potential pulse intensities, and reduces the level of false positives called from noise in the baseline.

As noted previously, a number of signal parameters including amplitude of capacitance change, impedance versus frequency, residence time, and current oscillation color may be and generally are used in pulse identification (as well as in pulse classification). For purposes of illustration, the discussion below primarily on the use of two pulse metrics, namely pulse intensity and pulse width. As will be appreciated, the process may generally include any one or more of the various pulse metric comparisons set forth elsewhere herein.

As such, following filtering, standard deviation of the baselines (noise and current pulses) and determination of pulse detection thresholds are carried out. Preferred methods for determining the standard deviation of a trace include robust standard deviation determinations including, e.g., being based upon the median absolute difference about the baseline, a Gaussian or Poisson fit to the histogram of baselined intensities, or an iterative sigma-clip estimate in which extreme outliers are excluded. Once determined for each trace, a pulse is identified if it exceeds some preset number of standard deviations from the baseline. The number of standard deviations that constitute a significant pulse can vary depending upon a number of factors, including, for example, the desired degree of confidence in identification or classification of significant pulses, the signal to noise ratio for the system, the amount of other noise contributions to the system, and the like. In a preferred aspect, the up-threshold for an incorporation event, e.g., at the initiation of a pulse in the trace, is set at about 5 standard deviations or greater, while the down-threshold (the point at which the pulse is determined to have ended) is set at 1.25 standard deviations. Up thresholds can be used as low as 3.75 standard deviations and as high as the signal-to-noise ratio will allow-up to 7, 10, 20 or 50 standard deviations. The down threshold can be set anywhere from minus 1 standard deviation up to the up threshold. Alternatively, the down threshold can be computed from the mean and standard deviation of the up signal, in which case it could be set between minus 3 standard deviations to minus 6 standard deviations. If the signal-to-noise ratio is sufficiently high it could be set to minus 7, 10, 20 or 50 standard deviations. The pulse width is then determined from the time between the triggering of the up and down thresholds. Once significant pulses are initially identified, they are subjected to further processing to determine whether the pulse can be called as a particular base incorporation. Alternatively the signals can be filtered ahead of time to eliminate frequency components that correspond to timescales not likely to correspond to true incorporation events, in which case the further processing steps are optional.

In some cases, multiple passes are made through traces examining pulses at different timescales, from which a list of non-redundant pulses detected at such different time thresholds may be created. This typically includes analysis of unfiltered traces in order to minimize potential pulse overlap in time, thereby maximizing sensitivity to pulses with width at or near the highest frame rate of the camera. This allows the application of current oscillation color or other metrics to current pulses that inherently operate on different timescale. In particular, an analysis at longer timescales may establish trends not identifiable at shorter timescales, for example, identifying multiple short timescale pulses actually correspond to a single longer, discrete pulse.

In addition, some pulses may be removed from consideration/evaluation, where they may have been identified as the result of systematic errors, such as through spatial cross-talk of adjacent capacitive devices, or cross-talk between detection channels (to the extent such issues have not been resolved in a calibration processes). Typically, the calibration process will identify cross-talk coefficients for each capacitive device, and thus allow such components to be corrected.

In certain embodiments, a trace-file comprises L-weighted-sum (LWS) traces, where trace is optimized to have maximum pulse detection sensitivity to an individual capacitive label in the reaction mixture. This is not a deconvolved or multicomponent trace representation, and suffers from spectral cross-talk.

Classification of an extracted pulse into one of the 4(or N) capacitive labels is then carried out by comparing the extracted spectrum to the spectra of the capacitive labels sets established in a calibration process. A number of comparative methods may be used to generate a comparative metric for this process. For example, in some aspects, a $\chi^2$ test is used to establish the goodness of fit of the comparison. A suitable $\chi^2$ test is described, for example, in U.S. Patent Application 20120015825, incorporated herein by reference for all purposes.

Once the pulse spectrum is classified as corresponding to a particular label spectrum, that correlation is then used to assign a base classification to the pulse. As noted above, the base classification or "calling" may be configured to identify directly the capacitive-tag labeled base added to the extended primer sequence in the reaction, or it may be set to call the complementary base to that added (and for which the pulse spectrum best matches the label spectrum). In either case, the output will be the assignment of a base classification to each recognized and classified pulse. For example, a base classification may be assignment of a particular base to the pulse, or identification of the pulse as an insertion or deletion event.

In an ideal situation, once a pulse is identified as significant and its spectrum is definitively identified, a base is simply called on the basis of that information. However, as noted above, in typical sequencing runs, signal traces can include signal noise, such as missing pulses (e.g., points at which no pulse was found to be significant, but that correspond to an incorporation event) false positive pulses, e.g., resulting from nonspecifically adsorbed analogs or labels, or the like. Accordingly, pulse classification (also termed base classification) can in many cases involve a more complex analysis. As with pulse identification, above, base classification typically relies upon a plurality of different signal characteristics in assigning a base to a particular identified significant pulse. In many cases, two, three, five, ten or more different signal characteristics may be compared in order to call a base from a given significant pulse. Such characteristics include those used in identifying significant pulses as described above, such as pulse width or derivative thereof (e.g., smooth pulse width estimate, cognate residence time, or non-cognate residence time), pulse intensity, pulse channel, estimated average current amplitude of pulse, median current amplitude of all pulses in the trace corresponding to the same channel, background and/or baseline level of channel matching pulse identity, signal to noise ratio (e.g., signal to noise ratio of pulses in matching channel, and/or signal to noise ratio of each different channel), power to noise ratio, integrated counts in pulse peak, maximum signal value across pulse, pulse density over time (e.g., over at least about 1, 2, 5, 10, 15, 20, or 30 second window), shape of and distance/time to neighboring pulses (e.g., interpulse distance), channel of neighboring pulses (e.g., channel of previous 1, 2, 3, or 4 pulses and/or channel of following 1, 2, 3, or 4 pulses), similarity of pulse channel to the channel of one or more neighboring pulses, signal to noise ratio for neighboring pulses; spectral signature of the pulse, pulse centroid location, and the like, and combinations thereof. Typically, such comparison will be based upon standard pattern recognition of the metrics used as compared to patterns of known base classifications, yielding base calls for the closest pattern fit between the significant pulse and the pattern of the standard base profile.

Comparison of pulse metrics against representative metrics from pulses associated with a known base identity will typically employ predictive or machine learning processes. In particular, a "training" database of "N previously solved cases" is created that includes the various metrics set forth above. For example, a vector of features is analyzed for each pulse, and values for those features are measured and used to determine the classification for the pulse, e.g., an event corresponding to the pulse, e.g., an incorporation, deletion, or insertion event. As used herein, an incorporation event refers to an incorporation of a nucleotide complementary to a template strand, a deletion event corresponds to a missing pulse resulting in a one position gap in the observed sequence read, and an insertion event corresponds to an extra pulse resulting in detection of a base in the absence of incorporation. For example, an extra pulse can be detected when a polymerase binds a cognate or noncognate nucleotide but the nucleotide is released without incorporation into a growing polynucleotide strand. From that database, a learning procedure is applied to the data in order to extract a predicting function from the data. A wide variety of learning procedures are known in the art and are readily applicable to the database of pulse metrics. These include, for example, linear/logistic regression algorithms, neural networks, kernel methods, decision trees, multivariate splines (MARS), multiple additive regression trees (MART™), support vector machines.

In addition to calling bases at pulses identified as significant, the present methods also allow for modeling missing pulses. For example, conditional random fields (CRF) are probabilistic models that can be used to in pulse classification (see, e.g., Lafferty, et al. (2001) Proc.Intl. Conf. on Machine Learning 01, pgs 282-289, incorporated herein by reference in its entirety for all purposes). A CRF can also be conceptualized as a generalized Hidden Markov Model (HMM), some examples of which are described elsewhere herein and are well known in the art. The present invention includes the use of CRFs to model missing bases in an observed pulse trace. In addition to base calling, algorithms for consensus generation and sequence alignment can be used to obtain further information from the sequencing methods described herein.

Methods for calling bases, consensus generation, and sequence alignment are described, for example, in the following patents and applications, which are incorporated herein for all purposes: U.S. Pat. No. 7,995,202 Methods and Systems for Simultaneous real-time monitoring of optical signals from multiple sources; U.S. Pat. No. 7,626,704 Methods and systems for simultaneous real-time monitoring of optical signals from multiple sources; U.S. Pat. No. 8,182,993 Methods and Processes for Calling Bases in Sequence by Incorporation Methods; U.S. Ser. No. 13/468,347 filed May 10, 2012, Algorithms for Sequence Determination; US 20120015825 Analytical Systems and Methods with Software Mask; US 20110257889 Sequence Assembly and Consensus Sequence Determination; US 20120052490 Methods and Systems for Monitoring Reactions; US 20100169026 Algorithms for Sequence Determination Processing the data. While the base identification and base calling algorithms in the above documents are typically described referring to optical systems, in light of the current specification, one of ordinary skill in the art would understand how to bring such methods to bear in the capacitive sequencing systems and methods of the present invention.

Polymerase-Nucleic Acid Complex

The polymerase-enzyme complex of the invention comprises a nucleic acid polymerase enzyme associated with a template molecule. The template also typically has a primer hybridized to it, while some polymerase enzymes can initiate nucleic acid synthesis without the addition of an external primer. While many enzyme-substrate interactions are transient, some polymerase enzymes can form relatively stable complexes with nucleic acids that can be manipulated, purified, and then subsequently used to carry out nucleic acid synthesis. For example, DNA polymerases having relatively high processivity can have strong associations with template nucleic acid molecules. An exemplary DNA Polymerase is phi-29 DNA polymerase. Methods for forming and manipulating polymerase-nucleic acid complexes are described, for example in copending U.S. Patent Application entitled Purified Extended Polymerase/Template Complex for Sequencing" 61/385,376, filed Sep. 22, 2010 and U.S. patent application Ser. No. 13/427,725 filed Mar. 22, 2012 entitled "Isolation of Polymerase-Nucleic Acid Complexes" which is incorporated by reference herein in its entirety for all purposes.

The polymerase-nucleic acid complex will typically comprise a polymerase and a nucleic acid having a double stranded region. The polymerase-nucleic acid complex will generally have a primer from which a nascent nucleic acid strand will be produced complementary to a template strand of the nucleic acid. The primer is usually a short oligonucleotide that is complementary to a portion of the template nucleic acid. The primers of the invention can comprise naturally occurring RNA or DNA oligonucleotides. The primers of the invention may also be synthetic analogs. The primers may have alternative backbones as described above for the nucleic acids of the invention. The primer may also have other modifications, such as the inclusion of heteroatoms, the attachment of capacitive labels, or substitution with functional groups which will still allow for base pairing and for recognition by the enzyme. Primers can select tighter binding primer sequences, e.g., GC-rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. In some cases, the primer is added as a separate component to form the complex; in other cases, the primer can be part of the nucleic acid that used. For example, in some cases priming can begin at a nick or a gap in one strand of a double-stranded nucleic acid.

The template nucleic acid can be derived from any suitable natural or synthetic source. In preferred embodiments, the template comprises double stranded DNA, but in some circumstances double-stranded RNA or RNA-DNA heteroduplexes can be used. The template nucleic acid can be genomic DNA from eukaryotes, bacteria, or archaea. The template nucleic acid can be cDNA derived from any suitable source including messenger RNA. The template nucleic acid can comprise a library of double stranded segments of DNA. The template nucleic acid can be linear or circular. For example, the nucleic acid can be topologically circular and have a linear double stranded region. A circular nucleic acid can be, for example, a gapped plasmid. In some embodiments the nucleic acid is a double stranded linear DNA having a gap in one of the strands. The gap provides a site for attachment of the polymerase enzyme for nucleic acid synthesis. The linear double stranded DNA having a double-stranded DNA adaptor can be made by ligation of DNA fragment to an adaptor through blunt end—ligation or sticky end ligation. The ligation produces a linear DNA having a gap close to the 5' end of one or both of the strands. The gap can be any suitable width. For example, the gap can be from 1 to 50 bases, from 2 to 30 bases, or from 3 to 12 bases.

The terms "nucleic acid" or "oligonucleotide" or grammatical equivalents herein mean at least two nucleotides covalently linked together. A nucleic acid of the present invention will generally contain phosphodiester bonds, although in some cases, nucleotide analogs are included that may have alternate backbones, comprising, for example, phosphoramide, phosphorothioate, phosphorodithioate, and peptide nucleic acid backbones and linkages. Other analog nucleic acids include those with positive backbones, non-ionic backbones, and non-ribose backbones, including those described in U.S. Pat. Nos. 5,235,033 and 5,034,506. The template nucleic acid may also have other modifications, such as the inclusion of heteroatoms, the attachment of capacitive labels, or substitution with functional groups which will still allow for base pairing and for recognition by the enzyme.

The template sequence may be provided in any of a number of different format types depending upon the desired application. The template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008. Alternate functional circular constructs are also described in U.S. patent application Ser. No. 12/383,855, filed Mar. 27, 2009, and U.S. Pat. No. 8,153,375 Compositions and Methods for Nucleic Acid Sequencing; U.S. Pat. No. 8,003,330 Error-Free Amplification of DNA for Clonal Sequencing; and Ser. No. 13/363,066 filed Jan. 31, 2012 Methods and Compositions for Nucleic Acid Sample Preparation, the full disclosures of each of which are incorporated herein by reference in their entirety for all purposes.

Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

The nucleic acids can comprise a population of nucleic acids having universal sequence regions that are common to all of the nucleic acids in the population and also have specific regions that are different in the different members of the population. The current invention allows for capturing and isolating polymerase-nucleic acid complexes using either the universal or the specific regions.

While in many cases nucleic acid synthesis is describe herein as extending from a primer, it is to be understood that some polymerases do not require an added external primer, and can be initiated using terminal protein. Polymerases that can be initiated using terminal protein include phi-29 polymerase.

Polymerase Enzymes

Polymerase enzymes useful in the invention include polymerases mutated to have desirable properties for sequencing. For example, suitable enzymes include those taught in, e.g., 61/593,569 filed Feb. 1, 2012 Recombinant Polymerases with Increased Phototolerance; US 20120034602 Recombinant Polymerases for Improved Single Molecule Sequencing; US 20100093555 Enzymes Resistant to Photodamage; US 20110189659 Generation of Modified Polymerases for Improved Accuracy in Single Molecule Sequencing; US 20100112645 Generation of Modified Polymerases for Improved Accuracy in Single Molecule Sequencing; US 2008/0108082 Polymerase enzymes and reagents for enhanced nucleic acid sequencing; US 20110059505 Polymerases for Nucleotide Analogue Incorporation; and U.S. Provisional Patent No. 61/708,469 filed Oct. 1, 2012, all of which are incorporated by reference herein for all purposes. The modified polymerases can have modified properties such as e.g., decreased branch fraction formation, improved specificity, improved processivity, altered rates, improved retention time, improved stability of the closed complex, etc.

In addition, the polymerases can be further modified for application-specific reasons, such as to increase photostability, e.g., as taught in U.S. patent application Ser. No. 12/384,110 filed Mar. 30, 2009, by Keith Bjornson et al. entitled "Enzymes Resistant to Photodamage," to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

The polymerase enzymes used in the invention will generally have strand-displacement activity. Many polymerases have this capability, and it is useful in the context of the current invention for opening up and exposing the regions of a nucleic acid sample for capture by a hook molecule. In some cases, strand displacement is part of the polymerase enzyme itself. In other cases, other cofactors or co-enzymes can be added to provide the strand displacement capability.

DNA Polymerases

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y) which are incorporated by reference herein for all purposes. For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1): reviews 3002.1-3002.4; and Steitz (1999) "DNA polymerases: structural diversity and common mechanisms" J Biol Chem 274:17395-17398, which are incorporated by reference herein for all purposes. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296) which are incorporated by reference herein for all purposes. In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.) which are incorporated by reference herein for all purposes. Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, E. coli DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204 which are incorporated by reference herein for all purposes. Alternately, the modified recombinant DNA polymerase can be homologous to other Φ29-type DNA polymerases, such as B103, GA-1, PZA, Φ15, BS32, M2Y, Nf, GI, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. patent application Ser. No. 12/924,701, filed Sep. 30, 2010; and Ser. No. 12/384,112, filed Mar. 30, 2009 which is incorporated by reference herein for all purposes.

RNA Dependent RNA Polymerases

In some embodiments, the polymerase enzyme that is used for sequencing is an RNA polymerase. Any suitable RNA polymerase (RNAP) can be used including RNA polymerases from bacteria, eukaryotes, viruses, or archea. Suitable RNA polymerases include RNA Pol I, RNA Pol II, RNA Pol III, RNA Pol IV, RNA Pol V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors. There are many proteins that can bind to RNAP and modify its behavior. For instance, GreA and GreB from E. coli and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e., they help RNAP choose whether or not to express certain genes. RNA dependent RNA polymerases (RNA replicases) may also be used including viral RNA polymerases: e.g. polioviral 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or compositions of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Immobilization of the Polymerase-Template Complex

The polymerase-template complex can be attached to the surface by binding the polymerase, the template nucleic acid, or a primer. The binding can be either covalent or non-covalent. In some cases, an $SiO_2$ region of the surface can be selectively functionalized to bind the polymerase complex. The selective functionalization of $SiO_2$ can be done, for example, using silane chemistry. For example, the $SiO_2$ portion of the surface can be selectively treated with a biotin functionalized silane, and the surface can be treated with an enzyme complex attached to streptavidin. The streptavidin-polymerase-template complex will bind specifically to the biotin on the $SiO_2$ portions of the surface providing selective binding. See e.g. U.S. Pat. No. 8,193,123 which is incorporated herein by reference for all purposes. In some cases, small regions, e.g. balls, islands, or pits can be made on the surface that allow only a small number, and in some cases allow only a single polymerase enzyme to bind. The creation of regions to bind a single polymerase enzyme complex are described, for example in U.S. Patent Application 20100009872 Single Molecule Loading Methods and Compositions; and U.S. Patent Application 20110257040 Nanoscale Apertures Having Islands of Functionality which are incorporated herein by reference for all purposes. DNA molecules typically possess a strong negative charge and can thus be directed using electric fields in aqueous solution. Because the devices of the instant invention contemplate arrays of electrodes with means of applying electric potentials and simultaneously measuring currents from proximate labels, the capability exists to use the potential-setting capacity to attract polymerases bound to DNA molecules to the electrode region and then either simultaneously or in alternating periods check to see if a polymerase has bound the system. In this way each active device can be loaded with a single polymerase by ceasing the attractive potential when the binding of a DNA-Polymerase complex is detected.

The immobilization of a component of an analytical reaction can be engineered in various ways. For example, an enzyme (e.g., polymerase, reverse transcriptase, kinase, etc.) may be attached to the substrate at a reaction site, e.g., proximate to a nanoscale electrode. In other embodiments, a substrate in an analytical reaction (for example, a nucleic acid template, e.g., DNA, RNA, or hybrids, analogs, and mimetics thereof, or a target molecule for a kinase) may be attached to the substrate at a reaction site. Certain embodiments of template immobilization are provided, e.g., in U.S. patent application Ser. No. 12/562,690, filed Sep. 18, 2009 and incorporated herein by reference in its entirety for all purposes. One skilled in the art will appreciate that there are many ways of immobilizing nucleic acids and proteins, whether covalently or non-covalently, via a linker moiety, or tethering them to an immobilized moiety. These methods are well known in the field of solid phase synthesis and microarrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to one or more reaction components can also be employed as the binding moieties. In addition, a silyl moiety can be attached to a nucleic acid directly to a substrate such as glass using methods known in the art.

In some embodiments, a nucleic acid template is immobilized onto a reaction site (e.g., proximate to a capacitive electrode) by attaching a primer comprising a complementary region at the reaction site that is capable of hybridizing with the template, thereby immobilizing it in a position suitable for monitoring. In certain embodiments, an enzyme complex is assembled, e.g., by first immobilizing an enzyme component. In other embodiments, an enzyme complex is assembled in solution prior to immobilization. Where desired, an enzyme or other protein reaction component to be immobilized may be modified to contain one or more epitopes for which specific antibodies are commercially available. In addition, proteins can be modified to contain heterologous domains such as glutathione S-transferase (GST), maltose-binding protein (MBP), specific binding peptide regions (see e.g., U.S. Pat. Nos. 5,723,584, 5,874, 239 and 5,932,433), or the Fc portion of an immunoglobulin. The respective binding agents for these domains, namely glutathione, maltose, and antibodies directed to the Fc portion of an immunoglobulin, are available and can be used to coat the surface of a capacitive device of the present invention. The binding moieties or agents of the reaction components they immobilize can be applied to a support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

The various components of the surface of the capacitive devices can be selectively treated in order to bind the polymerase-template complex to a specific portion of the substrate. Selective treatment and immobilization is described, for example, in U.S. Pat. Nos. 5,624,711; 5,919, 523; Hong et al., (2003) Langmuir 2357-2365; U.S. Pat. Nos. 5,143,854; 5,424,186; 8,137,942; 7,993,891 Reactive surfaces, substrates and methods of producing and using same; U.S. Pat. Nos. 7,935,310; 7,932,035 7,931,867 Uniform surfaces for hybrid material substrates and methods of making and using same; and U.S. Pat. No. 8,193,123 Articles having localized molecules disposed thereon and methods of producing same, all of which are incorporated herein by reference for all purposes.

The polymerase complex is attached proximate to the electrode or electrodes of the capacitive device. The attachment is made close enough to the electrode(s) that the capacitive label on a nucleotide analog held in the active site of the enzyme can extend close enough to the electrode to allow for capacitive detection. The polymerase complex can be attached for example from about 1 nm to about 100 nm from a capacitive electrode, from about 2 nm to about 50 nm from a capacitive electrode, or from about 4 nm to about 20 nm from a capacitive electrode. For the two electrode capacitive device, the polymerase template complex is typically bound to the insulating region between the two electrodes. For the single electrode configuration, the polymerase template complex can be bound, for example, to a region near the electrode, to the electrode, or to an insulating region within or on top of the electrode.

Conditions for Nucleic Acid Synthesis

The conditions required for nucleic acid synthesis are well known in the art. The polymerase reaction conditions include the type and concentration of buffer, the pH of the reaction, the temperature, the type and concentration of salts, the presence of particular additives that influence the kinetics of the enzyme, and the type, concentration, and relative amounts of various cofactors, including metal cofactors. For carrying out the methods of the instant invention, the conditions for polymerase mediated nucleic acid synthesis must also be compatible with conditions for measuring capacitance near the nanoelectrodes. One aspect of carrying out capacitance measurements in solution is controlling the ionic strength of the medium. It is know that polymerase enzymes can effectively operate over a range of ionic strengths, and that the ionic strength can be varied by changing the levels of monovalent ions such as $Li+$, $Na+$, $K+$, $Rb+$, or $Cs+$. As has been shown the amount of one or more of these cations can have an effect on the kinetics of the polymerase, and that the kinetic behavior can be tuned by varying the relative amounts of these ions. Using combinations of these ions, conditions can be chosen where both the kinetic parameters of the enzyme, and the ionic strength for capacitive detection can be useful for the instant methods. See, e.g. U.S. Patent Application 20120009567 which is incorporated herein by reference for all purposes.

Enzymatic reactions are often run in the presence of a buffer, which is used, in part, to control the pH of the reaction mixture. Buffers suitable for the invention include, for example, TAPS (3-{[tris(hydroxymethyl)methyl] amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the rate of the polymerase reaction. The temperature of the reaction can be adjusted to enhance the performance of the system. The reaction temperature may depend upon the type of polymerase which is employed.

Nucleotide Analogs

Components of the sequencing reaction mixture include nucleotides or nucleotide analogs. For the methods of the instant invention, at least some of the nucleotide analogs have capacitive labels attached to them. The nucleotide analogs comprising capacitive labels are generally constructed in order to enhance the impedance signal when the label is in the enzyme active site.

Typically the nucleotide analogs of the invention have the following structure:

Base-Sugar-PP-Linker—Impedance Label wherein Base is a nucleobase, Sugar is a sugar such as ribose or deoxyribose, PP is a polyphosphate moiety, Linker is a linking group, and the Impedance Label is a group that is detectable by the nanoscale electronic element. The Impedance label can be for example, a capacitive label or a conductivity label as described herein.

Typically there are four nucleotides in the sequencing reaction mixture corresponding to A, G, T, and C for DNA and A, G, C, U for RNA. In some cases, a $5^{th}$, $6^{th}$, or more base is added. In some cases all of the nucleotide analogs have a capacitive label, in other cases, fewer than all of the nucleotides will have a capacitive label. In still other cases all of the different nucleotide analog types will carry a capacitive label, but a particular capacitive label will be assigned to more than one base type. Typically each of the types of nucleotide will have a nucleotide that is different and can be distinguished from the other nucleotides, for example the other three nucleotides. As described herein, the different nucleotides can have different impedance intensities, different impedance versus frequency characteristics, different current versus time characteristics (current oscillation color), or different combinations of two or more of the above.

The Base is a nucleobase which can be one of the natural bases, a modified natural base or a synthetic base. The Base will selectively associate with its complementary base on the template nucleic acid such that it will be inserted across from its complementary base. The sugar is a group that connects the base to the polyphosphate group. It is typically either ribose or deoxyribose, but can be any sugar or other group that allows for the complexation and incorporation of the nucleotide analog into the growing strand. PP is a polyphosphate group generally from 2 to 20 phosphates in length, typically from 3 to 12 phosphates in length, and in some preferred embodiments from 4 to 10 phosphates in length. The nucleotide analog can have for example 4, 5, 6, 7 or more phosphate groups. Such nucleotides have been described, for example, in U.S. Pat. Nos. 6,936,702 and 7,041,812, which are incorporated herein by reference for all purposes. Together, the Base, Sugar and PP portion of the nucleotide analog is sometimes referred to as the nucleotide portion or nucleoside phosphate portion.

As used in the art, the term nucleotide refers both to the nucleoside triphosphates that are added to a growing nucleic acid chain in the polymerase reaction, or can refer to the individual units of a nucleic acid molecule, for example the units of DNA and RNA. Herein, the term nucleotide is used consistently with its use in the art. Whether the term nucleotide refers to the substrate molecule to be added to the growing nucleic acid or to the units in the nucleic acid chain can be derived from the context in which the term is used.

The Linker is a linking group that connects the capacitive label to the nucleotide portion of the nucleotide analog. The linker is typically a long linear or branched moiety whose length and flexibility is used to control the diffusion of the nucleotide analog that is held within the polymerase enzyme while it is being incorporated. The length of the linker is, for example, from between 2 nm and 200 nm when fully extended. It is understood that a long molecule such as a polymer will not spend much time, if any, in its fully extended configuration. The linker can be made up of groups including alkanes, ethers, alcohols, amines, acids, sulfates, sulfonates, phosphates, phosphonates, amides, esters, peptides, and sugars. The groups on the linker can be neutral, positively charged, or negatively charged. In some cases, the linker comprises polyethylene glycol (PEG). It is desirable that the linker have a fixed length (i.e. not be polydisperse) such that the size of any analog molecule in the population will be the same. It is generally desirable that the linker be water compatible.

The length of the linker can be chosen for performance with the particular geometry of the capacitive device that is used. The capacitive label is tethered to the substrate through the nucleotide analog (comprising the linker), the enzyme and the attachment moiety. The length of this complete tether and the distance of the polymerase complex from the nanoscale electronic element such as capacitive electrodes can be used in order to select the appropriate linker.

The inductive, capacitive, or conductivity label is attached to the nucleotide portion of the nucleotide analog through the linker and phosphate. The linker is typically attached to the terminal phosphate in the polyphosphate moiety, but in some cases can be connected to a phosphate in the polyphosphate chain that is not the terminal phosphate. The linker should be attached to a phosphate that is cleaved on the act of the polymerase enzyme of nucleotide incorporation. The polymerase enzyme cleaves the polyphosphate between the alpha and beta phosphates, thus, the linker should be connected to the beta (second) phosphate or greater.

The impedance label may be made up of one or more impedance moieties. Acceptable impedance labels or moieties can comprise organic compounds, organometallic compounds, nanoparticles, metals, or other suitable substituent. In some cases nanoparticles.

Kinetic Measurements—Modified Base Detection

The methods of the invention provide for measuring the incorporation of nucleotides into a growing chain in real time. The real time measurements allow for the determination of enzyme kinetics, which are can be sensitive to template characteristics such as secondary structure, and modified bases. The ability to detect modifications within nucleic acid sequences is useful for mapping such modifications in various types and/or sets of nucleic acid sequences, e.g., across a set of mRNA transcripts, across a chromosomal region of interest, or across an entire genome. The modifications so mapped can then be related to transcriptional activity, secondary structure of the nucleic acid, siRNA activity, mRNA translation dynamics, kinetics and/or affinities of DNA- and RNA-binding proteins, and other aspects of nucleic acid (e.g., DNA and/or RNA) metabolism.

In certain aspects of the invention, methods are provided for identification of a modification in a nucleic acid molecule using real time capacitive sequencing. In general, a template nucleic acid comprising the modification and an enzyme capable of processing the template are provided. The template nucleic acid is contacted with the enzyme, and the subsequent processing of the template by the enzyme is monitored. A change in the processing is detected, and this change is indicative of the presence of the modification in the template. Exemplary modifications that can be detected by the methods of the invention include, but are not limited to methylated bases (e.g., 5-methylcytosine, N6-methyladenosine, etc.), pseudouridine bases, 7,8-dihydro-8-oxoguanine bases, 2'-O-methyl derivative bases, nicks, apurinic sites, apyrimidic sites, pyrimidine dimers, a cis-platen crosslinking products, oxidation damage, hydrolysis damage, bulky base adducts, thymine dimers, photochemistry reaction products, interstrand crosslinking products, mismatched bases, secondary structures, and bound agents. In preferred embodiments, nucleotides or analogs thereof that are incorporated into a nascent strand synthesized by the enzyme are distinctly labeled to allow identification of a sequence of specific nucleotides or nucleotide analogs so incorporated. Labels are linked to nucleotides or nucleotide analogs through a phosphate group, e.g., a phosphate group other than the alpha phosphate group. As such, the capacitive labels are removed from the nucleotide or nucleotide analog upon incorporation into the nascent strand. Techniques for kinetically identifying modified bases are described, for example in U.S. Patent Application 20110183320 Classification of Nucleic Acid Templates which is incorporated herein by reference for all purposes.

The term "modification" as used herein is intended to refer not only to a chemical modification of a nucleic acids, but also to a variation in nucleic acid conformation or composition, interaction of an agent with a nucleic acid (e.g., bound to the nucleic acid), and other perturbations associated with the nucleic acid. As such, a location or position of a modification is a locus (e.g., a single nucleotide or multiple contiguous or noncontiguous nucleotides) at which such modification occurs within the nucleic acid. For a double-stranded template, such a modification may occur in the strand complementary to a nascent strand synthesized by a polymerase processing the template, or may occur in the displaced strand. Although certain specific embodiments of the invention are described in terms of 5-methylcytosine detection, detection of other types of modified nucleotides (e.g., $N^6$-methyladenosine, $N^3$-methyladenosine, $N^7$-methylguanosine, 5-hydroxymethylcytosine, other methylated nucleotides, pseudouridine, thiouridine, isoguanosine, isocytosine, dihydrouridine, queuosine, wyosine, inosine, triazole, diaminopurine, β-D-glucopyranosyloxymethyluracil (a.k.a., β-D-glucosyl-HOMedU, β-glucosyl-hydroxymethyluracil, "dJ," or "base J"), 8-oxoguanosine, and 2'-O-methyl derivatives of adenosine, cytidine, guanosine, and uridine) are also contemplated. Further, although described primarily in terms of DNA templates, such modified bases can be modified RNA bases and can be detected in RNA (or primarily RNA) templates. These and other modifications are known to those of ordinary skill in the art and are further described, e.g., in Narayan P, et al. (1987) Mol Cell Biol 7(4):1572-5; Horowitz S, et al. (1984) Proc Natl Acad Sci U.S.A. 81(18):5667-71; "RNA's Outfits: The nucleic acid has dozens of chemical costumes," (2009) C&EN; 87(36): 65-68; Kriaucionis, et al. (2009) Science 324 (5929): 929-30; and Tahiliani, et al. (2009) Science 324 (5929): 930-35; Matray, et al. (1999) Nature 399(6737):704-8; Ooi, et al. (2008) Cell 133: 1145-8; Petersson, et al. (2005) J Am Chem Soc. 127(5):1424-30; Johnson, et al. (2004) 32(6):1937-41; Kimoto, et al. (2007) Nucleic Acids Res. 35(16):5360-9; Ahle, et al. (2005) Nucleic Acids Res 33(10):3176; Krueger, et al., Curr Opinions in Chem Biology 2007, 11(6):588); Krueger, et al. (2009) Chemistry & Biology 16(3):242; McCullough, et al. (1999) Annual Rev of Biochem 68:255; Liu, et al. (2003) Science 302(5646):868-71; Limbach, et al. (1994) Nucl. Acids Res. 22(12):2183-2196; Wyatt, et al. (1953) Biochem. J. 55:774-782; Josse, et al. (1962) J. Biol. Chem. 237:1968-1976; Lariviere, et al. (2004) J. Biol. Chem. 279:34715-34720; and in International Application Publication No. WO/2009/037473, the disclosures of which are incorporated herein by reference in their entireties for all purposes. Modifications further include the presence of non-natural base pairs in the template nucleic acid, including but not limited to hydroxypyridone and pyridopurine homo- and hetero-base pairs, pyridine-2,6-dicarboxylate and pyridine metallo-base pairs, pyridine-2,6-dicarboxamide and a pyridine metallo-base pairs, metal-mediated pyrimidine base pairs T-Hg(II)-T and C—Ag(I)—C, and metallo-homo-basepairs of 2,6-bis(ethylthiomethyl)pyridine nucleobases Spy, and alkyne-, enamine-, alcohol-, imidazole-, guanidine-, and pyridyl-substitutions to the purine or pyridimine base (Wettig, et al. (2003) J Inorg Biochem 94:94-99; Clever, et al. (2005) Angew Chem Int Ed 117:7370-7374; Schlegel, et al. (2009) Org Biomol Chem 7(3):476-82; Zimmerman, et al. (2004) Bioorg Chem 32(1):13-25; Yanagida, et al. (2007) Nucleic Acids Symp Ser (Oxf) 51:179-80; Zimmerman (2002) J Am Chem Soc 124(46): 13684-5; Buncel, et al. (1985) Inorg Biochem 25:61-73; Ono, et al. (2004) Angew Chem 43:4300-4302; Lee, et al. (1993) Biochem Cell Biol 71:162-168; Loakes, et al. (2009), Chem Commun 4619-4631; and Seo, et al. (2009) J Am Chem Soc 131:3246-3252, all incorporated herein by reference in their entireties for all purposes). Other types of modifications include, e.g, a nick, a missing base (e.g., apurinic or apyridinic sites), a ribonucleoside (or modified ribonucleoside) within a deoxyribonucleoside-based nucleic acid, a deoxyribonucleoside (or modified deoxyribonucleoside) within a ribonucleoside-based nucleic acid, a pyrimidine dimer (e.g., thymine dimer or cyclobutane pyrimidine dimer), a cis-platin crosslinking, oxidation damage, hydrolysis damage, other methylated bases, bulky DNA or RNA base adducts, photochemistry reaction products, interstrand crosslinking products, mismatched bases, and other types of "damage" to the nucleic acid. As such, certain embodiments described herein refer to "damage" and such damage is also considered a modification of the nucleic acid in accordance with the present invention. Modified nucleotides can be caused by exposure of the DNA to radiation (e.g., UV), carcinogenic chemicals, crosslinking agents (e.g., formaldehyde), certain enzymes (e.g., nickases, glycosylases, exonucleases, methylases, other nucleases, glucosyltransferases, etc.), viruses, toxins and other chemicals, thermal disruptions, and the like. In vivo, DNA damage is a major source of mutations leading to various diseases including cancer, cardiovascular disease, and nervous system diseases (see, e.g., Lindahl, T. (1993) Nature 362(6422): 709-15, which is incorporated herein by reference in its entirety for all purposes). The methods and systems provided herein can also be used to detect various conformations of DNA, in particular, secondary structure forms such as hairpin loops, stem-loops, internal loops, bulges, pseudoknots, base-triples, supercoiling, internal hybridization, and the like; and are also useful for detection of agents interacting with the nucleic acid, e.g., bound proteins or other moieties.

In some embodiments, five color DNA sequencing can be carried out by the capacitive sequencing methods of the invention. Five color sequencing generally utilizes a nucleotide analog having a base that preferentially associates with a fifth base in the template or an abasic site. Such five color sequencing is described for example in U.S. Patent Application 20110183320, which is incorporated herein by reference in its entirety for all purposes.

Monitoring Biological Reactions

While the nanoscale capacitive devices and systems of the invention are described throughout most of this application for use in nucleic acid sequencing, it is to be understood that the devices and systems can also find use in other analytical reactions including monitoring biological reactions in real time, in particular monitoring the interactions of biological molecules at the single molecule level. The ability to analyze such reactions provides an opportunity to study those reactions as well as to potentially identify factors and/or approaches for impacting such reactions, e.g., to stimulate, enhance, or inhibit such reactions.

The invention provides for observation of the interaction of two or more specifically interacting reactants at the single molecule (or single molecular complex) level in order to monitor the progress of the interaction separately from other interactions. In other words, a single immobilized reaction component can be monitored at a single reaction site on a support such that capacitive signals received from that reaction site are resolvable from other immobilized reaction components at other reaction sites on that support. In preferred embodiments, the methods monitor capacitive detectable labels with a nanoscale capacitive device, such that a single reactant comprising a capacitive detectable label is distinguishable from a different single reactant comprising a different capacitive detectable label. A plurality of analytical reactions may also be carried out in an array of capacitive devices. Analytical reactions in an array of capacitive devices can be carried out simultaneously, and may or may not be synchronized with one another. In such an array, multiple reactions can therefore be monitored simultaneously and independently.

The monitoring typically comprises providing the interaction with one or more signaling events that are indicative of one or more characteristics of that interaction. Such signaling events may comprise the retention of a capacitive labeled reactant proximate to a given capacitive device. For example, in some embodiments, the labels provide capacitive signals that are detected by a capacitive detection system operably linked to a reaction site at which the analytical reaction is taking place. As used herein, a reaction site is a location on or adjacent to a substrate at which an analytical reaction is monitored, and may refer to, e.g., a position on the substrate at which one or more components of an analytical reaction are immobilized or to a "detection volume" within which an analytical reaction is monitored. The detected signals are analyzed to determine one or more characteristics of the analytical reaction, e.g., initiation, termination, affinity, biochemical event (e.g., binding, bond cleavage, conformational change, etc.), substrate utilization, product formation, kinetics of the reaction (e.g., rate, time between subsequent biochemical events, time between the beginning/end of subsequent biochemical events, processivity, error profile, etc.), and the like.

These characteristics may generally be broken into two categories: reactant characteristic(s) and interaction characteristic(s). Reactant characteristic(s) includes characteristics of a particular reactant, e.g., type/identity of reactant, concentration of the reactant, a label on the reactant, etc. Interaction characteristic(s) includes characteristics of a given interaction between multiple reactants, e.g., rates, constants, affinities, etc., and is typically determined based on reaction data gathered during such an interaction. For example, some characteristics of a polymerization reaction include the identity of a monomer incorporated into a growing polymer, the rate of incorporation, length of time the polymerase is associated with the template, and the length of the polymer synthesized. In some embodiments, various different components of an analytical reaction (e.g., different types of monomers) are differentially labeled to allow each labeled component to be distinguished from other labeled components during the course of the reaction. For example, incorporation of monomer A into a polymer can be distinguished from incorporation of monomer B.

In certain preferred embodiments, multiple characteristics of a reaction are monitored and/or determined. For example, these may be multiple characteristics of one or more reaction components (e.g., identity, concentration, etc.; "reactant characteristic(s)"), one or more characteristics of an interaction between two or more reaction components (e.g., related to product formation, kinetics of the reaction, binding or dissociation constants, etc.; "interaction characteristic(s)"), or, preferably, a combination reactant characteristic(s) and interaction characteristic(s).

In some embodiments, a reaction mixture comprises a plurality of types of non-immobilized binding partners, and a characteristic determined is the particular type of one of the non-immobilized binding partners, e.g., that associates with a particular reaction site. Typically, the capacitive label is attached to the non-immobilized binding partner through a linking group as described herein such that the capacitive label on the non-immobilized binding partner will be sensed when it is interacting with the immobilized binding partner that is immobilized proximate to a nanoscale electrode or electrodes. In some embodiments, an array of reaction sites comprises a plurality of types of immobilized binding partners, each at a different reaction site, and a characteristic is determined that identifies which type of immobilized binding partner is located at each of the different reaction sites. In some embodiments, an array of reaction sites comprising a plurality of types of immobilized binding partners, each at a different reaction site, is contacted with a reaction mixture comprising a plurality of types of non-immobilized binding partners; characteristics determined during the reaction serve to both identify which of the types of immobilized binding partners is located at each reaction site and which of the types of non-immobilized binding partners associate with the immobilized binding partners. In some cases, the specificity of the interaction between the non-immobilized and immobilized binding partners is high enough that detection of a label on a non-immobilized binding partner residing at a particular reaction site is sufficient to identify the immobilized binding partner at that reaction site. In some embodiments, a characteristic is determined that quantifies a particular aspect of an interaction between reaction components, e.g., affinity between an immobilized binding partner and a non-immobilized binding partner, a rate of catalysis of a reaction, or other aspects of the interaction. In some cases, different capacitive signaling events (e.g., different capacitive labels on one or more reaction components) are used to monitor or determine different characteristics of a reaction under observation, but in some embodiments a single capacitive signaling event can provide more than one type of characteristic information. For example, if a non-immobilized binding partner has a capacitive label that not only identifies it from a plurality of different non-immobilized binding partners, but also provides kinetic information about the reaction based on various parameters monitored in real time, e.g., the time it takes for binding to occur, the time it remains associated with the reaction site, the on/off rate, etc.

In some embodiments, multiple different interactions or reactions can occur and be monitored simultaneously or sequentially, where each individual interaction is monitored separately from every other, e.g. in an electronic element such as a capacitive device or a nanoFET, such that there is resolution between different interactions under observation. For example, multiple different non-immobilized reaction components may simultaneously or sequentially interact with an immobilized reaction component; e.g., the multiple different non-immobilized reaction components can be different non-immobilized binding partners for an immobilized binding partner, or different agents that may alter an interaction between two reaction components, or different monomers for incorporation into a polymer being synthesized at the reaction site. In other embodiments, an interaction between a non-immobilized reaction component and a product of a synthesis reaction occurs during the synthesis reaction, e.g., once the product is suitable for such interaction. For example, the product may need to be of a certain length, or in a certain conformation (e.g., in a particular higher-order structure) to be suitable for interaction with the non-immobilized reaction component. Alternatively, a synthesis reaction can be performed at a reaction site, and subsequently exposed to a reaction mixture comprising non-immobilized reaction components that can then interact with the product of the synthesis reaction, which is preferably immobilized at the reaction site. In preferred embodiments, the synthesis reaction is monitored to determine characteristics of the product (e.g., length, chemical composition, etc.) being synthesized. Knowledge of characteristics of the product of synthesis combined with the detection of an interaction with a particular reaction component provides additional characteristics, e.g., the binding site for the particular reaction component. Examples of biological interactions that can be measured with the capacitive devices and systems of the invention are described, for example, in U. S. 20100323912 Patent Application Real-Time Analytical Methods and Systems which is incorporated herein by reference for all purposes.

Systems

In some aspects, the invention provides systems for carrying out real time single molecule electronic sequencing using nanoscale electronic elements such as capacitive or nanoFET devices. A capacitive or nanoFET measuring system is used to monitor the nanoscale electronic element over time allowing for the determination of whether a nucleotide analog having a capacitive label is associating with the enzyme. That is, the nanoscale electronic element and enzyme are configured such that the freely diffusing capacitive or conductive labeled nucleotide analogs in the solution are not substantially detected at the nanoscale electronic element. Only when a label is brought into the vicinity of the nanoscale electronic element due to its association with the polymerase enzyme is the label detected and identified as an incorporated nucleotide. One distinction between the freely diffusing nucleotide analogs and an analog in the active site of the enzyme is the amount of time spent proximate to the nanoscale electronic element. Diffusing nucleotide analogs will be quickly diffusing in and out of the vicinity of the nanoscale electrode, while the nucleotide analog to be incorporated will spend a longer amount of time, for example on the order of milliseconds proximate to the nanoscale electrode. Thus, the nanoscale electronic measuring system will detect the presence of a nucleotide analog which is to be incorporated into the growing nucleic acid chain while it is in the active site of the enzyme. When the nucleotide is incorporated into the growing strand, the capacitive label, which is attached to the phosphate portion of the nucleotide analog is cleaved and diffuses away from the enzyme and the electrode. Thus, the capacitive measuring system determines the presence of the analog in the active site prior to incorporation. In addition, the identity of the distinct label is determined, e.g. by the magnitude of a change in impedance. As the polymerase reaction continues and is monitored by the nanoscale electronic measuring system, the sequence of the template nucleic acid can be determined by the time sequence of incorporation of the complementary nucleotide analog into the growing nucleic acid strand.

The systems of the invention include a chip comprising an array of nanoscale electronic devices as described herein that is reversibly mated with other system components. The chip with array of nanoscale electronic devices can be a single use chip or the chip can be used multiple times. The system typically has a housing into which the chip is placed. The housing has electrical connectors that provide reversible connections to the electrical connections on the chip. Sockets that provide reliable reversible electrical connections to chips inserted into the socket are well known. Electrical connections to the top, sides, bottom, or a combination of these sides can be used.

When the chip is inserted into the housing, the system provides a fluid reservoir to which fluid comprising the sequencing reaction mixture is added. In some cases, the fluid reservoir is included as part of the chip. In some cases, part of the fluid reservoir is associated with the housing, such that the insertion of the chip forms the reservoir. The fluid reservoir can be, for example a well or a chamber into which fluid can be introduced. The introduced fluid sequencing reaction mixture comes into contact with the capacitive devices on the surface of the chip. The system will typically include environmental control components including temperature control and control of a vapor phase above the fluid. The chemical makeup and the temperature of the vapor can be controlled, for example by providing a flow of inert gas over the reaction mixture to minimize oxidation of the sample. In some cases the system can have fluid handling systems for delivering and removing components to the fluid reservoir before, during, or after performing the sequencing reaction.

In some cases the fluid reservoir will also provide contact of the sequencing reaction mixture with the either or both a reference electrode or counter electrode. As described above, in order to carry out the method, in some cases a reference electrode, a counter electrode, or both are used. In some one or more of these electrodes are on the chip. Where the reference electrode and/or counter electrode are used, and not on the chip, they are brought into contact with the sequencing reaction mixture in the fluid reservoir.

Connected to the chip through the connectors on the housing are the electronics for providing voltage to the electronic element and for measuring the impedance changes, for example, a current/voltage source and a meter. For example, for capacitive measurements, the source provides the current and voltage to bring the electrodes to the proper alternating current signal over time to carry out the methods of the invention. The meter is used to measure the impedance and/or capacitance. In some cases, the source and meter are combined into a single unit. In some cases each of the electronic elements in the array on the chip are addressed by a separate source and separate meter component within the system. In some cases, multiplexing is used so a single source can drive multiple electronic elements. In some cases a single source will drive all of the electronic elements on a chip, while each of the electronic elements is measured with a separate meter component. Any suitable combination of sources and meters can be used.

A computer control and analysis system is used to control both the input voltages and currents and to provide computer-implemented control functions, e.g., controlling robotics, environmental conditions, and the state of various components of the system. The computer control system also includes components for computational data analysis (e.g., for single molecule sequencing applications, determining and characterizing nucleotide incorporation events). As described above, in some cases, some of the control functions can be implemented on the chip, in particular controlling source wave functions, or handling electrical signals from the capacitive devices on the chip. In some cases the computer control and analysis system provides substantially all of the control of the signals to and from the chip, and the chip simple acts as a electronic element from which impedance, capacitance, and or conductivity information is extracted. In some cases, the chip can take on some of the functionality of control and analysis. The chip can process the analog data from the electronic elements. The chip can also have analog to digital components, and can perform analysis and storage functions for the digital signals. The decision on how much functionality is implemented on the chip and how much is retained with the computer control and analysis system can be made based on the relative functionality gained versus the cost of adding the functionality.

Also provided is a user interface operatively coupled to the components for computational data, permitting a user of the system to initiate and terminate an analysis, control various parameters (e.g., with respect to analysis conditions, sequencing reaction mixture environment, etc.), and manage/receive data (e.g., nucleic acid sequence data) obtained by the system. In some aspects, the user interface is attached the computer control and analysis system. Additionally, remote user interfaces can be provided that are in communication with the overall system via a wireless network. Such user input devices may include other purposed devices, such as notepad computers, e.g., Apple iPad, or smartphones running a user interface application. Optionally, the user interface includes a component, e.g., a data port, from which the user can receive data obtained by the analysis system to a portable electronic storage medium for use at location other than the location of the substrate analysis system.

Aspects of the present invention are directed to machine or computer implemented processes, and/or software incorporated onto a computer readable medium instructing such processes. As such, signal data generated by the reactions and systems described above, is input or otherwise received into a computer or other data processor, and subjected to one or more of the various process steps or components set forth herein. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or MacIntosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C #, NET, Visual Basic, Python, JAVA, CGI, and the like.

While described in terms of a particular sequencing by incorporation process or system, it will be appreciated that certain aspects of the processes of the invention may be applied to a broader range of analytical reactions or other operations and varying system configurations than those described for exemplary purposes.

EXAMPLES

Example 1—Real-Time Capacitive Sequencing

A capacitive sequencing chip is produced having nine separate nano-electrode pairs. Onto a silicon substrate is deposited, patterned, and etched a first layer of platinum, a layer of $SiO_2$, a second layer of platinum, and a layer of silicon nitride. This process produces a substrate having nine nano-electrode pairs having electrical interconnects extending to the edge of the silicon substrate as shown in FIG. 5. The thickness of the $SiO_2$ layer is about 4 nanometers. The thickness of the platinum electrode layers is about 10 nanometers. The electrical interconnects provide for connecting the nano-electrodes to the off-chip electronics.

After surface treatment of the chip with an oxygen plasma and washing, the chip is chemically treated to specifically bias the surface for selective attachment of a polymerase enzyme to the $SiO_2$ layer between the nanoscale electrodes as described in U.S. Pat. No. 8,193,123. The chip is treated with a solution of silane-PEG-biotin in order which preferentially provides surface attached biotin to the $SiO_2$ layer between the electrodes.

Lambda DNA is fragmented, and hairpin adaptors s are ligated to the ends of the fragments to produce a library of circular templates each having a complementary double stranded region closed on each end with a hairpin as described in U.S. Pat. No. 8,153,375. A primer is added to the library that hybridizes with a region within the hairpin adaptor to provide a primed DNA library.

A phi-29 DNA polymerase selected for carrying out DNA synthesis at rates appropriate for detection is prepared as described in U.S. Patent Application 20110189659. The DNA polymerase has a biotin tag sequence as described in U.S. Patent Application 20110306096. The DNA polymerase is treated with an excess of streptavidin in order to produces a solution of DNA polymerase-streptavidin. The DNA polymerase-streptavidin is mixed with the library of primed circular DNA constructs under conditions whereby a library of polymerase-template complexes is formed.

The capacitive sequencing chip is mounted within a capacitive sequencing system such that a reservoir is formed above the chip allowing for the introduction of a sequencing solution which comes into contact with the nano-electrode pairs on the chip. The capacitive sequencing system has socket with receives the sequencing chip such that the electrical interconnects on the chip mate with connectors on the socket to allow for conducting electrical signals to and from the nano-electrodes.

The library of polymerase template complexed is diluted and applied to the substrate such that the streptavidin on the polymerase binds to the biotin groups attached to the $SiO_2$ layer between the nano-electrodes. The level of dilution is chosen such that at least some of the nano electrode pairs have a single active enzyme bound to it. This can be done by serial dilution. Poisson statistics suggests that under the appropriate dilution, more than a third of the nanoelectrode pairs can have a single polymerase bound at the optimal dilution level.

Figure 10:
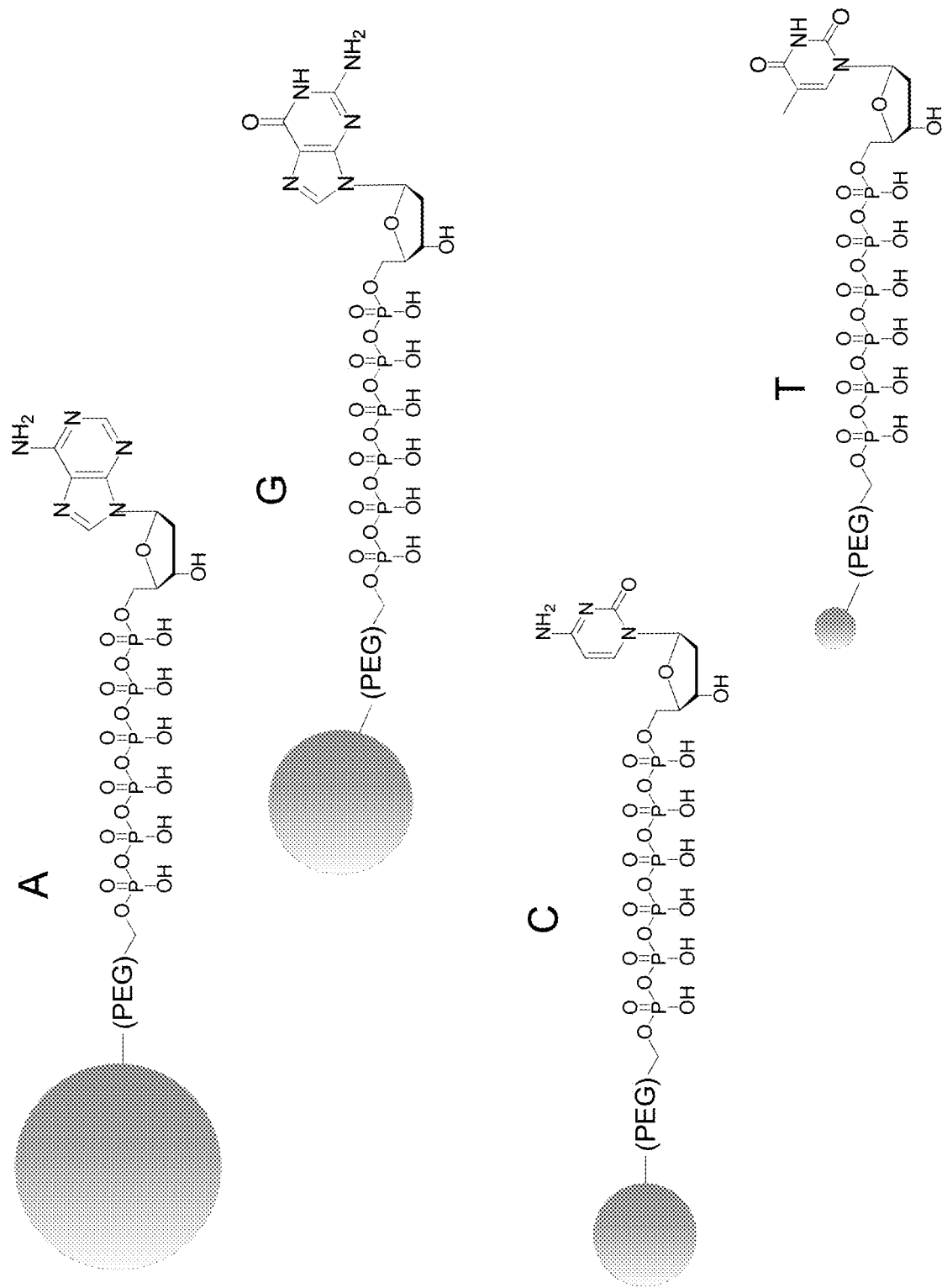
FIG. 10 shows an exemplary set of nucleotide analogs providing four differentiable capacitive labels.

A sequencing solution is added to the reservoir such that the sequencing system is in contact with the chip. In some cases, a counter electrode in contact with the sequencing solution is also used. The sequencing solution has the components required for polymerase activity as well as having ions at the levels required for tuning the capacitive behavior of the system. The solution has potassium ions to maintain the appropriate electrolytic levels, and has Mg++ or Mn++ as required for the activity of the polymerase enzyme. The sequencing solution also has four differently labeled nucleotide analogs shown in FIG. 10. Each of the analogs has a nucleotide portion comprising a hexaphosphate, a deoxy ribose, and a nucleobase. Attached to the terminal phosphate of the nucleotide moiety is a polyethylene glycol (PEG) linker. The PEG linker has 77 PEG units and is connected to the capacitive label. Attached to each of the nucleotide analogs is a sphere of a different size. In this example, polystyrene spheres are used. In other examples, for example, titanium dioxide, or gold spheres are used. The nucleotide analog corresponding to G has a polystyrene sphere with diameter of about 15 nm. The nucleotide analog corresponding to A has a polystyrene sphere with diameter of about 25 nm. The nucleotide analog corresponding to T has a polystyrene sphere with diameter of about 5 nm, and the nucleotide analog corresponding to C has a polystyrene sphere with diameter of about 10 nm.

When all of the reagents required for nucleic acid synthesis are present, the polymerase enzyme proceeds to add nucleotides to the primer to produce a nascent strand. While a nucleotide analog to be incorporated is associated with the enzyme, the capacitive label is sensed by a change in capacitance the nano-electrode pair. Once a nucleotide from a nucleotide analog is added to the nascent strand, the label is cleaved and released.

For electrical measurements, two sub-femtoamp remote SourceMeters are used both as voltage source to bias the electrodes and as impedance/capacitance detection element. In order to select the AC current profile for sequencing, an experiment is performed in which the frequency of the current on the electrodes is swept and the impedance at the electrodes is monitored. The characteristics of the peaks are determined to fine tune the set of frequencies that give the best detection performance and the best differentiation between the nucleotide analogs.

For detection of sequencing, the SourceMeter cycles several frequency levels, When a nucleotide analog is being incorporated into the growing strand, it is held in the enzyme active site, and therefore held near the electrodes, for a longer period of time than a diffusing species would spend near the electrodes. In some cases, the mean time in the active site for a nucleotide that is incorporated is 100 to 500 milliseconds. Peaks of impedance or capacitance are observed for the period of time that the nucleotide analog is in the active site of the enzyme. The distinction between the nucleotide analogs is made on the basis of the amount of change in capacitance that is observed. During a given incorporation event, the frequency levels are alternated hundreds of times. Having multiple points allows for improved signal to noise. Base calling software is then used to call incorporated bases using the combined capacitance data from the multiple measurements.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A chip for sequencing a plurality of single nucleic acid template molecules comprising:
   a substrate comprising;
      a plurality multi-layer capacitive devices,
         each capacitive device comprising a lower electrode layer, above the lower electrode a first insulating layer, above the first insulating layer an upper electrode layer, and above the upper electrode layer a second insulating layer, wherein an edge of the capacitive device is exposed whereby an edge of the lower electrode layer, an edge of the first insulating layer, and an edge of the upper electrode layer are in contact with a sequencing reaction mixture;
         wherein, for each of the of the capacitive devices, a single polymerase enzyme complex comprising a template nucleic acid is bound to the edge of the first insulating layer, which is in contact with the sequencing reaction mixture that comprises;
      a plurality of types of nucleotide analogs each having different capacitive labels; and
      a plurality of electrical connection sites for bringing current and voltage to the capacitive devices, and for receiving electrical signals from the devices.

2. The chip of claim 1 wherein the substrate comprises greater than 1,000 capacitive devices.

3. The chip of claim 1 wherein the substrate comprises greater than 10,000 capacitive devices.

4. The chip of claim 1 wherein the substrate comprises about 1,000 capacitive devices to about 10 million capacitive devices.

5. The chip of claim 1 wherein the substrate comprises about 10,000 capacitive devices to about 1 million capacitive devices.

6. The chip of claim 1 wherein each electrode is electrically connected to an electrical interconnection through which the electrode is brought to the frequencies and through which the capacitance is measured.

7. The chip of claim 1 wherein the substrate comprises electronic elements for one or more of: providing alternating current to the electrodes, measuring the capacitance at the nanoscale electrodes, analog to digital conversion, signal processing, and data storage.

8. The chip of claim 7 wherein the electrical elements are CMOS elements.

9. The chip of claim 1 wherein the first insulating layer comprises $SiO_2$.

10. The chip of claim 1 wherein the material comprising the first insulating layer is different than the material comprising the second insulating layer.

11. The chip of claim 1 wherein the second insulating layer comprises silicon nitride or aluminum oxide.

12. The chip of claim 1 wherein the lower electrode layer and upper electrode layer are at an angle with respect to one another.

13. The chip of claim 1 wherein the first insulting layer has a thickness of between 2 nm and 20 nm.

14. The chip of claim 1 wherein the insulting layer has a decreasing thickness toward the edge that is exposed.

15. The chip of claim 1 further comprising an array of control electrodes.

16. The chip of claim 15 comprising between control electrode for each 10 devices to one control electrode for each 1000 devices.

17. The chip of claim 1 wherein the electrode layers comprise aluminum, silver, gold, or platinum.

18. The chip of claim 1 wherein the substrate comprises silicon.

\* \* \* \* \*